(12) United States Patent
Stark et al.

(10) Patent No.: US 8,389,555 B2
(45) Date of Patent: Mar. 5, 2013

(54) MEDICAMENTS

(75) Inventors: Holger Stark, Bad Homburg (DE); Jukka Matti Leppanen, Kuopio (FI); Britta Caroline Sasse, Montreal (CA); Oliver Saur, Heppenheim (DE); Tim Kottke, Frankfurt am Main (DE); Michael Peter Hill, Manchester (GB)

(73) Assignee: Motac Neuroscience Limited, Manchester (GB)

( * ) Notice: Subject to any disclaimer, the term of this patent is extended or adjusted under 35 U.S.C. 154(b) by 155 days.

(21) Appl. No.: 12/740,147

(22) PCT Filed: Oct. 28, 2008

(86) PCT No.: PCT/GB2008/003623
§ 371 (c)(1),
(2), (4) Date: Apr. 28, 2010

(87) PCT Pub. No.: WO2009/056805
PCT Pub. Date: May 7, 2009

(65) Prior Publication Data
US 2011/0046153 A1    Feb. 24, 2011

(30) Foreign Application Priority Data
Oct. 31, 2007 (GB) .................................. 0721332.5

(51) Int. Cl.
*A61K 31/425* (2006.01)
*C07D 277/60* (2006.01)
*C07D 277/62* (2006.01)

(52) U.S. Cl. ....................... 514/367; 548/152
(58) Field of Classification Search ................. 514/367; 548/152
See application file for complete search history.

(56) References Cited

U.S. PATENT DOCUMENTS
6,084,130 A    7/2000   Romero

FOREIGN PATENT DOCUMENTS
| WO | WO 96/28157 | 9/1996 |
| WO | WO 02/098367 | 12/2002 |
| WO | WO 2005/092871 | 10/2005 |

OTHER PUBLICATIONS

International Search Report, PCT/GB08/03623, dated Apr. 3, 2009.
Maillard, et al. (1994) European Journal of Medicinal Chemistry, Editions Scientifique Elsevier, Paris, FR 19(5):451-456 "Synthese de derives amines du tetrahydro-4, 5, 6, 7 benzothiazole, I. Amines et N-methylamines en positions 4, 5, 6 et 7 a activite dopaminergique centrale".

*Primary Examiner* — Paul Zarek
(74) *Attorney, Agent, or Firm* — Swanson & Bratschun, L.L.C.

(57) ABSTRACT

A compound of formal (I) is described: wherein $R^1$ and $R^2$ are as defined in the text and wherein the compounds are intended for use in treating medical conditions characterized by an imbalance in dopamine receptor activity.

21 Claims, 8 Drawing Sheets

MEDICAMENTS

RELATED APPLICATIONS

This application is a 35 U.S.C. §371 national phase application of PCT/GB2008/003623 (WO 2009/056805), filed on Oct. 28, 2008, entitled "Medicaments", which application claims the benefit of United Kingdom Application No. 0721332.5, filed Oct. 31, 2007, which is incorporated herein by reference in its entirety.

The present invention relates to novel dopamine receptor ligands that can be used to treat a number of medical conditions including, but not limited to, movement disorders (e.g. Parkinson's disease), other neurological disorders, psychiatric disorders and the treatment of drug abuse.

Movement and other disorders due to dysfunction of the basal ganglia and related brain structures are of major socio-economic importance. Such disorders can occur as a consequence of inherited or acquired disease, idiopathic neurodegeneration or they may be iatrogenic. The spectrum of disorders is very diverse, ranging from those associated with poverty of movement (akinesia, hypokinesia, bradykinesia) and hypertonia (e.g. Parkinson's disease, some forms of dystonia) to the involuntary movement disorders (hyperkinesias or dyskinesias e.g. Huntington's disease, levodopa-induced dyskinesia, ballism, and some forms of dystonia).

Parkinsonism is a well-known movement disorder comprising a syndrome characterised by slowness of movement (bradykinesia), rigidity and/or tremor. Parkinsonian symptoms are seen in a variety of conditions, most commonly in idiopathic parkinsonism (i.e., Parkinson's disease) but also following treatment of schizophrenia, exposure to toxins/drugs and head injury. In Parkinson's disease the primary pathology is degeneration of dopaminergic neurons of the substantia nigra, pars compacta.

There are a number of medicaments available for the treatment of movement disorders and these include agents such as apomorphine, cabergoline or bromocriptine. However the "main stay" of current therapies for movement disorders such as Parkinson's disease are based around the use of Levodopa and other agonists of dopamine receptors.

Levodopa (or L-DOPA) is based on an aromatic amino acid and has the chemical name: (−)-L-α-amino-β-(3,4-dihydroxybenzene)propanoic acid. L-DOPA has the molecular formula $C_9H_{11}NO_4$ and a molecular weight of 197.2. Chemically, levodopa is (−)-3-(3,4-dihydroxy-phenyl)-L-alanine. It is a colourless, crystalline compound, slightly soluble in water and insoluble in alcohol. L-DOPA has the following structural formula:

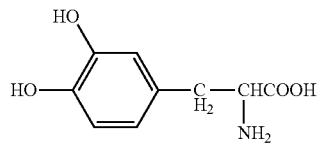

L-DOPA is commonly administered to patients in combination with carbidopa. The chemical name for carbidopa is (−)-L-α-hydrazino-α-methyl-β-(3,4-dihydroxybenzene)propanoic acid monohydrate. Carbidopa has the empirical formula $C_{10}H_{14}N_2O_4 \cdot H_2O$ and a molecular weight of 244.3. Anhydrous carbidopa has a molecular weight of 226.3. Sinemet® is a combination of carbidopa and levodopa for the treatment of Parkinson's disease and syndrome. Sinemet® is described in U.S. Pat. Nos. 4,832,957 and 4,900,755. The structural formula of carbidopa is:

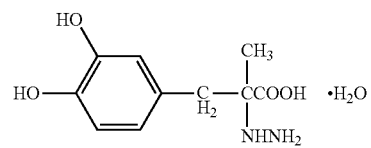

Ropinirole is an example of another dopamine agonist used for treating movement disorders. It is a non-ergoline dopamine agonist (sold under the trademark Requip®) and is the hydrochloride salt of 4-[2-(dipropylamino)ethyl]-1,3-dihydro-2H-indol-2-one monohydrochloride. Roprinrole has an empirical formula of $C_{16}H_{24}N_2O \cdot HCl$ and a molecular weight of 296.84 (260.38 as the free base). Ropinirole is described in U.S. Pat. Nos. 4,452,808 and 4,824,860 and has the structural formula:

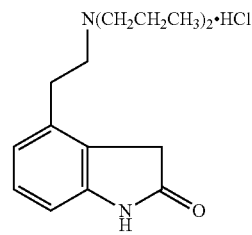

L-DOPA and other conventional dopamine receptor agonists have a number of drawbacks.

One common problem is that dyskinesias can arise is as a side-effect of dopamine replacement therapy. Dyskinesias are abnormal involuntary movement disorders. The abnormal movements may manifest as chorea (involuntary, rapid, irregular, jerky movements that may affect the face, arms, legs, or trunk), ballism (involuntary movements similar to chorea but of a more violent and forceful nature), dystonia (sustained muscle contractions, usually producing twisting and repetitive movements or abnormal postures or positions) or athetosis (repetitive involuntary, slow, sinuous, writhing movements, which are especially severe in the hands). Dyskinetic side-effects can be seen either when the patient is undergoing dopamine-replacement therapy (in the case of chorea and/or dystonia) or even when off therapy (when dystonia is prevalent). Ultimately, these side-effects severely limit the usefulness of dopaminergic treatments.

Another problem associated with dopamine-replacement agents (e.g. L-DOPA and dopamine receptor agonists) is the "wearing-off" of the anti-parkinsonian efficacy of the treatment.

Other problems associated with dopamine-replacement agents include side-effects such as nausea, dizziness, somnolence, insomnia, constipation, asthenia and hallucination.

Efforts have been made in the art to improve the efficacy of dopamine receptor agonists and also to develop agents with fewer side-effects. One area of development has been to investigate whether of not compounds can be developed that have selectivity and/or specificity towards different types of dopamine receptor. A number of subtypes of dopamine receptor exist and they can be divided into two main groups. The Gs protein coupled D1 and D5 receptors belong to the D1-like dopamine receptor family. Dopamine D2, D3 and D4 receptors are Gi protein coupled and form the D2-like receptor family.

The D3 receptor was first cloned and characterized in 1990 (Sokoloff et al, Molecular cloning and characterization of a novel dopamine receptor (D3) as a target for neuroleptics. Nature, 347, 146-151 (1990)). Overall expression of the D3 receptor is lower than for D2 in the brain. However the D3 receptor is specifically localized in the limbic system and in relatively low concentrations in the striatum. Therefore, the dopamine D3 receptor represents a target for the treatment of movement disorders and also other neurological disorders, psychiatric disorders, the treatment of drug abuse and other therapeutic indications, which are related to the modulation of dopamine receptor activity.

Schizophrenia is another condition that is associated with imbalance in dopamine receptor activity. The dopamine hypothesis of schizophrenia postulates that an excess of dopamine subcortically is associated with the positive symptoms. At the same time, the negative and cognitive symptoms of schizophrenia are thought to arise from a deficit of dopamine in the cortex. Modulators of the dopamine D3 receptor could therefore have a regulative effect on this dopaminergic imbalance without causing negative side effects in the striatum.

Addiction to substances of abuse (especially alcohol, nicotine, cocaine and heroine) is associated with abnormalities in the limbic system. Given the relatively high concentration of dopamine D3 receptors in the limbic system, it is postulated that selective dopamine D3 receptor ligands also have potential for the treatment of compounds of abuse. Agonists could be useful for a substitute therapy whereas selective D3 receptor antagonists or partial agonists would attenuate the desired dopamine receptor stimulation of the abused drug without producing undesired side effects (Newman et al, dopamine D3 receptor partial agonists and antagonists as potential drug abuse therapeutic agents, *J. Med. Chem.* 2005, 48, 3663-3679). In this respect, it will also be appreciated that abusive food and drink consumption may be associated with imbalances in the limbic system and comparable changes in dopamine neurotransmitter cross-talk. Accordingly selective dopamine D3 receptor ligands may also be useful for helping to control obesity or under-eating (anorexia).

Sexual dysfunctions, for example wherein a male is unable to develop or maintain a penile erection or female sexual arousal/orgasm disorder, are also associated with an imbalance of dopamine receptor activity.

Restless leg syndrome is of unknown aetiology and often treated with low dose dopamine agonists because an imbalance of this neurotransmitter largely influences this disorder and/or its symptoms.

Many other conditions are associated with an imbalance in dopamine receptor activity. This include: bipolar disorder, attention deficit hyperactivity disorder (ADHD), Tourette's syndrome, depression, anxiety, cognitive impairment, dementia, emesis, amnesia, autism, vertigo as well as eating, sleep, movement, obsessive/compulsive, circadian rhythm and gastric motility disorders are accompanied with a dysfunction of the dopaminergic system. An abnormal dopaminergic neurotransmission is also associated with conditions such as migraine, amyotropic lateral sclerosis, sleep disorder and anhedonia.

It will be appreciated that all of the abovementioned conditions, as well as any other conditions associated with an imbalance in dopamine receptor activity, may be treated with selective dopamine D3 receptor ligands. A number of steps have been taken to develop dopamine D3 receptor ligands for use by clinicians.

Pramipexol is an example of a D3 receptor agonist that has been developed for the treatment of movement disorders and the antiparkinson activity of pramipexol has been described in U.S. Pat. No. 4,731,374. The chemical name of pramipexole is (S)-2-amino-4,5,6,7-tetra-hydro-6-(propylamino)benzothiazole dihydrochloride mono-hydrate. Pramipexole dihydrochloride is sold under the trademark Mirapex®. Pramipexole dihydrochloride has the empirical formula $C_{10}H_{17}N_3S \cdot 2HCl \cdot H_2O$ and a molecular weight of 302.27. The structural formula of pramipexole dihydrochloride is:

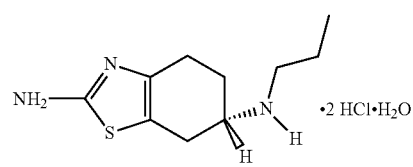

A structure closely related to pramipexole is described and named as "etrabamine" and has the structural formula:

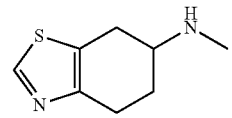

However pramipexole and etrabamine are still associated with a number of drawbacks. For instance 1-10% of patients treated with pramipexole may develop oedema. Other known side-effects include dyskinetic side-effects, insomnia, hallucination and orthostatic dysregulation.

U.S. Pat. No. 7,049,337 discloses N-(2'-propynyl)-substituted 2-aminotetralin compounds and their use in treating central nervous system disorders. There is no disclosure in U.S. Pat. No. 7,049,337 of a 4,5,6,7-tetrahydro-benzothiazole compound that does not contain a substituent on the thiazole ring and that contains a polar group on the 4,5,6,7-tetrahydro-benzo ring.

WO-02/098367 discloses hybrid compounds containing both an aminotetralin moiety or related structure and an N'-aryl piperazinyl structure linked to the aminotetralin structure by an alkaline bridge and the use of the compounds in altering central nervous system activity. There is no discolosure in WO-02/098367 of a 4,5,6,7-tetrahydro-benzothiazole compound that does not contain a substituent on the thiazole ring.

WO-96/28157 discloses pharmaceutical compositions containing 1-etrabamine and methods for making them. WO-96/28157 discloses the compound 6-ethoxycarbonylamino-4,5,6,7-tetrahydrobenzo[d]thiazole as an intermediate in the preparation of 1-etrabamine.

An object of the present invention is to provide new and improved dopamine receptor ligands that may be used to treat medical conditions associated with an imbalance in dopamine receptor activity.

A further object of the present invention is to develop new chemical compounds which obviate or mitigate one or more of the drawbacks associated with the above mentioned prior art compounds.

According to an aspect of the present invention there is provided a compound of formula (I):

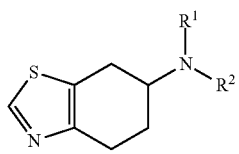

(I)

wherein

R¹ is selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, and substituted or unsubstituted heterocyclic ring; and R² comprises a polar moiety, P. Preferably the polar moiety, P, is not an ester group, especially not an ethyl ester group.

According to another aspect of the present invention there is provided a compound of formula (I):

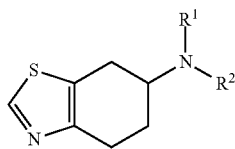

(I)

wherein

R¹ is selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, and substituted or unsubstituted heterocyclic ring; and R² comprises a polar moiety, P, and at least one linking group, Z, linking the polar moiety, P, to the nitrogen of the NR¹ group. The at least one linking group, Z, may be selected from one or more of the group consisting of substituted or unsubstituted alkylene, substituted or unsubstituted alkenylene, substituted or unsubstituted alkynylene, substituted or unsubstituted carbocyclic ring, and substituted or unsubstituted heterocyclic ring.

Another aspect of the present invention provides a pharmaceutical composition comprising a compound of formula (I) according to the present invention.

Another aspect of the present invention provides a compound of formula (I) according to the present invention for use in the manufacture of a medicament for the treatment of medical conditions characterized by an imbalance in dopamine receptor activity.

Another aspect of the present invention provides a use of compounds of formula (I) according to the present invention for treatment of medical conditions characterized by an imbalance in dopamine receptor activity.

Another aspect of the present invention provides a method of treating medical conditions characterized by an imbalance in dopamine receptor activity comprising administering to a subject in need thereof a therapeutically effective amount of a compound of formula (I) according to the present invention.

In the subject invention a "therapeutically effective amount" is any amount of a compound or composition which, when administered to a subject suffering from a disease against which the compounds are effective, causes reduction, remission, or regression of the disease.

A "subject" is a vertebrate, mammal, domestic animal or human being.

In the practice of this invention the "pharmaceutically acceptable vehicle" is any physiological vehicle known to those of ordinary skill in the art useful in formulating pharmaceutical compositions.

Compounds According to the Invention

The inventors generated a large number of compounds and tested their ability to bind to dopamine receptors and to treat medical conditions characterized by an imbalance in dopamine receptor activity. They discovered that numerous compounds that were related to pramipexole or etrabamine had poor binding for dopamine receptors and/or little efficacy (data not shown). However they were surprised to find that compounds that fall within the definition of the formula (I) according to the invention have particularly good affinity for dopamine D3 receptors and are also effective for reducing the effects of the medical conditions when tested in in vivo models (see the Examples). In particular, the inventors have discovered that compounds according to the formula (I) including at least one linking group Z have particularly good affinity for dopamine D3 receptors and are also effective for reducing the effects of the medical conditions when tested in in vivo models (see the Examples).

Nature of R¹

In the compounds of formula (I), R¹ is selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, and substituted or unsubstituted heterocyclic ring.

In this specification, unless otherwise indicated, the term "alkyl" when used alone or in combination, includes both straight chain and branched chain alkyl groups, such as propyl, isopropyl and tert-butyl. However, references to individual alkyl groups such as "propyl" are specific for the straight-chain version only (for example otherwise known as n-propyl) and references to individual branched-chain alkyl groups such as "isopropyl" are specific for the branched-chain version only. A $C_1$-$C_4$ alkyl group has from one to four carbon atoms including methyl, ethyl, propyl, isopropyl, butyl, tert-butyl, and the like.

R¹ may take any desirable substitution pattern subject to the definition set out above. In some preferred embodiments it may be desirable for R¹ to incorporate a polar moiety as defined below. Where both R¹ and R² incorporate a polar moiety, the polar moiety forming part of R¹ may be the same or different to the polar moiety forming part of R². In the preferred embodiments of the compound of the invention where R¹ incorporates a polar moiety, the R¹ polar moiety may be linked to the nitrogen atom to which R¹ and R² are connected via any desirable linking group. The R¹ linking group may take any of the forms set out herein in respect of the linking group, Z, which is discussed below in relation to R². An example of a suitable R¹ linking group is a substituted or unsubstituted oxyalkyl group.

R¹ may in one aspect be selected from the group consisting of H and a substituted or unsubstituted alkyl, alkenyl, alkynyl or alkoxy group, especially from the group consisting of H and a substituted or unsubstituted alkyl, alkenyl or alkynyl group. For example, R¹ may contain 1 to 10 carbon atoms, more preferably 1 to 8 carbon atoms, and R¹ may be selected from the group consisting of H and a $C_1$-$C_4$ substituted or unsubstituted alkyl, alkenyl, alkynyl or alkoxy group. References herein to a R¹ group containing 1 to 10 carbon atoms relate to the $R^1$ group, for example the alkyl, alkenyl, alkynyl or alkoxy group, and not to any substituents provided on the $R^1$ group.

$R^1$ is preferably a substituted or unsubstituted alkyl, alkenyl, alkynyl or alkoxy group, which may contain any desirable number of carbon atoms. For example, $R^1$ may contain 1 to 10 carbon atoms, more preferably 1 to 8 carbon atoms and most preferably $R^1$ is a $C_1$-$C_4$ substituted or unsubstituted alkyl, alkenyl, alkynyl or alkoxy group.

$R^1$ may in one aspect be selected from the group consisting of H and an unsubstituted alkyl, alkenyl or alkynyl group, such as from the group consisting of H, methyl, ethyl, propyl, allyl, prop-2-ynyl and but-2-ynyl.

It is preferred that said substituted or unsubstituted alkyl, alkenyl, alkynyl or alkoxy group is substituted with a first substituent which contains an atom other than a carbon or hydrogen atom. Said atom may be selected from any one of groups 15, 16 or 17 of the periodic table. More preferably said atom is selected from the group consisting of oxygen, sulfur, selenium, nitrogen and phosphorus.

The first substituent may be selected from the group consisting of a carboxy group, a thiocarboxy group, a selenocarboxy group, a carboxamido group, a sulfo group, a sulfino group, a sulfeno group, an ester group, a haloformyl group, a carbamoyl group, an imido group, a cyanato group, an isocyanato group, a nitro group, a nitroso group, a nitroxy group, a nitrosooxy group, a formyl group, an oxo group, a hydroxy group, a hydroperoxy group, an oxy group, a peroxy group, a phosphono group, a sulfonyl group, a sulfinyl group, an isothiocyanato group, a thioformyl group, a thiono group, a sulfanyl group, a thio group, a disulfanyl group, a selenyl group, a seleno group, an amidino group, a cyano group, an isocyano group, an amino group, an imino group, an azido group, an azo group, a hydrazino group, a phosphino group and a phospho group, and derivatives thereof.

The first substituent may be any group which contains one or more oxygen atoms, optionally in combination with at least one further atom which is other than carbon or hydrogen, for example, sulfur, selenium, nitrogen and/or phosphorous. Preferably the first substituent is selected from the group consisting of a carboxy group, a thiocarboxy group, a selenocarboxy group, a carboxamido group, a sulfo group, a sulfino group, a sulfeno group, an ester group, a haloformyl group, a carbamoyl group, an imido group, a cyanato group, an isocyanato group, a nitro group, a nitroso group, a nitroxy group, a nitrosooxy group, a formyl group, an oxo group, a hydroxy group, a hydroperoxy group, an oxy group, a peroxy group, a phosphono group, a phospho group, and derivatives thereof. For example, the first substituent may be selected from the group consisting of a carboxy group, a thiocarboxy group, a carboxamido group, a sulfo group, a sulfino group, a sulfeno group, an ester group, a carbamoyl group, an imido group, a nitro group, a formyl group, an oxo group, a hydroxy group, an oxy group, and derivatives thereof.

Alternatively said first substituent may be any group which contains one or more sulfur atoms, optionally in combination with at least one further atom which is other than carbon or hydrogen, for example, oxygen, selenium, nitrogen and/or phosphorous. Preferably the first substituent is selected from the group consisting of a thiocarboxy group, a sulfo group, a sulfino group, a sulfeno group, a sulfonyl group, a sulfinyl group, an isothiocyanato group, a thioformyl group, a thiono group, a sulfanyl group, a thio group, a disulfanyl group and derivatives thereof. For example, the first substituent may be selected from the group consisting of a thiocarboxy group, a sulfo group, a sulfino group, a sulfeno group, a sulfonyl group, a sulfinyl group, a thioformyl group, a sulfanyl group, a thio group, a disulfanyl group and derivatives thereof.

As a further alternative the first substituent may be any group which contains one or more selenium atoms, optionally in combination with at least one further atom which is other than carbon or hydrogen, for example, oxygen, sulfur, nitrogen and/or phosphorous. Preferably the first substituent is selected from the group consisting of a selenocarboxy group, a selenyl group, a seleno group and derivatives thereof.

Moreover, said first substituent may be any group which contains one or more nitrogen atoms, optionally in combination with at least one further atom which is other than carbon or hydrogen, for example, oxygen, sulfur, selenium and/or phosphorous. Preferably the first substituent is selected from the group consisting of a carbamoyl group, an imido group, an amidino group, a cyano group, an isocyano group, an amino group, an imino group, an azido group, an azo group, a cyanato group, an isocyanato group, an isothiocyanato group, a nitro group, a nitroso group, a nitroxy group, a nitrosooxy group, a hydrazino group, and derivatives thereof. For example, the first substituent may be selected from the group consisting of a carbamoyl group, an imido group, an amidino group, a cyano group, an amino group, an imino group, an azido group, a nitro group, a hydrazino group, and derivatives thereof.

Said first substituent may be any group which contains one or more phosphorous atoms, optionally in combination with at least one further atom which is other than carbon or hydrogen, for example, oxygen, sulfur, selenium and/or nitrogen. Preferably the first substituent is selected from the group consisting of a phosphino group, a phosphono group, a phospho group, and derivatives thereof.

Furthermore, said first substituent may be selected from the group consisting of a substituted or unsubstituted carbocyclic group and a substituted or unsubstituted heterocyclic group.

The carbocyclic group may contain any desirable number of carbocyclic rings, and the or each ring may contain any appropriate number of ring carbon atoms. Where the first substituent is a multi- or poly-cyclic carbocyclic ring structure, the connection between any two of said plurality of rings may have a fused, bridged or spiro configuration. It is particularly preferred that the or each carbocyclic ring contains 3 to 12 carbon atoms, more preferably 4 to 8 carbon atoms, and most preferably 5 to 7 carbon atoms. The carbocyclic group may be a saturated, unsaturated or aromatic carbocyclic group. Examples of preferred saturated monocyclic carbocyclic groups include a cyclopentanyl group and a cyclohexanyl group. A preferred multicyclic carbocyclic group is an adamantanyl group. Examples of preferred aromatic carbocyclic groups include phenyl, naphthyl, anthracyl and phenanthracyl groups.

The first substituent may be selected from the group consisting of a cyclopentanyl group, a cyclohexanyl group, an adamantanyl group, a phenyl group, a naphthyl group, an anthracyl group and a phenanthracyl group.

The heterocyclic group may contain any suitable number of heterocyclic rings, and the or each ring may contain any desirable number of ring atoms. Where the first substituent is a multi- or poly-cyclic heterocyclic ring structure, provided at least one of said rings is a heterocyclic ring, the or each other ring may be a carbocyclic ring or a further heterocyclic ring. The connection between any two of the plurality of rings may have a fused, bridged or spiro configuration. It is particularly preferred that the or each heterocyclic ring contains 3 to 12 carbon atoms, more preferably 4 to 8 carbon atoms, and most preferably 5 to 7 carbon atoms. The heterocyclic group may be a saturated, unsaturated or aromatic heterocyclic group.

The substituted or unsubstituted heterocyclic group contains at least one ring heteroatom, that is, an atom other than carbon. The heteroatom may be taken from group 15 or 16 of the periodic table and is preferably selected from the group consisting of oxygen, sulfur, selenium, nitrogen and phosphorous.

The first substituent may be selected from the group consisting of an oxiranyl group, an oxirenyl group, an oxetanyl group, a furanyl group, a hydrofuranyl group, an oxazolyl group, an isoxazolyl group, a pyranyl group, a hydropyranyl group, an oxazinyl group, a dioxanyl group, an aziridine group, an azetidinyl group, a pyrrolyl group, a hydropyrrolyl group, a pyrazolyl group, an imidazolyl group, a triazolyl group, a tetrazolyl group, a thiazolyl group, an isothiazolyl group, a piperidinyl group, a pyridinyl group, a pyridazinyl group, a pyrimidinyl group, a pyrazinyl group, a piperazinyl group, an oxoazinyl group, a thiazinyl group, a thiiranyl group, a thiophenyl group, a hydrothiophenyl group, a dithiolanyl group, a thianyl group, a thiinyl group, a thiazine group, and a dithianyl group, and their partly and fully saturated analogues.

The substituted or unsubstituted heterocyclic group may be selected from the group consisting of an oxiranyl group, an oxirenyl group, an oxetanyl group, a furanyl group, a hydrofuranyl group, an oxazolyl group, an isoxazolyl group, a pyranyl group, a hydropyranyl group, an oxazinyl group, and a dioxanyl group, and their partly and fully saturated analogues. For example, the substituted or unsubstituted heterocyclic group may be selected from the group consisting of a furanyl group, an oxazolyl group, an isoxazolyl group, a pyranyl group, an oxazinyl group, and a dioxanyl group, and their partly and fully saturated analogues.

The substituted or unsubstituted heterocyclic group may be selected from the group consisting of an aziridine group, an azetidinyl group, a pyrrolyl group, a hydropyrrolyl group, a pyrazolyl group, an imidazolyl group, a triazolyl group, a tetrazolyl group, an oxazolyl group, a thiazolyl group, an isothiazolyl group, a piperidinyl group, a pyridinyl group, a pyridazinyl group, a pyrimidinyl group, a pyrazinyl group, a piperazinyl group, an oxoazinyl group, and a thiazinyl group, and their partly and fully saturated analogues. For example, the substituted or unsubstituted heterocyclic group may be selected from the group consisting of an aziridine group, a pyrrolyl group, a pyrazolyl group, an imidazolyl group, a triazolyl group, a tetrazolyl group, an oxazolyl group, a thiazolyl group, an isothiazolyl group, a pyridinyl group, a pyridazinyl group, a pyrimidinyl group, a pyrazinyl group, a piperazinyl group, an oxoazinyl group, and a thiazinyl group, and their partly and fully saturated analogues.

Alternatively the substituted or unsubstituted heterocyclic group may be selected from the group consisting of a thiiranyl group, a thiophenyl group, a hydrothiophenyl group, a thiazolyl group, an isothiazoly group, a dithiolanyl group, a thianyl group, a thiinyl group, a thiazine group, and a dithianyl group, and their partly and fully saturated analogues. For example, the substituted or unsubstituted heterocyclic group may be selected from the group consisting of a thiophenyl group, a hydrothiophenyl group, a thiazolyl group, an isothiazoly group, a dithiolanyl group, a thianyl group, a thiinyl group, a thiazine group, and a dithianyl group, and their partly and fully saturated analogues.

Nature of $R^2$ $R^2$ comprises a polar moiety, P, and preferably at least one linking group, Z, linking the polar moiety (P) to the nitrogen of the $NR^1$ group. In the context of the present invention the term 'polar moiety' is intended to refer to any moiety that contains an uneven, i.e. polarized, distribution of electrons across or between the atoms that constitute the moiety. By way of example only, a polar moiety may contain a combination of atoms in which some atoms are carbon and hydrogen atoms and one or more other atoms is/are other than carbon and/or hydrogen atoms, such as one or more heteroatoms, for example atoms from group 15, 16 or 17 of the periodic table. For example, an ethoxy group (R—O—$C^1H_2$—$C^2H_3$) may be considered a polar moiety in view of the fact that the distribution of electrons around the carbon atom ($C^1$) bonded to the oxygen atom is different to the electronic distribution around the other carbon atom ($C^2$), which is largely attributable to the oxygen atom being significantly more electronegative than either carbon atom or the hydrogen atoms bonded to the carbon atoms.

The polar moiety, P, forming part of substituent $R^2$, can be any desirable chemical group provided it contains an uneven electronic distribution as mentioned above. As will be appreciated by the skilled person, selection of an appropriate polar moiety can significantly affect the physical, chemical and/or biological properties of the compound of interest.

The polar moiety, P, may be any organic group which contains at least one atom which is other than a carbon or hydrogen atom. The polar moiety may be selected from the group consisting of substituted alkyl, substituted alkenyl, substituted alkynyl, substituted alkoxy, substituted or unsubstituted amino, substituted carbocyclic ring, and substituted or unsubstituted heterocyclic ring. The substituent(s) appended to any of the aforementioned substituted groups may be any atom(s) other than a carbon or hydrogen atom. For example, the substituent(s) may be selected from any one of groups 15, 16 or 17 of the periodic table. By way of further example, the substituent(s) may be nitrogen, phosphorous, oxygen, sulfur, selenium, chlorine or bromine or, where a plurality of substituents is provided, any combination thereof.

It is preferred that said polar moiety comprises at least one heteroatom selected from the group consisting of oxygen, sulfur, selenium, nitrogen and phosphorus. Most preferably the polar moiety includes one or more carbon atoms in combination with said heteroatom(s).

The polar moiety may, for example, be selected from the group consisting of a carboxy group, a thiocarboxy group, a selenocarboxy group, a carboxamido group, a sulfo group, a sulfino group, a sulfeno group, an ester group, a haloformyl group, a carbamoyl group, an imido group, a cyanato group, an isocyanato group, a nitro group, a nitroso group, a nitroxy group, a nitrosooxy group, a formyl group, an oxo group, a hydroxy group, a hydroperoxy group, an oxy group, a peroxy group, a phosphono group, a thiocarboxy group, a sulfonyl group, a sulfinyl group, an isothiocyanato group, a thioformyl group, a thiono group, a sulfanyl group, a thio group, a disulfanyl group, a selenocarboxy group, a selenyl group, a seleno group, an amidino group, a cyano group, an isocyano group, an amino group, an imino group, an azido group, an azo group, a hydrazino group, a phosphino group and a phospho group, and derivatives thereof.

The polar moiety, P, may be any group which contains one or more oxygen atoms, optionally in combination with at least one further atom which is other than carbon or hydrogen, for example, sulfur, selenium, nitrogen and/or phosphorous. Preferably the polar moiety, P, is selected from the group consisting of a carboxy group, a thiocarboxy group, a selenocarboxy group, a carboxamido group, a sulfo group, a sulfino group, a sulfeno group, an ester group, a haloformyl group, a carbamoyl group, an imido group, a cyanato group, an isocyanato group, a nitro group, a nitroso group, a nitroxy group, a nitrosooxy group, a formyl group, an oxo group, a hydroxy group, a hydroperoxy group, an oxy group, a peroxy group, a phosphono group, a phospho group, and derivatives thereof. For example, the polar moiety, P, may be selected from the group consisting of a carboxy group, a thiocarboxy group, a carboxamido group, a sulfo group, a sulfino group, a sulfeno group, an ester group, a carbamoyl group, an imido group, a nitro group, a formyl group, an oxo group, a hydroxy group, an oxy group, and derivatives thereof.

Alternatively said polar moiety, P, may be any group which contains one or more sulfur atoms, optionally in combination with at least one further atom which is other than carbon or hydrogen, for example, oxygen, selenium, nitrogen and/or phosphorous. Preferably the polar moiety, P, is selected from the group consisting of a thiocarboxy group, a sulfo group, a sulfino group, a sulfeno group, a sulfonyl group, a sulfinyl group, an isothiocyanato group, a thioformyl group, a thiono group, a sulfanyl group, a thio group, a disulfanyl group and derivatives thereof. For example, the polar moiety, P, may be selected from the group consisting of a thiocarboxy group, a sulfo group, a sulfino group, a sulfeno group, a sulfonyl group, a sulfinyl group, a thioformyl group, a sulfanyl group, a thio group, a disulfanyl group and derivatives thereof.

As a further alternative the polar moiety, P, may be any group which contains one or more selenium atoms, optionally in combination with at least one further atom which is other than carbon or hydrogen, for example, oxygen, sulfur, nitrogen and/or phosphorous. Preferably the polar moiety is selected from the group consisting of a selenocarboxy group, a selenyl group, a seleno group and derivatives thereof.

Moreover, said polar moiety, P, may be any group which contains one or more nitrogen atoms, optionally in combination with at least one further atom which is other than carbon or hydrogen, for example, oxygen, sulfur, selenium and/or phosphorous. Preferably the polar moiety, P, is selected from the group consisting of a carbamoyl group, an imido group, an amidino group, a cyano group, an isocyano group, an amino group, an imino group, an azido group, an azo group, a cyanato group, an isocyanato group, an isothiocyanato group, a nitro group, a nitroso group, a nitroxy group, a nitrosooxy group, a hydrazino group, and derivatives thereof. For example, the polar moiety, P, may be selected from the group consisting of a carbamoyl group, an imido group, an amidino group, a cyano group, an amino group, an imino group, an azido group, a nitro group, a hydrazino group, and derivatives thereof.

Said polar moiety, P, may be any group which contains one or more phosphorous atoms, optionally in combination with at least one further atom which is other than carbon or hydrogen, for example, oxygen, sulfur, selenium and/or nitrogen. Preferably the polar moiety, P, is selected from the group consisting of a phosphino group, a phosphono group, a phospho group, and derivatives thereof.

It is preferred that said polar moiety, P, is a substituted or unsubstituted heterocyclic group. The heterocyclic group may contain any suitable number of heterocyclic rings, and the or each ring may contain any desirable number of ring atoms. Where the first substituent is a multi- or poly-cyclic heterocyclic ring structure, provided at least one of said rings is a heterocyclic ring, the or each other ring may be a carbocyclic ring or a further heterocyclic ring. The connection between any two of the plurality of rings may have a fused, bridged or Spiro configuration. It is particularly preferred that the or each heterocyclic ring contains 3 to 12 carbon atoms, more preferably 4 to 8 carbon atoms, and most preferably 5 to 7 carbon atoms. The heterocyclic group may be a saturated, unsaturated or aromatic heterocyclic group.

The substituted or unsubstituted heterocyclic group contains at least one ring heteroatom, that is an atom other than carbon. The heteroatom may be taken from group 15 or 16 of the periodic table and is preferably selected from the group consisting of oxygen, sulfur, selenium, nitrogen and phosphorous.

The substituted or unsubstituted heterocyclic group may be selected from the group consisting of an oxiranyl group, an oxirenyl group, an oxetanyl group, a furanyl group, a hydrofuranyl group, an oxazolyl group, an isoxazolyl group, a pyranyl group, a hydropyranyl group, an oxazinyl group, and a dioxanyl group, and their partly and fully saturated analogues. For example, the substituted or unsubstituted heterocyclic group may be selected from the group consisting of a furanyl group, an oxazolyl group, an isoxazolyl group, a pyranyl group, an oxazinyl group, and a dioxanyl group, and their partly and fully saturated analogues.

The substituted or unsubstituted heterocyclic group may be selected from the group consisting of an aziridine group, an azetidinyl group, a pyrrolyl group, a hydropyrrolyl group, a pyrazolyl group, an imidazolyl group, a triazolyl group, a tetrazolyl group, an oxazolyl group, a thiazolyl group, an isothiazolyl group, a piperidinyl group, a pyridinyl group, a pyridazinyl group, a pyrimidinyl group, a pyrazinyl group, a piperazinyl group, an oxoazinyl group, and a thiazinyl group, and their partly and fully saturated analogues. For example, the substituted or unsubstituted heterocyclic group may be selected from the group consisting of an aziridine group, a pyrrolyl group, a pyrazolyl group, an imidazolyl group, a triazolyl group, a tetrazolyl group, an oxazolyl group, a thiazolyl group, an isothiazolyl group, a pyridinyl group, a pyridazinyl group, a pyrimidinyl group, a pyrazinyl group, a piperazinyl group, an oxoazinyl group, and a thiazinyl group, and their partly and fully saturated analogues.

Alternatively the substituted or unsubstituted heterocyclic group may be selected from the group consisting of a thiiranyl group, a thiophenyl group, a hydrothiophenyl group, a thiazolyl group, an isothiazoly group, a dithiolanyl group, a thianyl group, a thiinyl group, a thiazine group, and a dithianyl group, and their partly and fully saturated analogues. For example, the substituted or unsubstituted heterocyclic group may be selected from the group consisting of a thiophenyl group, a hydrothiophenyl group, a thiazolyl group, an isothiazoly group, a dithiolanyl group, a thianyl group, a thiinyl group, a thiazine group, and a dithianyl group, and their partly and fully saturated analogues.

The polar moiety, P, is preferably selected from the group consisting of an amido group, an inverse amido group, an ether group, a thioether group, a carbamato group, a urea group, a thio urea group, and an amino group, each of these groups optionally incorporating any desirable pattern of further substitution. More preferably, the polar moiety, P, is selected from the group consisting of an amido group, an inverse amido group, an amino group and an oxy group, even more preferably from the group consisting of an amido group, an inverse amido group and an amino group, each of these groups optionally incorporating any desirable pattern of further substitution.

Preferred Embodiments of the Invention

In a preferred embodiment of the present invention there is provided a compound of formula (I) having the formula (Ia):

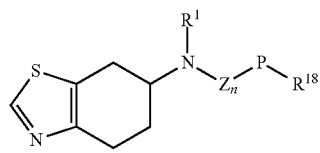

(Ia)

wherein each of $R^1$ and P is as defined above; $R^{18}$ is selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, and substituted or unsubstituted heterocyclic ring; Z is a linking group; and n is any integer, which encompasses 0, 1, 2, 3 etc. Preferably, in this embodiment, n is an integer of at least 1, such as 1, 2, 3 or 4, especially 1, 2 or 3, more especially 1 or 2. In one aspect, n is 1 and in another aspect n is 2. Where n is 0 this is intended to represent embodiments of the present invention where no linking group, Z, is present and the nitrogen atom is bonded directly to the polar group, P. Preferably, in this embodiment, the polar moiety, P, is not an ester group, especially not an ethyl ester group.

In another preferred embodiment of the present invention there is provided a compound of formula (I) having the formula (Ia):

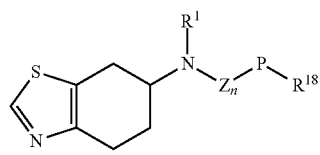

(Ia)

wherein each of $R^1$ and P is as defined above; $R^{18}$ is selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, and substituted or unsubstituted heterocyclic ring; Z is a linking group; and n is any integer of 1 or more. Preferably, in this embodiment, n is 1, 2, 3 or 4, especially 1, 2 or 3, more especially 1 or 2. In one aspect, n is 1 and in another aspect n is 2.

The integer n defines the number of linking groups Z present in the compounds of the invention. For example, when n is 1 then there is one linking group Z, for example selected from the groups listed herein as suitable linking groups. When n is 2, then there are two linking groups Z, for example selected from the groups listed herein as suitable linking groups and which two linking groups Z may be the same or different. The same applies to the other possible integers n.

In a preferred embodiment of the present invention the polar group, P, is a substituted or unsubstituted inverse amido (or inverse carboxamido) group (—N($R^3$)—C(O)—) and $R^{18}$ is represented by $R^4$, so as to provide a compound of formula (I) having the formula (Ib):

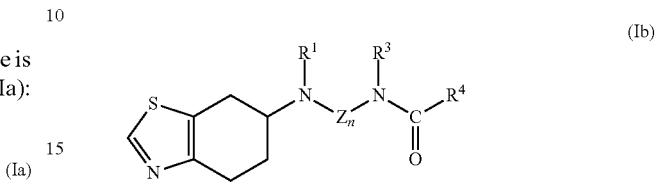

(Ib)

wherein
$R^1$ is as defined above;
each of $R^3$ and $R^4$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^5R^6$, or
$R^3$ and $R^4$ are linked such that —$R^3$—N—C(O)—$R^4$— forms part of a substituted or unsubstituted heterocyclic ring;
each of $R^5$ and $R^6$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or
$R^5$ and $R^6$ are linked such that —$R^5$—N—$R^6$— forms part of a substituted or unsubstituted heterocyclic ring;
Z is a linking group; and
n is any integer, which should be understood to encompass 0, 1, 2, 3 etc. Preferably, n is an integer of at least 1, such as 1, 2, 3 or 4, especially 1, 2 or 3, more especially 1 or 2. In one aspect, n is 1 and in another aspect n is 2. Where n is 0 this is intended to represent embodiments of the present invention where no linking group, Z, is present and the two nitrogen atoms (bonded to $R^1$ and $R^3$) are bonded directly to one another.

In another preferred embodiment of the present invention the polar group, P, is a substituted or unsubstituted inverse amido group (—N($R^3$)—C(O)—) and $R^{18}$ is represented by $R^4$, so as to provide a compound of formula (I) having the formula (Ib):

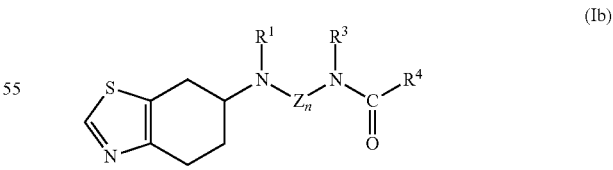

(Ib)

wherein
$R^1$ is as defined above;
each of $R^3$ and $R^4$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^5R^6$, or $R^3$ and $R^4$ are linked such that —$R^3$—N—C(O)—$R^4$— forms part of a substituted or unsubstituted heterocyclic ring;

each of $R^5$ and $R^6$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^5$ and $R^6$ are linked such that —$R^5$—N—$R^6$— forms part of a substituted or unsubstituted heterocyclic ring;

Z is a linking group; and n is any integer of 1 or more.

Preferably in the compounds of formula (Ib), n is 1, 2, 3 or 4, especially 1, 2 or 3, more especially 1 or 2. In one aspect, n is 1 and in another aspect n is 2.

With regard to the compounds of formula (Ib), Z may be selected from the group consisting of substituted or unsubstituted alkylene, substituted or unsubstituted alkenylene, substituted or unsubstituted alkynylene, substituted or unsubstituted carbocyclic ring, and substituted or unsubstituted heterocyclic ring. Preferably, Z may be selected from the group consisting of substituted or unsubstituted alkylene and substituted or unsubstituted carbocyclic ring.

Preferably in the compounds of formula (Ib) Z is a substituted or unsubstituted alkylene group. Said alkylene group may be a $C_1$-$C_6$, especially a $C_1$-$C_4$, more especially a $C_2$-$C_4$, substituted or unsubstituted alkylene group. Alternatively, said alkylene group is selected from the group consisting of methylene, ethylene, propylene, iso-propylene, butylene, iso-butylene and tert-butylene, especially from the group consisting of ethylene, propylene and butylene.

Preferably in the compounds of formula (Ib), n may be 1 and Z may be a substituted or unsubstituted alkylene group (such as a $C_1$-$C_6$, especially a $C_1$-$C_4$, more especially a $C_2$-$C_4$, substituted or unsubstituted alkylene group). For example, n may be 1 and Z may be selected from the group consisting of methylene, ethylene, propylene, iso-propylene, butylene, iso-butylene and tert-butylene, especially from the group consisting of ethylene, propylene and butylene.

The compound of formula (Ib) more preferably has the formula:

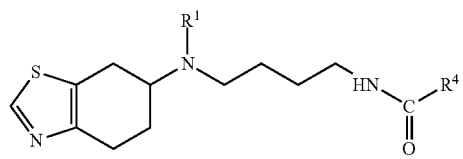

wherein each of $R^1$ and $R^4$ is as defined herein.

In the compounds of formula (Ib) $R^1$ may be selected from the group consisting of H and a substituted or unsubstituted alkyl, alkenyl or alkynyl group. For example, $R^1$ may contain 1 to 10 carbon atoms, more preferably 1 to 8 carbon atoms. $R^1$ may especially be selected from the group consisting of H and a $C_1$-$C_4$ substituted or unsubstituted alkyl, alkenyl or alkynyl group, for example from a group consisting of H, methyl, ethyl, propyl, allyl, prop-2-ynyl and but-2-ynyl.

In the compounds of formula (Ib) $R^4$ may be selected from the group consisting of substituted or unsubstituted alkenyl, substituted or unsubstituted carbocyclic ring, substituted or unsubstituted heterocyclic ring, and —$NR^5R^6$ where $R^5$ and $R^6$ are as defined above.

With regard to the compound of formula (Ib) $R^4$ is preferably a $C_2$-$C_4$ substituted or unsubstituted alkenyl group.

In the compound of formula (Ib), $R^4$ may be a substituted or unsubstituted aromatic carbocyclic ring containing any desirable number of carbon atoms. It is particularly preferred that $R^4$ contains 6 to 10 carbon atoms. The or each non-aromatic ring may contain 3 to 12 carbon atoms, more preferably 5 to 7 carbon atoms, arranged in a mono- or poly-cyclic arrangement. The or each aromatic ring may contain 6 to 12 carbon atoms, more preferably 6 to 8 carbon atoms, in a mono- or poly-cyclic arrangement. $R^4$ may be a substituted or unsubstituted phenyl ring or a substituted or unsubstituted naphthyl ring. Alternatively, $R^4$ may be a $C_4$-$C_{10}$ substituted or unsubstituted carbocyclic non-aromatic ring. In which case, $R^4$ is preferably a substituted or unsubstituted cyclopentyl ring or a substituted or unsubstituted cyclohexyl ring. As a still further preferred alternative where $R^4$ is a carbocyclic ring, $R^4$ may incorporate one or more aromatic and non-aromatic rings, which may be linked via one or more non-ring atoms, or may be linked via one or more ring atoms such that the rings are connected by via a fused, bridged or Spiro configuration. In a preferred embodiment $R^4$ is a substituted or unsubstituted adamantyl group. In a further preferred embodiment, $R^4$ has the formula:

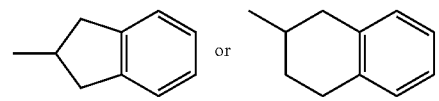

$R^4$ is a substituted or unsubstituted heterocyclic aromatic or non-aromatic ring. $R^4$ may be a substituted or unsubstituted benzothiazolyl group. In a more preferred embodiment $R^4$ has the formula:

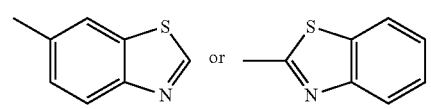

Alternatively $R^4$ may be selected from the group consisting of substituted or unsubstituted pyrrole, substituted or unsubstituted thiophene and substituted or unsubstituted furan. In a particularly preferred embodiment $R^4$ is substituted or unsubstituted benzothiophene.

$R^4$ may be a substituted or unsubstituted thiazole. For example, in a preferred embodiment $R^4$ has the formula:

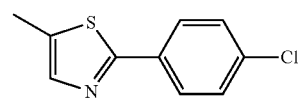

In a still further preferred embodiment $R^4$ is an amino group, —$NR^8R^9$, and one of $R^8$ and $R^9$ is H. Additionally or alternatively, $R^4$ may be —$NR^8R^9$ and one of $R^8$ and $R^9$ is a substituted or unsubstituted carbocyclic or heterocyclic aromatic or non-aromatic ring. Most preferably $R^9$ is a substituted or unsubstituted carbocyclic non-aromatic ring.

$R^4$ preferably has the formula:

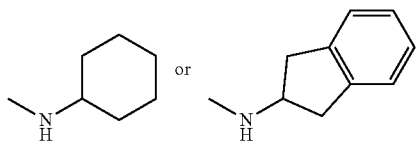 or 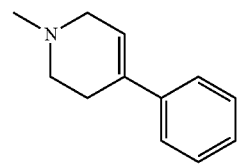

Alternatively, $R^4$ may be —$NR^8R^9$ and $R^8$ and $R^9$ are linked such that —$R^8$—N—$R^9$— forms part of a substituted or unsubstituted ring, such as a 5 to 12-membered ring, more preferably a 5 to 7-membered ring. $R^8$ and $R^9$ may be linked such that —$R^8$—N—$R^9$— forms part of a substituted or unsubstituted piperidine ring. Said piperidine ring may be substituted with any desirable group, such as a carbocyclic ring (e.g. a substituted or unsubstituted phenyl group) or a further heterocyclic ring.

In a further preferred embodiment $R^4$ has the formula:

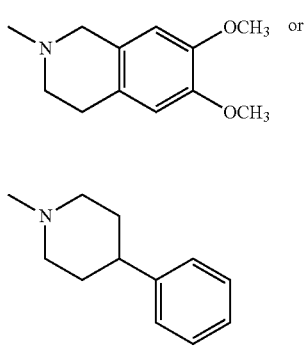

In an embodiment where $R^4$ is —$NR^8R^9$, and $R^8$ and $R^9$ may be linked such that —$R^8$—N—$R^9$— forms part of a substituted or unsubstituted pyrrolidine ring. $R^4$ may have the formula:

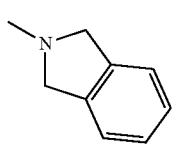

Alternatively $R^8$ and $R^9$ may be linked such that —$R^8$—N—$R^9$— forms part of a substituted or unsubstituted piperazine ring. The piperazine ring may be substituted with a substituted or unsubstituted phenyl group. For example, $R^4$ may have the formula:

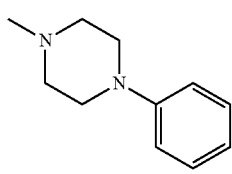

As a further preferred alternative $R^4$ may have the formula:

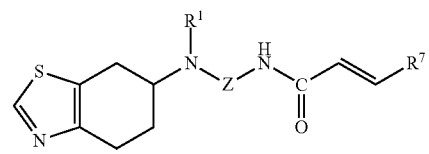

The compound of formula (Ib) may also have the formula:

wherein $R^7$ is a substituted or unsubstituted carbocyclic ring or a substituted or unsubstituted heterocyclic ring and $R^1$ and Z are as defined above.

$R^7$ may be a substituted or unsubstituted phenyl group. Preferably $R^7$ is a phenyl group substituted with one or more halogen atoms.

A further aspect of the invention provides any one or more compounds of formula (Ib) selected from:

N-{4-[Propyl-(4,5,6,7-tetrahydro-benzothiazol-6-yl)-amino]-butyl}-benzamide;
Naphthalene-2-carboxylic acid [4-(4,5,6,7-tetrahydro-benzothiazol-6-ylamino)-butyl]amide;
Naphthalene-2-carboxylic acid {4-[methyl-(4,5,6,7-tetrahydro-benzothiazol-6-yl)-amino]-butyl}-amide;
Naphthalene-2-carboxylic acid {4-[ethyl-(4,5,6,7-tetrahydro-benzothiazol-6-yl)-amino]-butyl}-amide;
Naphthalene-2-carboxylic acid {4-[propyl-(4,5,6,7-tetrahydro-benzothiazol-6-yl)-amino]-butyl}-amide;
Naphthalene-2-carboxylic acid {4-[allyl-(4,5,6,7-tetrahydro-benzothiazol-6-yl)-amino]-butyl}-amide;
Naphthalene-2-carboxylic acid {4-[prop-2-ynyl-(4,5,6,7-tetrahydro-benzothiazol-6-yl)-amino]-butyl}-amide;
Naphthalene-2-carboxylic acid {4-[but-2-ynyl-(4,5,6,7-tetrahydro-benzothiazol-6-yl)-amino]-butyl}-amide;
Benzo[b]thiophene-2-carboxylic acid [4-(4,5,6,7-tetrahydro-benzothiazol-6-ylamino)-butyl]-amide;
Benzo[b]thiophene-2-carboxylic acid {4-[methyl-(4,5,6,7-tetrahydro-benzothiazol-6-yl)-amino]-butyl}-amide;
Benzo[b]thiophene-2-carboxylic acid {4-[ethyl-(4,5,6,7-tetrahydro-benzothiazol-6-yl)-amino]-butyl}-amide;
Benzo [b]thiophene-2-carboxylic acid {4-[propyl-(4,5,6,7-tetrahydro-benzothiazol-6-yl)-amino]-butyl}-amide;
Benzothiazole-6-carboxylic acid {4-[ethyl-(4,5,6,7-tetrahydro-benzothiazol-6-yl)-amino]-butyl}-amide;
Benzothiazole-6-carboxylic acid {4-[propyl-(4,5,6,7-tetrahydro-benzothiazol-6-yl)-amino]-butyl}-amide;
N-{4-[Propyl-(4,5,6,7-tetrahydro-benzothiazol-6-yl)-amino]-butyl}-cinnamoylamide;
2,4-Dichloro-N-{4-[propyl-(4,5,6,7-tetrahydro-benzothiazol-6-yl)-amino]-butyl}-cinnamoylamide;
4-Fluoro-N-{4-[propyl-(4,5,6,7-tetrahydro-benzothiazol-6-yl)-amino]-butyl}-cinnamoylamide;
2-(4-Chloro-phenyl)-thiazole-5-carboxylic acid {4-[propyl-(4,5,6,7-tetrahydro-benzothiazol-6-yl)-amino]-butyl}-amide;

Cyclohexanecarboxylic acid {4-[propyl-(4,5,6,7-tetrahydro-benzothiazol-6-yl)-amino]-butyl}-amide;
Piperidine-1-carboxylic acid {4-[propyl-(4,5,6,7-tetrahydro-benzothiazol-6-yl)-amino]-butyl}-amide;
1-Cyclohexyl-3-{4-[propyl-(4,5,6,7-tetrahydro-benzothiazol-6-yl)-amino]-butyl}-urea;
1,2,3,4-Tetrahydro-naphthalene-2-carboxylic acid {4-[propyl-(4,5,6,7-tetrahydro-benzothiazol-6-yl)-amino]-butyl}-amide;
3,4-Dihydro-1H-isoquinoline-2-carboxylic acid {4-[propyl-(4,5,6,7-tetrahydro-benzothiazol-6-yl)-amino]-butyl}-amide;
6,7-Dimethoxy-3,4-dihydro-1H-isoquinoline-2-carboxylic acid {4-[propyl-(4,5,6,7-tetrahydro-benzothiazol-6-yl)-amino]-butyl}-amide;
Indane-2-carboxylic acid-{4-[propyl-(4,5,6,7-tetrahydrobenzothiazol-6-yl)amino]butyl}amide;
1,3-Dihydro-isoindole-2-carboxylic acid {4-[propyl-(4,5,6,7-tetrahydro-benzothiazol-6-yl)-amino]-butyl}-amide;
Naphthalene-2-carboxylic acid {2-[ethyl-(4,5,6,7-tetrahydro-benzothiazol-6-yl)-amino]-ethyl}-amide;
1-Indan-2-yl-3-4-[propyl-(4,5,6,7-tetrahydrobenzothiazol-6-yl)amino]butyl}urea;
4-Phenylpiperazine-1-carboxylic acid {4-[propyl-(4,5,6,7-tetrahydrobenzothiazol-6-yl)amino]butyl}amide;
4-Phenyl-3,6-dihydro-2H-pyridine-1-carboxylic acid {4-[propyl-(4,5,6,7-tetrahydrobenzothiazol-6-yl)amino]butyl}amide;
N-(4-(4,5,6,7-Tetrahydrobenzo[d]thiazol-6-ylamino)butyl)benzo[d]thiazole-2-carboxamide;
4-phenyl-N-(4-(propyl-(4,5,6,7-tetrahydrobenzo[d]thiazol-6-yl)amino)butyl)piperidine-1-carboxamide; and
N-(4-Propyl-(4,5,6,7-tetrahydrobenzothiazol-6-yl)butyl-adamantyl-1-carboxamide;
and pharmaceutically-acceptable salts thereof.

A further aspect of the present invention provides compound (1), synthesized below in Example A1, having the formula:

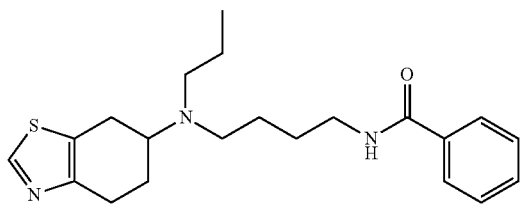

(1)

A further aspect of the present invention provides compound (15), synthesized below in Example A14, having the formula:

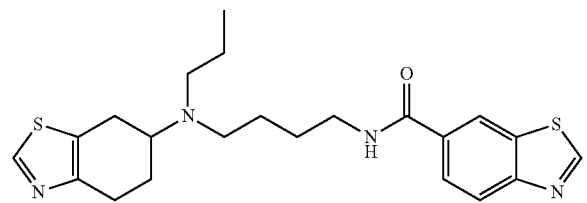

(15)

A further aspect of the present invention provides compound (12), synthesized below in Example A11, having the formula:

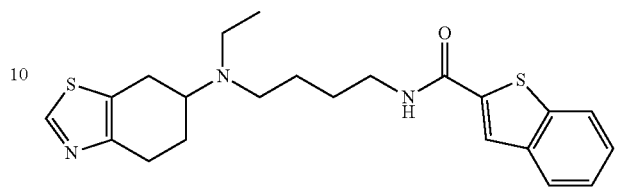

(12)

In a preferred embodiment of the present invention the polar group, P, is a substituted or unsubstituted amido (or carboxamido) group (—C(O)—N($R^{11}$)—) and $R^{18}$ is represented by $R^{10}$, so as to provide a compound of formula (I) having the formula (Ic):

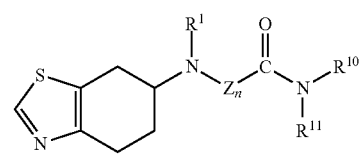

(Ic)

wherein $R^1$ is as defined above;

each of $R^{10}$ and $R^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —N$R^{12}R^{13}$, or $R^{10}$ and $R^{11}$ are linked such that —$R^{10}$—N—$R^{11}$— forms part of a substituted or unsubstituted heterocyclic ring;

each of $R^{12}$ and $R^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{12}$ and $R^{13}$ are linked such that —$R^{12}$—N—$R^{13}$— forms part of a substituted or unsubstituted heterocyclic ring;

Z is a linking group; and n is any integer, which should be understood to encompass 0, 1, 2, 3 etc. Preferably, n is an integer of at least 1, such as 1, 2, 3 or 4, especially 1, 2 or 3, more especially 1 or 2. In one aspect, n is 1 and in another aspect n is 2. Where n is 0 this is intended to represent embodiments of the present invention where no linking group, Z, is present and the two nitrogen atoms (bonded to $R^1$ and $R^{10}$) are bonded directly to one another.

In another preferred embodiment of the present invention the polar group, P, is a substituted or unsubstituted amido group (—C(O)—N($R^{11}$)—) and $R^{18}$ is represented by $R^{10}$, so as to provide a compound of formula (I) having the formula (Ic):

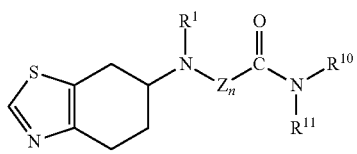

(Ic)

wherein
R$^1$ is as defined above;
each of R$^{10}$ and R$^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^{12}$R$^{13}$, or R$^{10}$ and R$^{11}$ are linked such that —R$^{10}$—N—R$^{11}$— forms part of a substituted or unsubstituted heterocyclic ring;
each of R$^{12}$ and R$^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or R$^{12}$ and R$^{13}$ are linked such that —R$^{12}$—N—R$^{13}$— forms part of a substituted or unsubstituted heterocyclic ring;
Z is a linking group; and
n is any integer of 1 or more.

Preferably in the compounds of formula (Ic), n is 1, 2, 3 or 4, especially 1, 2 or 3, more especially 1 or 2. In one aspect, n is 1 and in another aspect n is 2.

Preferably, in the compounds of formula (Ic) R$^1$ may be selected from the group consisting of a substituted or unsubstituted alkyl, alkenyl or alkynyl group. For example, R$^1$ may contain 1 to 10 carbon atoms, more preferably 1 to 8 carbon atoms. R$^1$ may especially be a substituted or unsubstituted alkyl group, for example a C$_1$-C$_4$ substituted or unsubstituted alkyl group (such as methyl, ethyl or propyl, especially propyl).

In the compounds of formula (Ic), Z may be selected from the group consisting of substituted or unsubstituted alkylene, substituted or unsubstituted alkenylene, substituted or unsubstituted alkynylene, substituted or unsubstituted carbocyclic ring, and substituted or unsubstituted heterocyclic ring. For example, Z may be selected from the group consisting of substituted or unsubstituted alkylene and substituted or unsubstituted carbocyclic ring.

Preferably in the compounds of formula (Ic), n may be 1 or 2 and Z may be selected from the group consisting of substituted or unsubstituted alkylene and substituted or unsubstituted carbocyclic ring. For example, in one aspect, n may be 1 and Z may be a substituted or unsubstituted alkylene group (such as a C$_1$-C$_6$, especially a C$_1$-C$_4$, more especially a C$_2$-C$_4$, substituted or unsubstituted alkylene group). More particularly, n may be 1 and Z may be selected from the group consisting of methylene, ethylene, propylene, iso-propylene, butylene, iso-butylene and tert-butylene, especially Z may be butylene. In another aspect, n may be 2 and Z may be selected from the group consisting of substituted or unsubstituted alkylene and substituted or unsubstituted carbocyclic ring. For example, n may be 2 and one Z group may be a substituted or unsubstituted alkylene group (such as a C$_1$-C$_4$ substituted or unsubstituted alkylene group, especially a methylene group) and the other Z group may be a substituted or unsubstituted carbocyclic ring (such as phenyl ring).

A preferred compound according to formula (Ic) may have the formula:

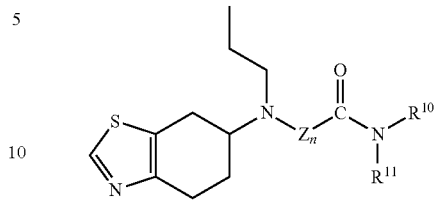

where Z, n, R$^{10}$ and R$^{11}$ are as defined herein.

Preferably in the compounds of formula (Ic) Z is a substituted or unsubstituted alkylene group. Said alkylene group may be a C$_1$-C$_6$ substituted or unsubstituted alkylene group. Alternatively, said alkylene group is selected from the group consisting of methylene, ethylene, propylene, iso-propylene, butylene, iso-butylene and tert-butylene.

A preferred compound of formula (Ic) may have the formula:

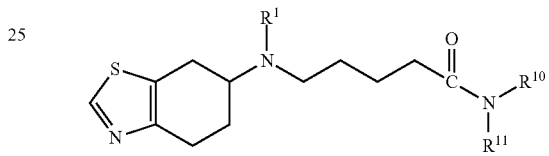

wherein each of R$^1$, R$^{10}$ and R$^{11}$ is as defined herein.

Preferably in the compounds of formula (Ic) Z may be a substituted or unsubstituted (hetero)arylene group. Said (hetero)arylene group may be a C$_6$-C$_{10}$ substituted or unsubstituted (hetero)arylene group. Said (hetero)arylene group may be selected from the group consisting of phenylene, benzylene, tolylene, and xylylene. Said compounds of formula (Ic) may have the formula:

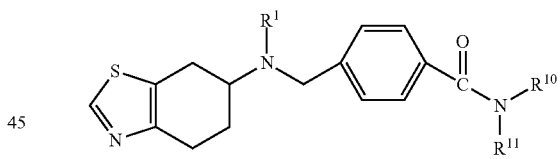

wherein each of R$^1$, R$^{10}$ and R$^{11}$ is as defined herein.

It is preferred that a first one of R$^{10}$ and R$^{11}$ is H. Additionally or alternatively, a second one of R$^{10}$ and R$^{11}$ may be selected from the group consisting of substituted or unsubstituted alkyl, substituted or unsubstituted carbocyclic aromatic or non-aromatic ring, and substituted or unsubstituted heterocyclic aromatic or non-aromatic ring.

Preferably said second one of R$^{10}$ and R$^{11}$ is a C$_1$-C$_4$ substituted or unsubstituted alkyl group, which may be selected from the group consisting of methyl, ethyl, propyl, iso-propyl, butyl, iso-butyl and tert-butyl.

Alternatively said second one of R$^{10}$ and R$^{11}$ may be selected from the group consisting of a substituted or unsubstituted monocyclic carbocyclic ring, a substituted or unsubstituted bicyclic carbocyclic ring and a substituted or unsubstituted tricyclic carbocyclic ring, for example an adamantanyl group.

Said second one of R$^{10}$ and R$^{11}$ may be a C$_8$-C$_{14}$ substituted or unsubstituted bicyclic carbocyclic ring, such as a naphthyl group.

It is particularly preferred that said second one of $R^{10}$ and $R^{11}$ has the formula:

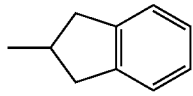

As a still further alternative, said second one of $R^{10}$ and $R^{11}$ is selected from the group consisting of a substituted or unsubstituted monocyclic heterocyclic ring, a substituted or unsubstituted bicyclic heterocyclic ring and a substituted or unsubstituted tricyclic heterocyclic ring. A preferred option in this regard is a tetrahydro-benzothiazole group.

Alternatively, $R^{10}$ and $R^{11}$ may be linked to form part of a substituted or unsubstituted piperazine ring, which may be a 4N-substituted piperazine ring.

A further aspect of the invention provides any one or more compounds of formula (Ic) selected from:
5-[Propyl-(4,5,6,7-tetrahydro-benzothiazol-6-yl)-amino]-pentanoic acid naphthalen-2-ylamide;
N-Propyl-4-{[propyl-(4,5,6,7-tetrahydrobenzothiazol-6-yl)amino]methyl}-N-(4,5,6,7-tetrahydrobenzothiazol-6-yl)benzamide;
(4-Phenylpiperazin-1-yl)-(4-{[propyl-(4,5,6,7-tetrahydrobenzothiazol-6-yl)amino]methyl}phenyl)methanone;
N-Indan-2-yl-4-{[propyl-(4,5,6,7-tetrahydrobenzothiazol-6-yl)amino]methyl}benzamide;
1-(4-Phenylpiperazin-1-yl)-5-(propyl-(4,5,6,7-tetrahydrobenzothiazol-6-yl)amino)pentan-1-one;
N-(2,3-dihydro-1H-inden-2-yl)-5-(propyl-(4,5,6,7-tetrahydrobenzothiazol-6-yl)amino)pentanamide; and
N-Adamantanyl-5-(propyl-(4,5,6,7-tetrahydrobenzothiazol-6-yl)amino)pentanamide;
and pharmaceutically-acceptable salts thereof.

A preferred example of a compound of formula (Ic) has the formula:

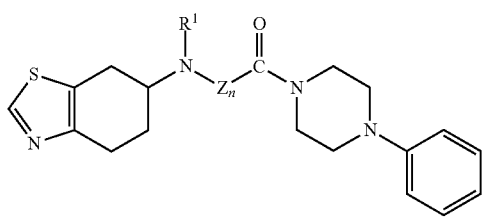

A further aspect of the present invention provides a compound (68), synthesized as set out below in Example B7, having the formula:

(68)

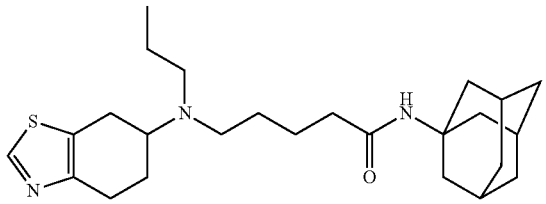

A further aspect of the present invention provides a compound (66), synthesized as set out below in Example B5, having the formula:

(66)

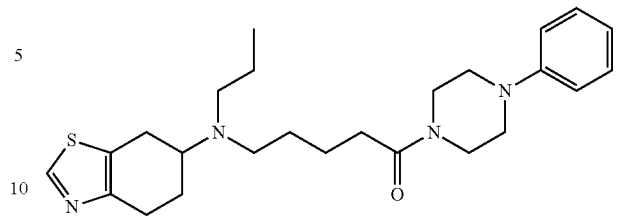

A further aspect of the present invention provides a compound (67), synthesized as set out below in Example B6, having the formula:

(67)

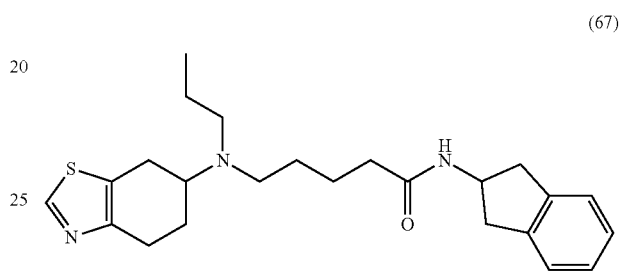

In a preferred embodiment of the present invention the polar group, P, is a substituted or unsubstituted amino group (—N($R^{15}$)—) and $R^{18}$ is represented by $R^{14}$, so as to provide a compound of formula (I) having the formula (Id):

(Id)

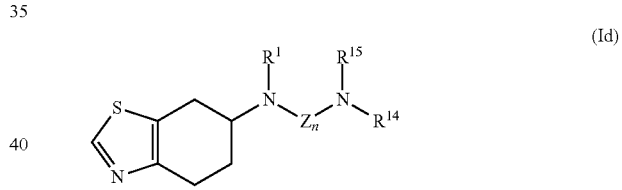

wherein
$R^1$ is as defined above;
each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{16}R^{17}$, or
$R^{14}$ and $R^{15}$ are linked such that —$R^{14}$—N—$R^{15}$— forms part of a substituted or unsubstituted heterocyclic ring;
each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or
$R^{16}$ and $R^{17}$ are linked such that —$R^{16}$—N—$R^{17}$— forms part of a substituted or unsubstituted heterocyclic ring;
Z is a linking group; and
n is any integer, which should be understood to encompass 0, 1, 2, 3 etc. Preferably, n is an integer of at least 1, such as 1, 2, 3 or 4, especially 1, 2 or 3, more especially 1 or 2. In one aspect, n is 1 and in another aspect n is 2. Where n is 0 this is intended to represent embodiments of the present invention where no linking group, Z, is present and the two nitrogen atoms (bonded to $R^1$ and $R^{14}$) are bonded directly to one another.

In another preferred embodiment of the present invention the polar group, P, is a substituted or unsubstituted amino group (—N($R^{15}$)—) and $R^{18}$ is represented by $R^{14}$, so as to provide a compound of formula (I) having the formula (Id):

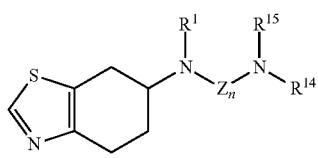
(Id)

wherein
$R^1$ is as defined above;
each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{16}R^{17}$, or
$R^{14}$ and $R^{15}$ are linked such that —$R^{14}$—N—$R^{15}$— forms part of a substituted or unsubstituted heterocyclic ring;
each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or
$R^{16}$ and $R^{17}$ are linked such that —$R^{16}$—N—$R^{17}$— forms part of a substituted or unsubstituted heterocyclic ring;
Z is a linking group; and
n is any integer of 1 or more.

Preferably in the compounds of formula (Id), n is 1, 2, 3 or 4, especially 1, 2 or 3, more especially 1 or 2. In one aspect, n is 1 and in another aspect n is 2.

Preferably, in the compounds of formula (Id) $R^1$ may be selected from the group consisting of a substituted or unsubstituted alkyl, alkenyl or alkynyl group. For example, $R^1$ may contain 1 to 10 carbon atoms, more preferably 1 to 8 carbon atoms. $R^1$ may especially be a substituted or unsubstituted alkyl group, for example a $C_1$-$C_4$ substituted or unsubstituted alkyl group (such as methyl, ethyl or propyl, especially ethyl or propyl).

In the compounds of formula (Id), it is preferred that Z is selected from the group consisting of substituted or unsubstituted alkylene, substituted or unsubstituted alkenylene, substituted or unsubstituted alkynylene, substituted or unsubstituted carbocyclic ring, and substituted or unsubstituted heterocyclic ring. For example, Z may be substituted or unsubstituted alkylene.

Preferably in the compounds of formula (Id), n may be 1 and Z may be a substituted or unsubstituted alkylene group (such as a $C_1$-$C_6$, especially a $C_1$-$C_4$, more especially a $C_2$-$C_4$, substituted or unsubstituted alkylene group). For example, n may be 1 and Z may be selected from the group consisting of methylene, ethylene, propylene, iso-propylene, butylene, iso-butylene and tert-butylene, especially from the group consisting of ethylene, propylene and butylene.

Preferably in the compounds of formula (Id), each of $R^{14}$ and $R^{15}$ is separately selected from the group consisting of substituted or unsubstituted alkyl, substituted or unsubstituted alkenyl, substituted or unsubstituted alkynyl and substituted or unsubstituted heterocyclic ring, or $R^{14}$ and $R^{15}$ are linked such that —$R^{14}$—N—$R^{15}$— forms part of a substituted or unsubstituted heterocyclic ring. More preferably, in the compounds of formula (Id), each of $R^{14}$ and $R^{15}$ is separately selected from the group consisting of substituted or unsubstituted alkyl and substituted or unsubstituted heterocyclic ring, or $R^{14}$ and $R^{15}$ are linked such that —$R^{14}$—N—$R^{15}$— forms part of a substituted or unsubstituted heterocyclic ring.

The compound according to formula (Id) may have the formula:

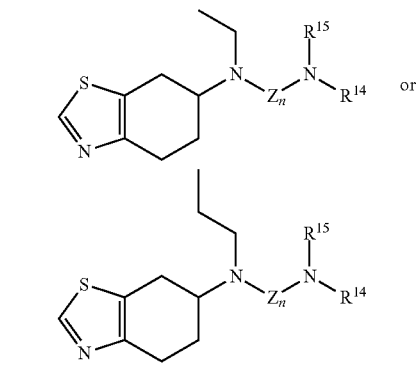

wherein each of Z, n, $R^{14}$ and $R^{15}$ is as defined herein.

Preferably, in the compounds of formula (Id), Z is a substituted or unsubstituted alkylene group, for example a $C_1$-$C_6$, especially a $C_1$-$C_4$, more especially a $C_2$-$C_4$, substituted or unsubstituted alkylene group, which may be selected from the group consisting of methylene, ethylene, propylene, iso-propylene, butylene, iso-butylene and tert-butylene (such as ethylene, propylene and butylene).

Another preferred example of a compound of formula (Id) has the formula:

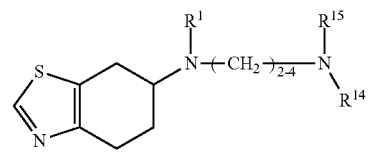

wherein each of $R^1$, $R^{14}$ and $R^{15}$ is as defined herein.

One of $R^{14}$ and $R^{15}$ is preferably a $C_1$-$C_4$ substituted or unsubstituted alkyl group, such as a methyl, ethyl, propyl or butyl group (especially an ethyl group).

One of $R^{14}$ and $R^{15}$ may be selected from the group consisting of a substituted or unsubstituted monocyclic heterocyclic ring, a substituted or unsubstituted bicyclic heterocyclic ring and a substituted or unsubstituted tricyclic heterocyclic ring. A preferred example of which is a tetrahydro-benzothiazole group.

$R^{14}$ and $R^{15}$ may be linked to form part of a substituted or unsubstituted piperazine ring, which may be a 4N-substituted piperazine ring. The 4N-substituent may comprise a substituted or unsubstituted aromatic group, which is optionally substituted with a substituent selected from the group consisting of an alkoxyl group and a halo group. Said aromatic group may be substituted with an ortho-methoxyl group, or ortho- and meta-halo groups. Alternatively or additionally the 4N-substituent may comprise a carbonyl group, which may be bonded to a substituted or unsubstituted aromatic group.

Said aromatic group is preferably selected from the group consisting of phenyl and naphthyl.

Alternatively $R^{14}$ and $R^{15}$ may be linked to form part of a substituted or unsubstituted piperidine ring, which is optionally connected to an aromatic group. By way of example, the compound of formula (Id) may have the formula:

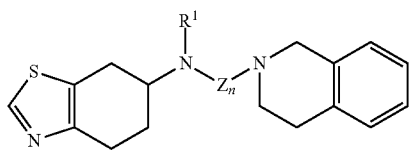

wherein each of $R^1$, Z and n is as defined herein.

As a still further preferred alternative $R^1$ and $R^{15}$ may be linked to form part of the same heterocyclic aromatic or non-aromatic ring. Preferably $R^1$ and $R^{15}$ are linked to form part of a substituted or unsubstituted piperazine ring. $R^{14}$ may be a substituted or unsubstituted $C_1$-$C_4$ alkyl group.

A further aspect of the invention provides any one or more compounds of formula (Id) selected from:
Ethyl-{2-[4-(2-methoxy-phenyl)-piperazin-1-yl]-ethyl}-(4,5,6,7-tetrahydro-benzothiazol-6-yl)-amine;
Ethyl-{3-[4-(2-methoxy-phenyl)-piperazin-1-yl]-propyl}-(4,5,6,7-tetrahydro-benzothiazol-6-yl)-amine;
Ethyl-{4-[4-(2-methoxy-phenyl)-piperazin-1-yl]-butyl -(4,5,6,7-tetrahydro-benzothiazol-6-yl)-amine;
[2-(3,4-Dihydro-1H-isoquinolin-2-yl)-ethyl]-ethyl-(4,5,6,7-tetrahydro-benzothiazol-6-yl)-amine;
N,N'-Diethyl-N,N'-bis-(4,5,6,7-tetrahydro-benzothiazol-6-yl)-ethane-1,2-diamine;
{2-[4-(2-Methoxy-phenyl)-piperazin-1-yl]-ethyl}-propyl-(4,5,6,7-tetrahydro-benzothiazol-6-yl)-amine;
{2-[4-(2,3-Dichloro-phenyl)-piperazin-1-yl]-ethyl}-propyl-(4,5,6,7-tetrahydro-benzothiazol-6-yl)-amine;
{3-[4-(2,3-Dichloro-phenyl)-piperazin-1-yl]-propyl}-propyl-(4,5,6,7-tetrahydro-benzothiazol-6-yl)-amine;
{4-[4-(2,3-Dichloro-phenyl)-piperazin-1-yl]-butyl}-propyl-(4,5,6,7-tetrahydro-benzothiazol-6-yl)-amine;
[2-(4-Benzoyl-piperazin-1-yl)-ethyl]-propyl-(4,5,6,7-tetrahydro-benzothiazol-6-yl)-amine; and
[2-(4-Naphthoyl-piperazin-1-yl)-ethyl]-propyl-(4,5,6,7-tetrahydro-benzothiazol-6-yl)-amine;
and pharmaceutically-acceptable salts thereof.

A still further aspect of the present invention provides a compound (28), synthesized according to Example C1 below, having the formula:

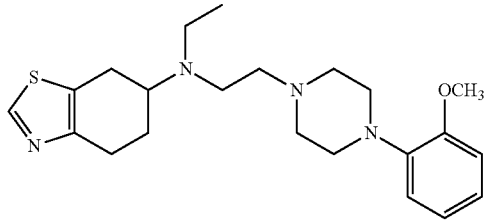

A still further aspect of the present invention provides a compound (33), synthesized according to Example C5 below, having the formula:

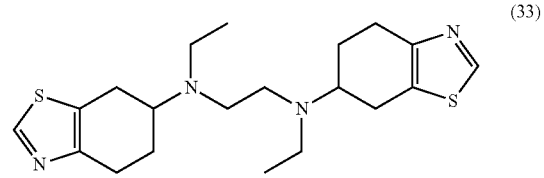 [SMILES: CCN(CCN(CC)C1CCc2ncsc2C1)C1CCc2ncsc2C1]

A still further aspect of the present invention provides a compound (34), synthesized according to Example C6 below, having the formula:

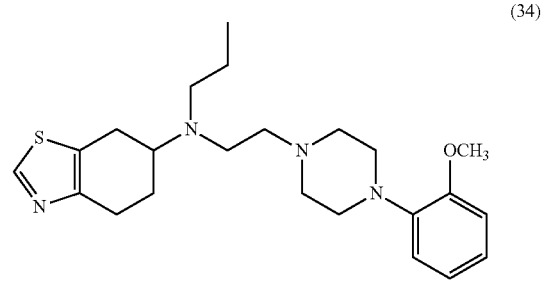 [SMILES: CCCN(CCN1CCN(c2ccccc2OC)CC1)C1CCc2ncsc2C1]

A still further aspect of the present invention provides a compound (38), synthesized according to Example C10 below, having the formula:

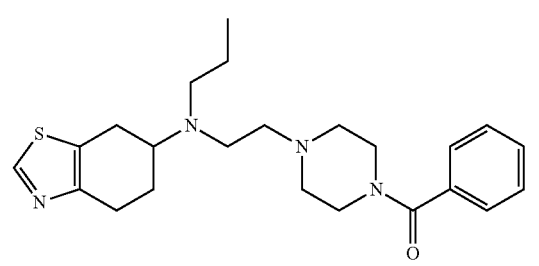

In a preferred embodiment of the present invention the polar group, P, is an oxy group (—O—) and $R^{18}$ is represented by $R^4$, so as to provide a compound of formula (I) having the formula (Ie):

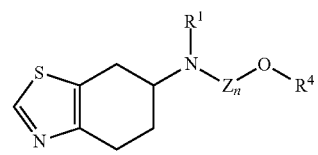

wherein
$R^1$ is as defined above;
$R^4$ is selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring and substituted or unsubstituted heterocyclic ring;
Z is a linking group; and
n is any integer of 1 or more.

Preferably in the compounds of formula (Ie), n is 1, 2, 3 or 4, especially 1, 2 or 3, more especially 1 or 2. In one aspect, n is 1 and in another aspect n is 2.

With regard to the compounds of formula (Ie), Z may be selected from the group consisting of substituted or unsubstituted alkylene, substituted or unsubstituted alkenylene, substituted or unsubstituted alkynylene, substituted or unsubstituted carbocyclic ring, and substituted or unsubstituted heterocyclic ring. Preferably, Z may be selected from the group consisting of substituted or unsubstituted alkylene and substituted or unsubstituted carbocyclic ring.

Preferably in the compounds of formula (Ie) Z is a substituted or unsubstituted alkylene group. Said alkylene group may be a $C_1$-$C_6$, especially a $C_1$-$C_4$, more especially a $C_2$-$C_4$, substituted or unsubstituted alkylene group. Alternatively, said alkylene group is selected from the group consisting of methylene, ethylene, propylene, iso-propylene, butylene, iso-butylene and tert-butylene, especially from the group consisting of ethylene, propylene and butylene.

Preferably in the compounds of formula (Ie), n may be 1 and Z may be a substituted or unsubstituted alkylene group (such as a $C_1$-$C_6$, especially a $C_1$-$C_4$, more especially a $C_2$-$C_4$, substituted or unsubstituted alkylene group). For example, n may be 1 and Z may be selected from the group consisting of methylene, ethylene, propylene, iso-propylene, butylene, iso-butylene and tert-butylene, especially from the group consisting of ethylene, propylene and butylene, most especially Z may be ethylene.

The compound of formula (Ie) more preferably has the formula:

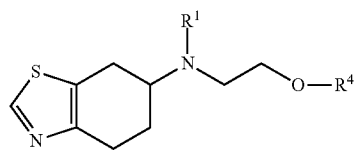

wherein each of $R^1$ and $R^4$ is as defined herein.

In the compounds of formula (Ie) $R^1$ may be selected from the group consisting of H and a substituted or unsubstituted alkyl, alkenyl or alkynyl group. For example, $R^1$ may contain 1 to 10 carbon atoms, more preferably 1 to 8 carbon atoms. $R^1$ may especially be a $C_1$-$C_4$ substituted or unsubstituted alkyl, alkenyl or alkynyl group, more especially a $C_1$-$C_4$ substituted or unsubstituted alkyl group (such as propyl).

In the compounds of formula (Ie) $R^4$ may be a substituted or unsubstituted carbocyclic ring, such as a phenyl ring.

A further aspect of the invention provides a compound (69), synthesized as set out below in Example D1, having the formula:

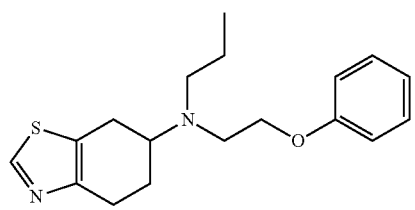

(69)

The compounds of the invention may be any diastereomer or enantiomer or racemate or racemic mixture or tautomeric form thereof including mixtures of these or a pharmaceutical acceptable salt thereof including different or special polymorphic forms.

Some of the compounds of the present invention are chiral and may have additional centres of asymmetry in the added moieties, and it is intended that any enantiomer and diastereomer, as separated, pure or partially purified enantiomers, diastereomers or racemic mixtures thereof are included within the scope of the invention. It will be appreciated that a skilled person may wish to select the single enantiomer with one of the highest potency and selectivity.

Furthermore, when a double bond or a fully or partially saturated ring system or more than one centre of asymmetry or a bond with restricted rotability is present in the molecule diastereomers may be formed. It is intended that any enantiomer, diastereomer or rotamer, as separated, pure or partially purified enantiomers, diastereomers or rotamers or mixtures thereof are included within the scope of the invention.

Some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable addition of salts, pharmaceutically acceptable metal salts, ammonium, and alkylated ammonium salts. Acid addition salts include salts of inorganic acids as well as organic acids. Representative examples of suitable inorganic salts include hydrochloric, hydrobromic, hydroiodic, phosphoric, sulfuric, nitric acids and the like. Representative examples of suitable organic acids include, formic, acetic, trichloroacetic, trifluoroacetic, propionic, benzoic, cinnamic, citric, fumaric, glycolic, lactic, maleic, malic, methansulfonic, ethansulfonic, aspartic, stearic, palmitic, EDTA, glycolic, glutamic, malonic, mandelic, oxalic, picric, salicylic, siccinic, sulfonic, gluconic, citraconic, tartaric, ascorbic, bismethylene salicylic, ethynditamic, benzene sulfonic, p-toluene sulfonic acids and the like. Further examples of pharmaceutically acceptable inorganic and organic acid addition salts include the pharmaceutically acceptable salts listed in e.g., S. M. Berge, L. D. Bighley, D. C. Monkhouse, J. Pharm. Sci. 1977, 66, 1-19, and P. H. Stahl, C: G: Wermuth, Handbook of pharmaceutical salts: Properties, selection and use. 2002, Verlag Helvetica Chimica Acta, Zürich; ISBN: 3-906390-26-8. Examples of metal salts include lithium, sodium, potassium, magnesium salts and the like. Examples of ammonium, alkylated ammonium salts include ammonium, methylammonium, dimethylammonium, trimethylammonium, ethylammonium, hydroxyethylammonium, diethylammonium, butylammonium, tetramethylammonium salt and the like.

Also intended as pharmaceutically acceptable acid addition are the hydrates, which the present compounds are able to form.

The acid addition may be obtained as direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weights solvents using methods well known to the person skilled in the art. Such solvates are contemplated as being within the scope of the present invention.

The invention also encompasses prodrugs of the present compounds, which on administration undergo chemical conversion by metabolic or chemical processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in Design of Prodrugs, ed. H. Bundgaard, Elsevier, 1985.

The invention also encompasses active metabolites of the present compounds. Such metabolites include those formed by chemical reactions a well as by enzymatic reactions in the body. The definition of active metabolites includes the formation of phase I as well as phase II metabolites as different conjugated derivatives.

The inventors have found that compounds of the present invention exhibit great affinity for dopamine receptors. Preferably, the compounds according to the invention bind to dopamine receptor subtypes with a $K_i$ value for binding of less than 10 µM, more preferred of less than 1 µM, and even more preferred of less than 500 nM, and most preferably of less than 100 nM. A skilled person will appreciate how to determine $K_i$ values for dopamine receptor binding and preferred methods are described in the Examples.

It is preferred that the compounds of the present invention have affinity for dopamine D3 or/and D2 receptors and are accordingly useful for the treatment and/or prevention of a wide variety of conditions and disorders in which dopamine D3 and/or Dopamine D2 receptor interactions are beneficial (as discussed above and below). It is most preferred that that the compounds of the present invention have affinity for dopamine D3 receptors and the abovementioned $K_i$ values apply to dopamine D3 receptor binding. It is more preferred that the compounds have affinity for and also show selectivity for D3 receptors.

It is preferred that the compounds have a greater affinity for D3 receptors than for D2 receptors. It is preferred that the compounds have at least a 10-fold selectivity for the D3 receptor over D2 receptors and more preferred that it has a 30-fold or 50-fold selectivity for the D3 receptor over D2 receptors. It is even more preferred that the compounds have a 100-fold or higher selectivity for the D3 receptor over D2 receptors.

Preferred compounds act as agonists of D3 receptors whereas other preferred compounds act as partial agonists, inverse agonists or antagonist of D3 receptors.

Compounds of the present invention, when compared to pramipexole or etrabamine, have improved pharmacokinetic properties and fewer side-effects. Preferred compounds have a faster onset when administered orally, or by the intra-peritoneal route, and have a maximal effect within the first 15 minutes after application (e.g. see the figures and particularly FIG. 1, 2, 5, 8, 11, 14 or 19 (corresponding to compounds 1, 15, 24, 25, 9, 67 and 39 respectively)). Other preferred compounds (e.g. see FIG. 12 corresponding to compound 68) have sustained activity over a number of hours following oral or intra-peritoneal application. For instance activity may be sustained over at least 1 hour, preferably over at least 2 hours and more preferably over at least 4 hours. Some preferred compounds have a rapid onset of activity and also have a sustained effect (e.g. see FIGS. 16 and 17 corresponding to Compounds 33 and 34).

It is also preferred that the compounds according to the invention are effective for inhibiting symptoms associated with medical conditions characterized by an imbalance in dopamine receptor activity such that $IC_{50}$ values are in the micromolar range. It is preferred that $IC_{50}$ values are less than 100 µM, preferably less than 10 µM, more preferably of less than 1 µM, and even more preferably of less than 500 nM, and most preferably of less than 100 nM. A skilled person will appreciate that a number of models exist for testing the efficacy of compounds for treating medical conditions characterized by an imbalance in dopamine receptor activity. For instance dose-response assessments may be based the in-vivo assays described in the Examples.

Compositions and Medicaments According to the Invention

The pharmaceutical composition according to the invention comprises, as an active ingredient, at least one compound of the present invention. The composition may comprise any diasteromer or enantiomer or tautomeric form of the compound and including mixtures of these or pharmaceutically acceptable salts thereof.

The pharmaceutical composition may comprise the compound of the present invention together with one or more pharmaceutically acceptable carriers or diluents.

The pharmaceutical composition should comprise a therapeutically effective amount of the compound of the invention. The exact amount required will depend upon the potency of the compound used. However in general terms the composition may comprise an amount from about 0.01 mg to about 800 mg of a compound according to the invention. In another embodiment, the amount is from about 0.01 mg to about 500 mg. When the compound is Compound 19 the amount may be an amount from about 0.01 mg to about 250 mg; preferably about 0.1 mg to about 60 mg; and more preferably about 1 mg to about 20 mg; and most preferably about 5 mg to about 10 mg.

The compounds of the invention may be formulated for administration alone or in combination with pharmaceutical acceptable carriers or excipients, in either single or multiple doses. The pharmaceutical compositions according to the invention may be formulated with pharmaceutical acceptable carriers or diluents as well as any other known adjuvants and excipients in accordance with conventional techniques such as those disclosed in Remington: The Science and Practice of Pharmacy, 19th Edition, Gennaro, Ed. Mack Publishing Co., Easton, Pa., 1995.

The pharmaceutical compositions may be specifically formulated for administration by any suitable route such as the oral, rectal, nasal, pulmonal, topical (incl. buccal and sublingual), transdermal, itracisternal, intraperitoneal, vaginal and parenteral (incl. subcutaneous, intramuscular, intrathecal, intravenous and intradermal) route. The oral and the transdermal routes are preferred and the oral route is most preferred. It will be appreciated that the preferred route will depend on the general condition and age of the subject to be treated, the nature of the condition to be treated and the active ingredient chosen.

In a preferred embodiment of the invention the compounds are formulated for oral administration. Thus, according to the present invention there is provided a pharmaceutical composition comprising a compound of the present invention and adapted for oral administration.

Pharmaceutical compositions for oral administration may be in a solid dosage form such as capsules, tablets, dragees, pills, lozenges, powders and granules. Solid dosage forms can include one or more substances which may also act as flavoring agents, lubricants, solubilizers, suspending agents, fillers, glidants, compression aids, binders or tablet-disintegrating agents. In powders, the vehicle is a finely divided solid which is in admixture with the finely divided compound according to the invention. In tablets, the compound according to the invention is mixed with a vehicle having the necessary compression properties in suitable proportions and compacted in the shape and size desired. The powders and tablets preferably contain up to 99% of the compound of the invention.

Suitable solid vehicles include, for example, calcium phosphate, magnesium stearate, talc, sugars, lactose, dextrin, starch, gelatin, cellulose, polyvinylpyrrolidine, low melting waxes and ion exchange resins. The amount of solid carrier will vary widely but will usually be from about 25 to about 1000 mg.

Where appropriate, solid dosage forms can be prepared with coatings such as enteric coatings or they can be formulated so as to provide controlled release of the active ingredient such as sustained or prolonged release or bolus application according to the methods well known in the art.

A typical tablet, which may be prepared by conventional tableting techniques (e.g. by compression), may contain:

| Core: | |
|---|---|
| Active compounds (as free compound or salt thereof) | 5.0 mg to 10.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, Tablet disintegrant, Rohm and Haas
**Acylated monoglyceride used as plasticizer for fil coating Pharmaceutical compositions for oral administration may alternatively be in a liquid form. A liquid carrier may be in the form of solutions, suspensions, emulsions, syrups, elixirs and pressurized compositions. The compound of the invention can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil).

In another embodiment of the invention the compounds are formulated for parenteral administration.

Preferably liquid compositions are used parenterally. When this is the case the liquid forms, and particularly the liquid vehicles discussed above may be used. Furthermore, for parenteral administration, the vehicle can also be an oily ester such as ethyl oleate and isopropyl myristate. Sterile liquid vehicles are useful in sterile liquid form compositions for parenteral administration.

Liquid pharmaceutical compositions that are sterile solutions or suspensions can be utilized for other preferred routes of administration. For example, liquids may be used for intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Vehicles include necessary and inert binders, suspending agents, lubricants, flavorants, sweeteners, preservatives, dyes, and coatings.

Other suitable administration forms include suppositories, sprays, ointments, cremes, gels, inhalates, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administration in one or more dosages such as one to three dosages. The exact dosage will depend upon the frequency and mode of application, the sex, age, weight and general condition of the subject treated, the nature and severity of the condition treated and any concomitant disease to be treated and other factors evident to those skilled in the art.

The pharmaceutical composition according to the invention may conveniently be presented in unit dosage form by methods known to those skilled in the art. A typical unit dosage form for oral administration one or more times per day, such as 1 to 3 times per day, contain 0.05 to about 1000 mg, preferably from about 0.1 to about 500 mg, more preferred from about 0.5 to about 3000 mg, more preferably about 10 to about 1000 mg, and most preferably about 10 to about 500 mg.

For parenteral routes, such as intravenous, intrathecal, intramuscular, intra-peritoneal and similar administration, typically doses are in the order of about half the dose employed for oral administration.

The compounds of the invention are generally utilized as the free substance or as a pharmaceutically acceptable salt thereof. One example is an acid addition salt of a compound having the utility of a free base. When a compound of the present invention contains a free base such salts are prepared in a conventional manner by treating a solution or suspension of a free base of the present invention with a chemical equivalent of a pharmaceutical acceptable acid, for example inorganic or organic acids. Representative examples are mentioned above. Physiologically acceptable salts of a compound with a hydroxyl group include the anion of said compound in combination with a suitable cation such as sodium or ammonium ion.

For parenteral administration, solutions of the novel compounds of the present invention in sterile aqueous or non-aqueous solution, aqueous propylene glycol or sesame or peanut oil may be employed. Such aqueous solutions should be buffered if necessary and the liquid diluted first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glycerol monostearate or glycerol distearate, alone or mixed with wax.

The pharmaceutical compositions formed by combining the novel compounds of the present invention and the pharmaceutical acceptable carriers are then readily administered in a variety of dosage forms suitable for the disclosed routes of administration. The formulations may conveniently be presented in unit dosage form by methods known in the art of pharmacy.

Formulations of pharmaceutical compositions according to the present invention suitable for oral administration may be presented as discrete units such as capsules or tablets, each containing a predetermined amount of the active ingredient, and which may include a suitable excipient. These formulations may be in the form of powder or granules or melted solution, as a solution or suspension in an aqueous solution or non-aqueous liquid, or as an oil-in-water or water-in-oil emulsion.

If desired, the pharmaceutical composition of the invention may comprise a compound according to the invention in combination with one or more pharmacologically active substances (e.g. prior art agents used in the treatment of movement disorders).

Uses of Compounds, Compositions and Medicaments According to the Invention

A skilled person will appreciate that many conditions are associated with an imbalance in dopamine receptor activity. Such conditions may be treated according to aspects of the invention.

The compounds may used to treat conditions such as parkinsonism, dyskinesia, schizophrenia, addiction, sexual dysfunction, bipolar disorder, attention deficit hyperactivity disorder (ADHD), Tourette's syndrome, depression, anxiety, cognitive impairment (e.g. Alzheimer's disease), dementia, emesis, nausea, amnesia, autism and vertigo. The compounds can also be used to treat eating, sleep, movement, obsessive/compulsive, circadian rhythm and gastric motility disorders that are accompanied with a dysfunction of the dopaminergic system. Migraine, amyotropic lateral sclerosis, sleep disorder, anhedonia and restless leg syndrome may also be treated with the compounds.

In one embodiment of the invention, compounds acting as receptor agonists or partial agonists may be used to treat conditions such as parkinsonism, addiction, sexual dysfunction, bipolar disorder or depression or restless leg syndrome.

In another embodiment of the invention, compounds acting as receptor antagonists, inverse agonists or partial agonists may be used to treat conditions such as dyskinesia, schizophrenia, addiction, bipolar disorder, attention deficit hyperactivity disorder (ADHD), Tourette's syndrome, emesis, nausea, amnesia or obsessive/compulsive disorders.

In a preferred embodiment of the invention the compounds are used to treat movement disorders and in particular parkinsonism and restless leg syndrome. The compounds may be used to treat idiopathic parkinsonism (i.e. Parkinson's disease) and also parkinsonism and/or movement disorders that develop following the treatment of schizophrenia, exposure to toxins or drugs; or head injury.

It is preferred that compounds used to treat parkinsonism are dopamine receptor agonists or partial agonists; more preferred that the compounds are agonists of the D2 or D3 receptor; and most preferred that the compounds have higher affinity for the D3 receptor.

The inventors have found that some compounds are short acting and others are long acting when tested in an in vivo model. The inventors have found that both short and long acting dopamine receptor ligands according to the invention are useful for treating parkinsonism or for the treatment of freezing symptoms in Parkinson's disease. Preferred compounds for treating parkinsonism, or restless leg syndrome, include each of the compounds for which in vivo data is presented in FIGS. 1 to 22. In particular, short acting dopamine receptor ligands according to the invention are useful for treating parkinsonism or for the treatment of freezing symptoms in Parkinson's disease. Preferred short acting compounds for treating parkinsonism or for the treatment of freezing symptoms in Parkinson's disease are compounds 9, 24, 25, 39 and 67 (as defined in Examples A-D).

In another preferred embodiment of the invention the compounds are used to treat schizophrenia. It is preferred that compounds used to treat schizophrenia are dopamine receptor antagonists, inverse agonists, or partial agonists with low intrinsic efficacy; more preferred that the compounds are inverse agonists or antagonists at the D2 or D3 receptor; and most preferred that the compounds have higher affinity for the D3 receptor.

Preferred compounds for treating schizophrenia include compounds 3, 4, 11, 16, 18, 19, 28, 30, 36, 43, 44 and 45.

In another preferred embodiment of the invention the compounds are used to treat addiction to substances of abuse (especially alcohol, nicotine, cocaine and heroine). The compounds may also be used to control abnormal eating behaviour that can rest in obesity or undernourishment (e.g. anorexia).

Compounds that are D3 receptor agonists (e.g. compounds 12, 28, 47 and 33) may be used in substitute therapy (in place of a substance of abuse) whereas selective D3 receptor antagonists or partial agonists (e.g. compounds 3, 11, 18, 19 and 30) may be used to attenuate the dopamine receptor stimulation of the abused drug without producing undesired side effects. Conditions such as obesity may be controlled with agonists and partial agonists whereas conditions such as anorexia may be controlled with inverse agonists/antagonists or, depending on efficacy, also with partial agonists.

In another preferred embodiment of the invention the compounds are used to treat sexual dysfunctions such as male erectile problems or female sexual arousal problems. It is preferred that compounds used to treat sexual dysfunctions are dopamine receptor agonists or partial agonists; more preferred that the compounds are agonists of the D2 and/or D3 receptor; and most preferred that the compounds are selective for the D3 receptor. It is preferred that the compound is short acting in vivo. Preferred compounds for treating sexual dysfunctions bind to dopamine receptors such that they stimulate D3 receptors and have a fast onset and rapid clearing. It is preferred that the compound is short acting in vivo. Preferred compounds for treating sexual dysfunction are compounds 9, 15, 21, 24, 25, 27, 34, 39, 66 and 67, especially compounds 15, 21, 24, 25, 27, 39, 66 and 67, more especially compounds 9, 24, 25, 39 and 67 (as defined in Examples A-D).

The inventors have found that some compounds according to the invention have an unexpectedly fast onset of action and such compounds are especially useful for the treatment of diseases/conditions when a substantially immediate effect is required. Compounds that have a fast onset of action may additionally be short or long acting when tested in an in vivo model. The inventors have found that compounds according to the invention having a fast onset of action are especially useful for treating parkinsonism, for the treatment of freezing symptoms in Parkinson's disease and for the treatment of sexual dysfunction. Preferred compounds for treating parkinsonism, for the treatment of freezing symptoms in Parkinson's disease and for the treatment of sexual dysfunction, include each of the compounds for which in vivo data is presented in FIGS. 1 to 22. Preferred fast acting compounds are compounds 9, 34 and 39 (as defined in Examples A-D).

The inventors have found that some compounds according to the invention have an unexpectedly long duration of action and such compounds are especially useful for minimising the number and frequency of doses required. Compounds that have a particularly long duration of action, for example of up to about 8 hours, are compounds 28, 33 and 34 (as defined in Examples A-D).

The inventors have found that some compounds according to the invention have a substantially constant action even at increasing doses of the compound. For example, as shown in FIG. 16, compound 34 has a substantially constant action in vivo when administered (i.p.) at 1 and 3 mg/kg. This is advantageous because the dosage of the particular compound is not critical and high doses will not lead to overdoses, which potentially could cause undesirable effects. These advantages would be especially useful in situations where patient compliance may present a problem.

It will be appreciated that the amount of a compound required to treat the medical conditions is determined by biological activity and bioavailability which in turn depends on the mode of administration, the physicochemical properties of the compound employed and whether the compound is being used as a monotherapy or in a combined therapy. The frequency of administration will also be influenced by the abovementioned factors and particularly the half-life of the compound within the subject being treated.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

Generally, a daily dose of between 0.001 μg/kg of body weight and 0.1 g/kg of body weight of a compound (e.g. compound 33) may be used for the treatment of Parkinson's disease. More preferably, the daily dose is between 0.01 mg/kg of body weight and 100 mg/kg of body weight.

Daily doses may be given as a single administration (e.g. a daily tablet for oral consumption or as a single daily injection) as discussed above. Alternatively, the compound used may require administration twice or more times during a day. As an example, compound 33 for treating Parkinson's disease, may be administered as two (or more depending upon the severity of the condition) daily doses of between 5 mgs and 250 mgs in tablet form. A patient receiving treatment may take a first dose upon waking and then maybe a second dose in the evening (if on a two dose regime) or at 3 or 4 hourly intervals thereafter. Alternatively, a slow release device may be used to provide optimal doses to a patient without the need to administer repeated doses.

It is most preferred that a subject receives doses of the compound as tablets for oral ingestion. Such tablet may preferably comprise 1-20 mgs of the compound or more preferably 5-10 mgs of the compound as discussed above. It will be appreciated that a clinician will be able to calculate the amount of such tablets that will be required in a day and this will depend upon the condition being treated and the severity thereof.

When used to treat parkinsonism, the compounds may be administered in combination with one or more agents acting as anti-Parkinson agents. Examples of anti-Parkinsonian drugs are levodopa, decarboxylase inhibitors such as carbidopa and benserazide, catechol-O-methyltransferase (COMT) inhibitors such as tolcapone and entacapone, monoamine-oxidase (MAO) inhibitors such as tranylcypromine, pargyline and moclobemide, preferred MAO B inhibitors such as selegiline and rasagiline as well as dopamine agonist such as ergoline derivatives like bromocriptine, pergolide, dihydroergocryptine, cabergoline or compounds such as apomorphine, ropinerol, pramipexole, rotigotine, fipamezole, melevodopa, sumarinole and sarizotane and NMDA receptor antagonists or modulators such as amantadine, memantine and budipine.

In another embodiment of the invention the present compounds are administered in combination with an agent acting on acetylcholine inhibitors such as rivastigmine, tacrine, donepezile and galanthamine for treating cognitive impairment.

In another embodiment of the invention the present compounds are administered in combination with an agent acting on calcium channels such as nimodipine, nifedipine, felodipine, nicardipine, isrrapidine, diltiazem and verapamil for treating cognitive impairment.

In another embodiment of the invention the present compounds are administered in combination with an agent acting as nootropica such as piracetam and pyritinol for treating cognitive impairment.

In another embodiment of the invention the present compounds are administered in combination with an agent acting on phosphodiesterase such as sildenafile, vardenafile and tadalafile for treating sexual dysfunction.

Preparation of the Compounds According to the Invention

A compound of formula (I), or a pharmaceutically acceptable salt thereof, may be prepared by any process known to be applicable to the preparation of chemically-related compounds. The present invention provides such processes, when used to prepare a compound of formula (I), which processes are illustrated by the following representative process variants in which, unless otherwise stated, the integer n and the R and Z groups have any of the meanings defined herein. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated, which are within the ordinary skill of an organic chemist.

For example, a compound of formula (Ia), or a pharmaceutically acceptable salt thereof, where n is 1 and the linking group Z is a substituted or unsubstituted $C_1$-$C_4$ alkylene group may be prepared by the reaction of a compound of formula (II):

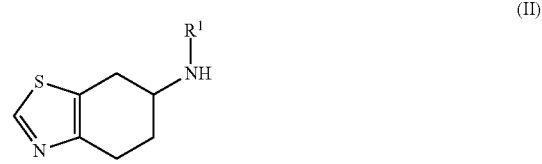

(II)

wherein $R^1$ has any of the meanings defined herein except that any functional group is protected if necessary, with a compound of formula (III):

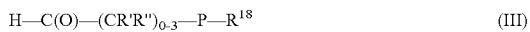

H—C(O)—(CR'R")$_{0-3}$—P—$R^{18}$ (III)

wherein P and $R^{18}$ each have any of the meanings defined herein and the CR'R" groups represent a substituted or unsubstituted $C_1$-$C_4$ alkylene group except that any functional group is protected if necessary, in the presence of a reagent for reductive amination; and optionally, (i) converting a compound of formula (I) into another compound of formula (I); and/or
(ii) removing any protecting group that is present (by conventional means); and/or
(iii) forming a pharmaceutically acceptable salt.

A suitable reagent for reductive amination for use in the reaction of a compound of formula (II) with a compound of formula (III) is sodium triacetoxyborohydride. The reaction may be conducted in the presence of a suitable inert solvent or diluent, for example 1,2-dichloroethane, and at a suitable temperature, for example ambient temperature.

For example, a compound of formula (Ia), or a pharmaceutically acceptable salt thereof, where n is at least 1 may be prepared by the reaction of a compound of formula (II):

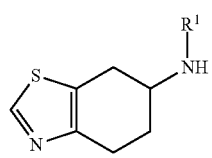
(II)

wherein $R^1$ has any of the meanings defined herein except that any functional group is protected if necessary, with a compound of formula (IV):

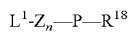 (IV)

wherein n, Z, P and $R^{18}$ each have any of the meanings defined herein and $L^1$ is a suitable displaceable group except that any functional group is protected if necessary; and optionally,
(i) converting a compound of formula (I) into another compound of formula (I); and/or
(ii) removing any protecting group that is present (by conventional means); and/or
(iii) forming a pharmaceutically acceptable salt.

The displaceable group $L^1$ may represent any suitable displaceable group such as a halo (for example chloro, bromo or iodo, especially bromo) or a hydroxy group. When $L^1$ is a halo group (especially bromo), the reaction of a compound of formula (II) with a compound of formula (IV) is conveniently conducted in the presence of a suitable base, such as triethylamine. When $L^1$ is a hydroxy group, the reaction of a compound of formula (II) with a compound of formula (IV) is conveniently conducted in the presence of (cyanomethyl) trimethylphosphonium iodide and a suitable base, such as N,N-diisopropylethylamine. The reaction may be conducted in the presence of a suitable inert solvent or diluent, for example propionitrile when $L^1$ is hydroxy and acetone when $L^1$ is bromo, and at a suitable temperature, for example from ambient temperature to about 100° C.

A compound of formula (Ic), or a pharmaceutically acceptable salt thereof, may be prepared by the reaction of a compound of formula (V) or a reactive derivative thereof:

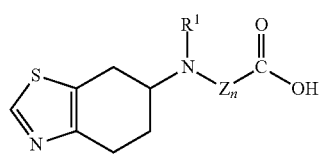
(V)

wherein n, $R^1$ and Z each have any of the meanings defined herein except that any functional group is protected if necessary, with an amine of formula (VI):

 (VI)

wherein $R^{10}$ and $R^{11}$ each have any of the meanings defined herein except that any functional group is protected if necessary; and optionally,
(i) converting a compound of formula (I) into another compound of formula (I); and/or
(ii) removing any protecting group that is present (by conventional means); and/or
(iii) forming a pharmaceutically acceptable salt.

By the term "reactive derivative" of the carboxylic acid of formula (V) is meant a carboxylic acid derivative that will react with the amine of formula (IV) to give the corresponding amide. A suitable reactive derivative of a carboxylic acid of formula (V) is, for example, an acyl halide, for example an acyl chloride formed by the reaction of the acid and an inorganic acid chloride (for example thionyl chloride) or by the reaction of the acid and triphosgene. The reaction of such reactive derivatives of a carboxylic acid with an amine is well known in the art. For example, the reaction may be conducted in the presence of a suitable base such as triethylamine, in a suitable inert solvent or diluent such as dichloromethane and at a suitable temperature such as ambient temperature.

Compounds of Formula (II), (III), (IV), (V) and (VI) are commercially available or may be prepared using conventional procedures of organic chemistry, which would be well known to a person skilled in the art.

As the skilled person would appreciate, the preparation of compounds of formula (I) may involve, at various stages, the addition and removal of one or more protecting groups. The protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule. The protection and deprotection of functional groups is described in 'Protective Groups in Organic Synthesis', 2nd edition, T. W. Greene and P. G. M. Wuts, Wiley-Interscience (1991).

As the skilled person would appreciate, by the term "inert solvent or diluent" we mean a solvent or diluent that does not react with the starting materials, reagents, intermediates or products in a manner which adversely affects the yield of the desired product.

As a person skilled in the art would appreciate, in order to obtain compounds of the present invention in an alternative and possibly more convenient manner, the individual process steps mentioned hereinbefore may be performed in a different order and/or the individual reactions may be performed at different stage in the overall route.

References herein to compounds of the invention of course refer to compounds of the formula (I), (Ia), (Ib), (Ic), (Id) and (Ie) as defined herein.

The invention is illustrated with reference to the following non-limiting Examples and accompanying drawings, in which.

Figure 1:
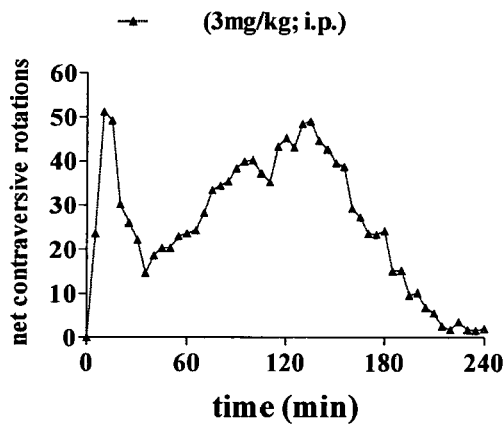
FIG. 1 is a graphic representation of the results of an in vivo study of the effect of compound 1 (synthesized in Example A1 below; i.p administration at 3 mg/kg) on the rotational behaviour in a rat model.
Figure 2:
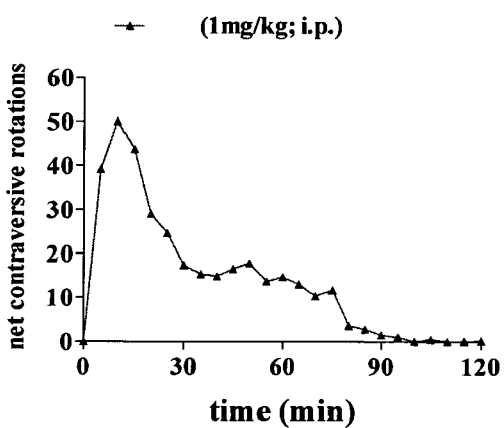
FIG. 2 is a graphic representation of the results of an in vivo study of the effect of compound 15 (synthesized in Example A14 below; i.p. administration at 1 mg/kg) on the rotational behaviour in a rat model.
Figure 3:
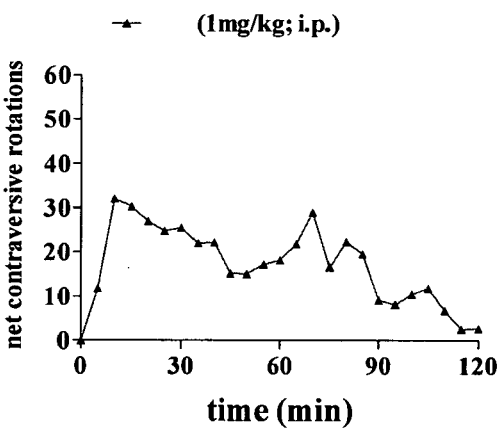
FIG. 3 is a graphic representation of the results of an in vivo study of the effect of compound 12 (synthesized in Example A11 below; i.p. administration at 1 mg/kg) on the rotational behaviour in a rat model.
Figure 4:
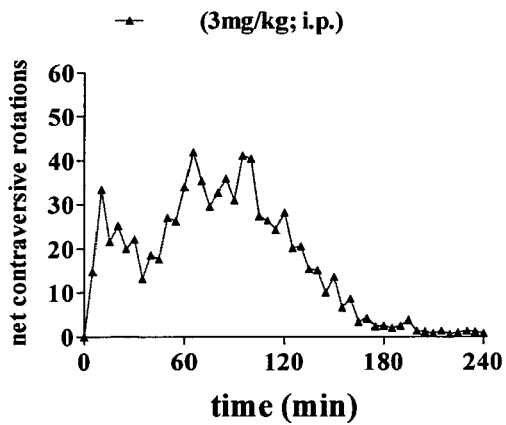
FIG. 4 is a graphic representation of the results of an in vivo study of the effect of compound 20 (synthesized in Example A19 below; i.p. administration at 3 mg/kg) on the rotational behaviour in a rat model.
Figure 5:
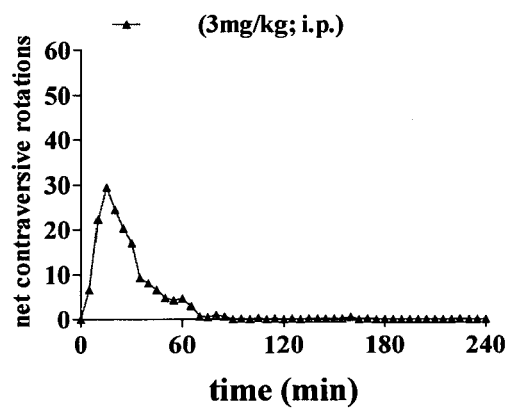
FIG. 5 is a graphic representation of the results of an in vivo study of the effect of compound 24 (synthesized in Example A23 below; i.p. administration at 3 mg/kg) on the rotational behaviour in a rat model.
Figure 6:
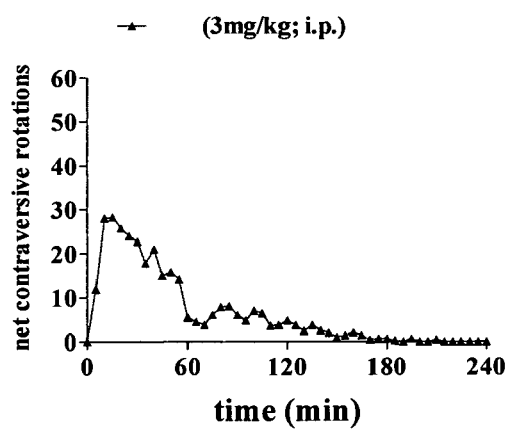
FIG. 6 is a graphic representation of the results of an in vivo study of the effect of compound 26 (synthesized in Example A25 below; i.p. administration at 3 mg/kg) on the rotational behaviour in a rat model.
Figure 7:
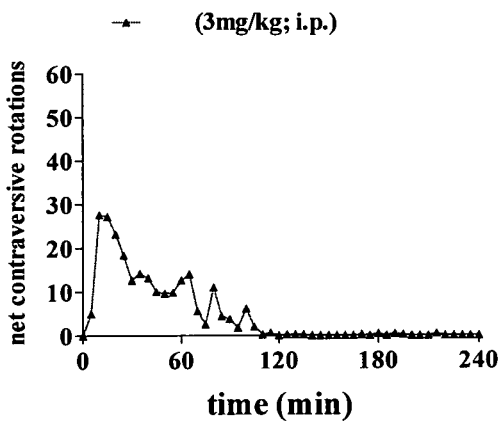
FIG. 7 is a graphic representation of the results of an in vivo study of the effect of compound 21 (synthesized in Example A20 below; i.p. administration at 3 mg/kg) on the rotational behaviour in a rat model.
Figure 8:
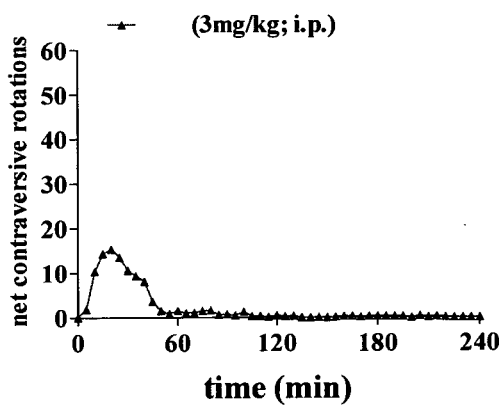
FIG. 8 is a graphic representation of the results of an in vivo study of the effect of compound 25 (synthesized in Example A24 below; i.p. administration at 3 mg/kg) on the rotational behaviour in a rat model.
Figure 9:
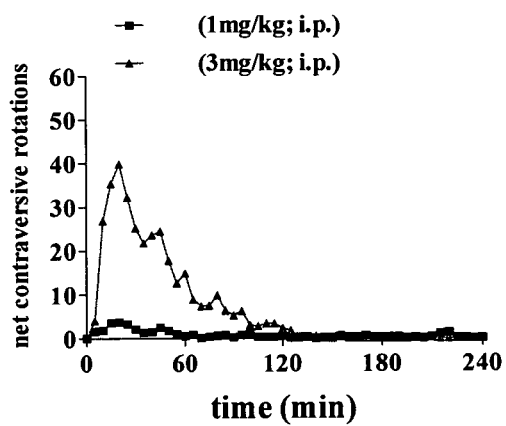
FIG. 9 is a graphic representation of the results of an in vivo study of the effect of compound 27 (synthesized in Example A26 below; i.p administration at 1 and 3 mg/kg) on the rotational behaviour in a rat model.
Figure 10:
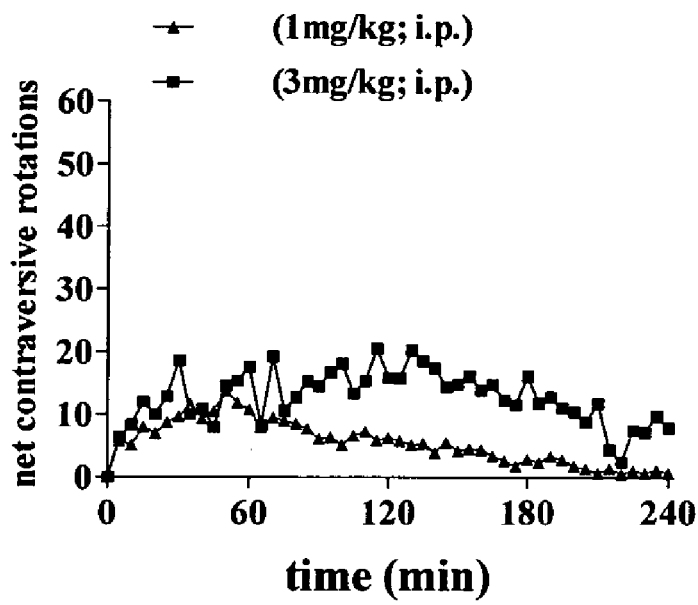
FIG. 10 is a graphic representation of the results of an in vivo study of the effect of compound 65 (synthesized in Example A10 below; i.p. administration at 1 and 3 mg/kg) on the rotational behaviour in a rat model.
Figure 11:
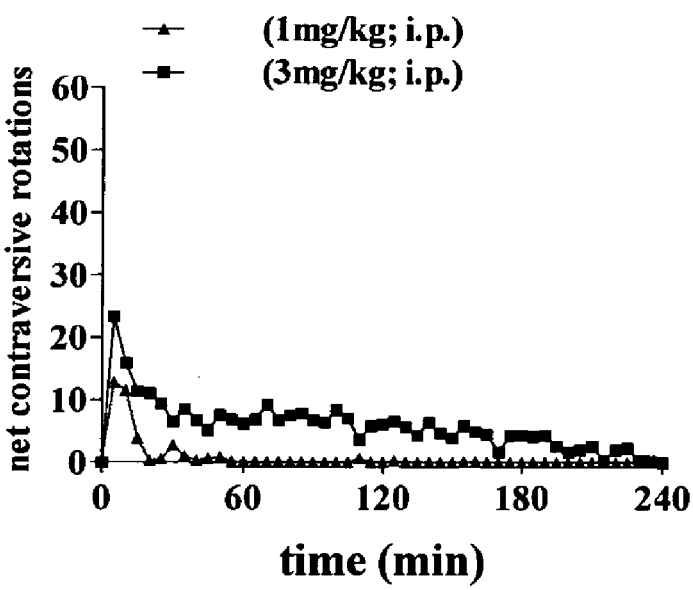
FIG. 11 is a graphic representation of the results of an in vivo study of the effect of compound 9 (synthesized in Example B1 below; i.p. administration at 1 and 3 mg/kg) on the rotational behaviour in a rat model.
Figure 12:
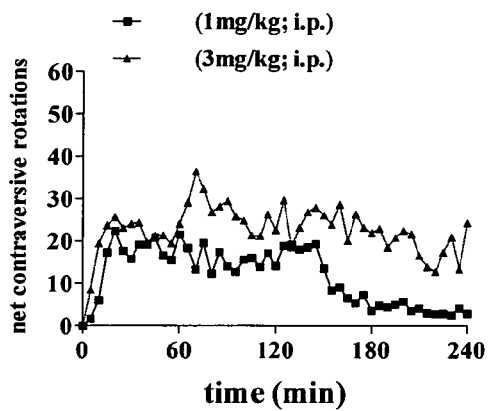
FIG. 12 is a graphic representation of the results of an in vivo study of the effect of compound 68 (synthesized in Example B7 below; i.p. administration at 1 and 3 mg/kg) on the rotational behaviour in a rat model.
Figure 13:
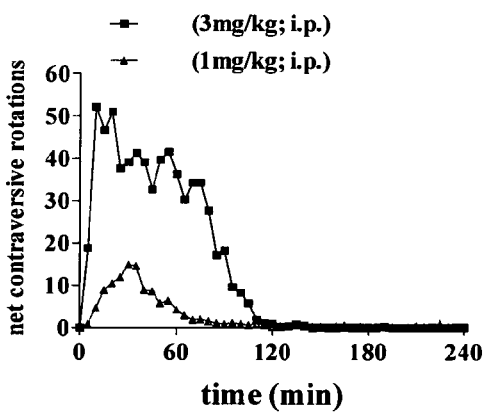
FIG. 13 is a graphic representation of the results of an in vivo study of the effect of compound 66 (synthesized in Example B5 below; i.p. administration at 1 and 3 mg/kg) on the rotational behaviour in a rat model.
Figure 14:
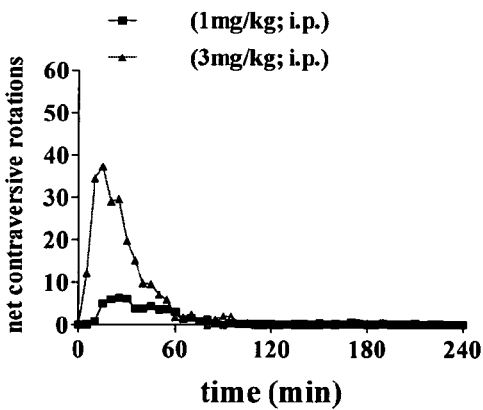
FIG. 14 is a graphic representation of the results of an in vivo study of the effect of compound 67 (synthesized in Example B6 below; i.p. administration at 1 and 3 mg/kg) on the rotational behaviour in a rat model.
Figure 15:
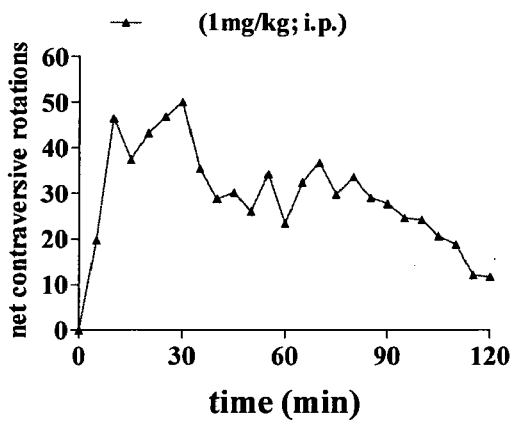
FIG. 15 is a graphic representation of the results of an in vivo study of the effect of compound 28 (synthesized in Example C1 below; i.p. administration at 1 mg/kg) on the rotational behaviour in a rat model.
Figure 16:
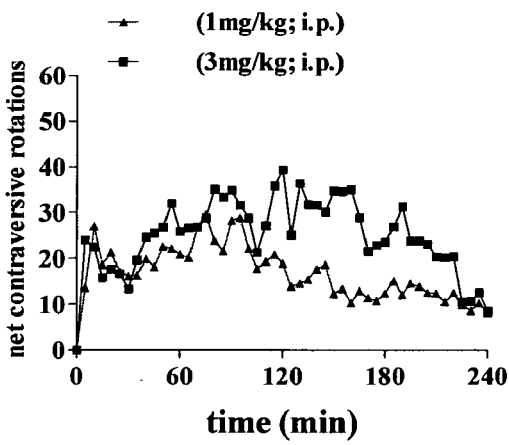
FIG. 16 is a graphic representation of the results of an in vivo study of the effect of compound 34 (synthesized in Example C6 below; i.p. administration at 1 and 3 mg/kg) on the rotational behaviour in a rat model.
Figure 17:
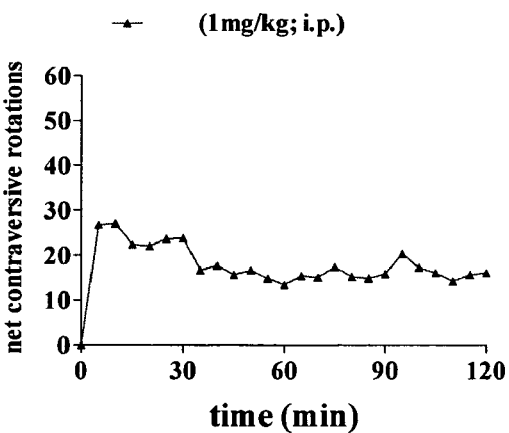
FIG. 17 is a graphic representation of the results of an in vivo study of the effect of compound 33 (synthesized in Example C5 below; i.p. administration at 1 mg/kg) on the rotational behaviour in a rat model.
Figure 18:
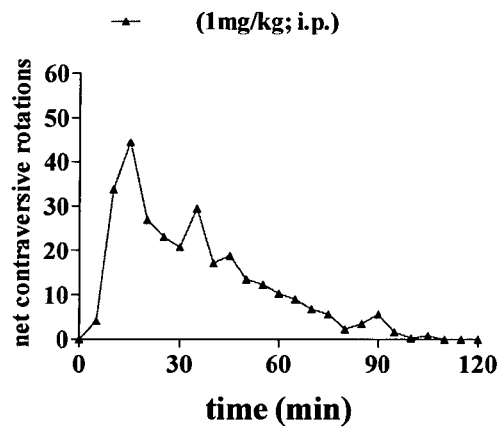
Figure 19:
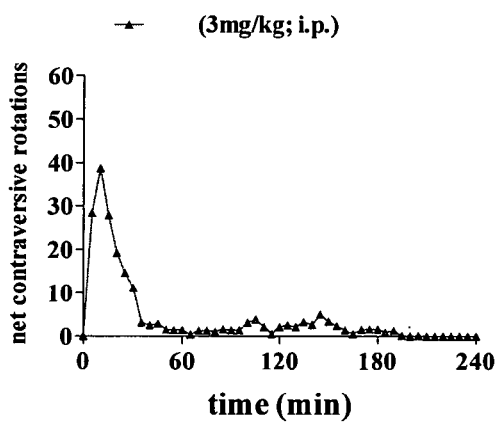

FIG. 18 is a graphic representation of the results of an in vivo study of the effect of compound 38 (synthesized in Example C10 below; i.p. administration at 1 mg/kg) on the rotational behaviour in a rat model; and FIG. 19 is a graphic representation of the results of an in vivo study of the effect of compound 39 (synthesized in Example C11 below; i.p. administration at 3 mg/kg) on the rotational behaviour in a rat model.

Figure 20:
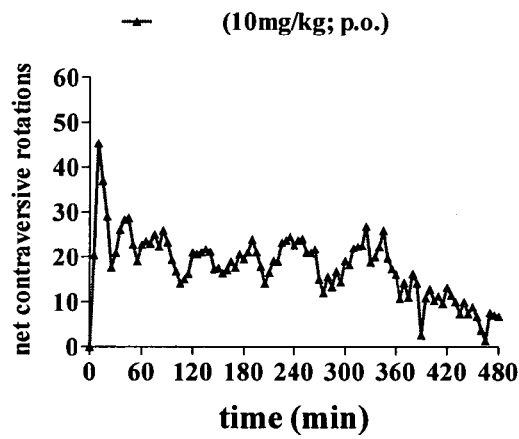
Figure 21:
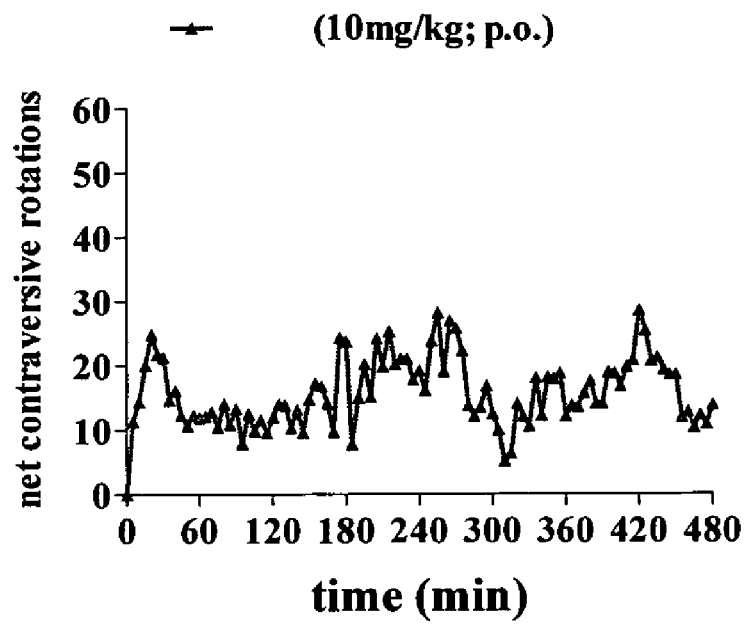
Figure 22:
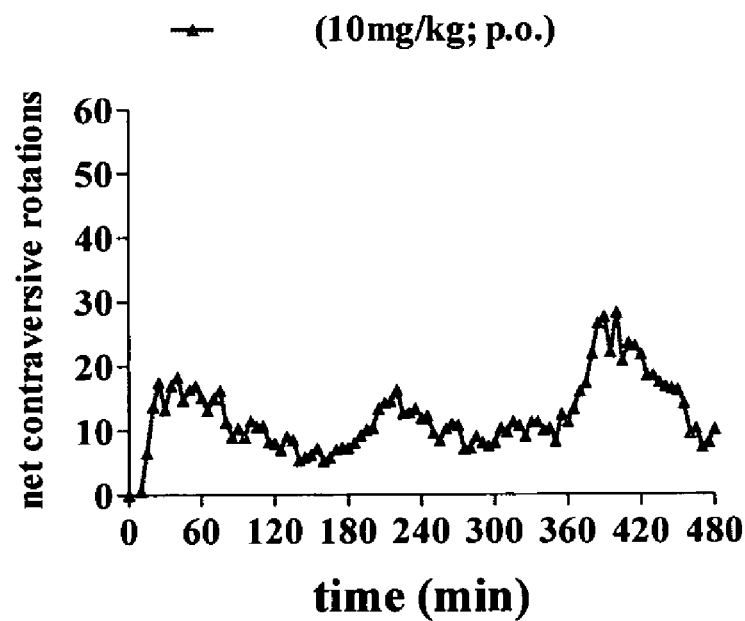

FIG. 20 is a graphic representation of the results of an in vivo study of the effect of compound 28 (synthesized in Example C1 below; p.o. administration at 10 mg/kg) on the rotational behaviour in a rat model;

FIG. 21 is a graphic representation of the results of an in vivo study of the effect of compound 33 (synthesized in Example C5 below; p.o. administration at 10 mg/kg) on the rotational behaviour in a rat model;

FIG. 22 is a graphic representation of the results of an in vivo study of the effect of compound 34 (synthesized in Example C6 below; p.o. administration at 10 mg/kg) on the rotational behaviour in a rat model.

EXAMPLES

Example A

The inventors synthesized 32 compounds according to the present invention by employing the methods set out below in Examples A1 to A32 with reference, where appropriate, to methods described in the Synthetic Methods section which follows.

Example A1

N-{4-[Propyl-(4,5,6,7-tetrahydro-benzothiazol-6-yl)-amino]-butyl}-benzamide (1)

STEP A: Preparation of (1,4-Dioxa-spiro[4.5]dec-8-yl)-propyl-amine (1A)

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N6-propyl-4,5,6,7-tetrahydro-benzothiazole-2,6-diamine dihydrobromide (1B)

A solution of 12.0 g (60 mmol) (1,4-dioxa-spiro[4.5]dec-8-yl)-propyl-amine in 120 mL concentrated aqueous hydrobromic acid is stirred for 15 minutes at room temperature and then 3.12 mL (60 mmol) bromine are added. After further stirring for 15 minutes, 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 65%; ESI-MS: 153 (57), 212 (M+H$^+$, 100).

STEP C: Preparation of propyl-(4,5,6,7-tetrahydro-benzothiazol-6-yl)-amine (1C)

To a solution of 14.5 g (38.9 mmol) N6-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with Chloroform/Ethanol 5:1 (3×250 mL) The solution is dried over anhydrous sodium sulfate and concentrated in vacuum. The brown oil obtained is chromatographed over silica gel, eluting with dichloromethane/methanol 97:3 under ammonia atmosphere.

Yield: 66%; ESI-MS: 197 (M+H$^+$).

STEP D: Preparation of N-(4-hydroxy-butyl)-benzamide (1D)

A solution of 1.16 mL (10 mmol) of benzoylchloride in 10 mL dichloromethane is added to 0.93 mL (10 mmol) of 4-amino-butan-1-ol and 4.2 mL (30 mmol) of triethylamine dissolved in 50 mL of dichloromethane. The mixture is stirred overnight. 50 mL of saturated sodium carbonate solution is added. The organic phase is separated, dried with sodium sulfate and the solvent evaporated.

Yield: 64%; ESI-MS: 120 (43), 192 (M+H$^+$).

STEP E: Preparation of N-(4-oxo-butyl)-benzamide (1E)

A solution of 0.95 mL (11 mmol) oxalyl chloride in 30 mL of dichloromethane is cooled to −80° C. under argon atmosphere. 2 mL (28 mmol) of dimethylsulfoxide in 8 mL of dichloromethane is introduced dropwise over 10 minutes. After 5 minutes a solution of 1.16 g (6 mmol) 10 in 8 mL dichloromethane and 2 mL dimethylsulfoxide is added over the course of 10 minutes. The reaction mixture is stirred for another hour at −80° C. before 5 mL of triethylamine is added and the mixture is allowed to warm up to room temperature. 50 mL of saturated brine solution is added for hydrolysis. The organic phase is separated, extracted three times with a saturated solution of sodium chloride, dried over sodium sulfate and the solvent is evaporated. The crude product is obtained in almost quantitative yield.

STEP F: Preparation of (1)

A solution of 395 mg (2 mmol) propyl-(4,5,6,7-tetrahydro-benzothiazol-6-yl)-amine and 478 mg (2.5 mmol) N-(4-oxo-butyl)-benzamide in 1,2-dichloroethane (20 mL) is stirred for about 30 minutes. Then 0.75 g (3 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel eluting with dichloromethane/methanol (98:2). The methanol used is saturated with NH$_3$-gas. Evaporation of the solvent yields 1.88 mmol (700 mg) of a colorless viscous oil. The salt of maleic acid is crystallized from acetonitrile/diethylether.

Yield: 68%; ESI-MS: 372 (M+H$^+$); mp: 152° C.; formula: $C_{21}H_{29}N_3OS \times C_4H_4O_4 \times 0.75H_2O$ (calculated: C, 59.92; H, 6.94; N, 8.39; found: C, 60.03; H, 7.00; N, 8.27).

Example A2

Naphthalene-2-carboxylic acid [4-(4,5,6,7-tetrahydro-benzothiazol-6-ylamino)-butyl]-amide (2)

STEP A: 1,4-Dioxa-spiro[4.5]dec-8-ylamine (2A) is synthesized as been described for 1A using methanol which has been saturated with ammonia.

ESI-MS: 158 (M+H$^+$).

STEP B: 4,5,6,7-Tetrahydro-benzothiazole-2,6-diamine dihydrobromide (2B) is received by proceeding as described for 1B from 2A.

Yield: 51%; ESI-MS: 170 (M+H$^+$).

STEP C: Preparation of 4,5,6,7-tetrahydro-benzothiazol-6-ylamine (2C) is performed as described for 1C from 2B.

Yield: 48%; ESI-MS: 155 (M+H$^+$).

STEP D: Preparation of naphthalene-2-carboxylic acid (4-hydroxy-butyl)-amide (2D)

43 mmol (8.2 g) naphthalen-2-carboxylic acid chloride is dissolved in 50 mL dioxane and dropwise added to a solution of 112 mmol (10.0 g) 4-amino-butan-1-ol in 100 mL dioxane and stirred overnight at room temperature. The mixture is then poured into 200 mL of ice water and filtrated. The white solid separated is dried under vacuum.

Yield: 6.2 g (59%); ESI-MS: 244 (M+H$^+$).

STEP E: Naphthalene-2-carboxylic acid (4-oxo-butyl)-amide (2E) is prepared analogously to 1E starting with 2D.

STEP F: Compound 2 is prepared analogously to 1 from 2C and 2E.

Yield: 59%; ESI-MS: 380 (M+H$^+$).

An example is crystallized as salt of oxalic acid from methanol/diethylether.

Formula: $C_{22}H_{25}N_3OS \times C_2H_2O_4$ (calculated: C, 91.39; H, 5.80; N, 8.95; found: C, 61.19; H, 5.87; N, 8.76).

Example A3

Naphthalene-2-carboxylic acid {4-[methyl-(4,5,6,7-tetrahydro-benzothiazol-6-yl)-amino]-butyl}-amide (3)

STEP A: Preparation of (1,4-dioxa-spiro[4.5]dec-8-yl)-methyl-amine (3A) is performed as described for 1A with a 40% aqueous solution of methylamine.

ESI-MS: 172 (M+H$^+$).

STEP B: N6-Methyl-4,5,6,7-tetrahydro-benzothiazole-2,6-diamine dihydrobromide (3B) is prepared from 3A as described for 1B.

Yield: 62%; ESI-MS: 153 (61), 184 (M+H$^+$, 100).

STEP C: Methyl-(4,5,6,7-tetrahydro-benzothiazol-6-yl)-amine (3C) is prepared from 3B as described for 1C.

Yield: 40%; ESI-MS: 169 (M+H$^+$).

STEP D: Compound 3 is prepared from 2E and 3C as described for 1. The resulting oil is crystallized as salt of oxalic acid from ethanol/diethylether.

Yield: 25%; ESI-MS: 394 (M+H$^+$); mp: 122° C.; formula: $C_{23}H_{27}N_3OS \times C_2H_2O_4$ (calculated: C, 62.09; H, 6.04; N, 8.69; found: C, 61.83; H, 6.30; N, 8.55).

Example A4

Naphthalene-2-carboxylic acid {4-[ethyl-(4,5,6,7-tetrahydro-benzothiazol-6-yl)-amino]-butyl}-amide (4)

STEP A: (1,4-Dioxa-spiro[4.5]dec-8-yl)-ethylamine (4A) is prepared operating as described for 1A with 7.85 mL (120 mmol) of cooled liquid ethylamine.

ESI-MS: 141 (15), 186 (M+H$^+$, 100).

STEP B: N6-Ethyl-4,5,6,7-tetrahydro-benzothiazole-2,6-diamine dihydrobromide (4B) is prepared from 4A analogously to 1B.

Yield: 69%; ESI-MS: 153 (27), 198 (M+H$^+$, 100).

STEP C: Ethyl-(4,5,6,7-tetrahydro-benzothiazol-6-yl)-amine (4C) is prepared from 4B as described for 1C.

Yield: 45%; ESI-MS: 138 (17), 183 (M+H$^+$, 100).

STEP D: Compound 4 is prepared from 2E and 4C as described for 1. The salt of oxalic acid is crystallized from ethanol/diethylether.

Yield: 22%; ESI-MS: 408 (M+H$^+$); mp: 120° C.; formula: $C_{24}H_{29}N_3OS \times C_2H_2O_4 \times 0.5H_2O$ (calculated: C, 61.64; H, 6.37; N, 8.29; found: C, 61.39; H, 6.44; N, 8.25).

Example A5

Naphthalene-2-carboxylic acid {4-[propyl-(4,5,6,7-tetrahydro-benzothiazol-6-yl)-amino]-butyl}-amide (5)

Compound 2 is dissolved in 30 mL acetonitrile 0 3 mL propionaldehyde (4 mmol) and 100 mg sodium cyanoborohydride (1.6 mmol) is added to the mixture. The pH is adjusted to 5-6 with glacial acetic acid. The mixture is stirred at room temperature for 30 minutes and made basic with ammonia solution and water. The raw product is extracted with dichloromethane, which is dried with sodium sulfate and evaporated to yield brown oil. The product is purified by chromatotron using dichloromethane/methanol 100:1 as an eluent. The resulting base is crystallized as salt of maleic acid from methanol/diethylether.

Yield: 50%; ESI-MS: 422 (M+H$^+$); $C_{25}H_{31}N_3OS \times C_4H_4O_4 \times H_2O$ (calculated: C, 62.68; H, 6.71; N, 7.56; found: C, 62.16; H, 6.74; N, 7.85).

Example A6

Naphthalene-2-carboxylic acid {4-[allyl-(4,5,6,7-tetrahydro-benzothiazol-6-yl)-amino]-butyl}-amide (6)

A mixture of 700 mg (1.84 mmol) 2, 0.5 mL allyliodide (5.5 mmol), 30 mL dry acetone and 1.0 g (7.4 mmol) potassium carbonate is stirred overnight at room temperature under an argon atmosphere. The suspension is filtrated, the filtrate concentrated in vacuum and purified via column chromatography. The resulting oil is crystallized from acetonitrile/diethylether as salt of oxalic acid.

Yield: 35%; ESI-MS: 420 (M+H$^+$); mp: 128° C.; formula: $C_{25}H_{29}N_3OS \times C_2H_2O_4 \times 0.5H_2O$ (calculated: C, 62.53; H, 6.22; N, 8.10; found: C, 62.25; H, 6.22; N, 7.84).

Example A7

Naphthalene-2-carboxylic acid {4-[prop-2-ynyl-(4,5,6,7-tetrahydro-benzothiazol-6-yl)-amino]-butyl}-amide (7)

Preparation of 7 is performed as described for 6 with propargylbromide, acetonitrile as solvent and triethylamine as base instead of potassium carbonate. The salt of oxalic acid was crystallized from acetonitrile/diethylether.

Yield: 16%; ESI-MS: 408 (M+H$^+$); mp: 126° C.; formula: $C_{25}H_{27}N_3OS \times C_2H_2O_4 \times 0.75H_2O$ (calculated: C, 62.23; H, 5.90; N, 8.06; found: C, 61.95; H, 5.74; N, 7.83).

Example A8

Naphthalene-2-carboxylic acid {4-[but-2-ynyl-(4,5,6,7-tetrahydro-benzothiazol-6-yl)-amino]-butyl}-amide (8)

Preparation was performed as described for 7 with 1-bromo-but-2-yne.

Yield: 7%; ESI-MS: 432 (M+H$^+$); mp: 147° C.; formula: $C_{26}H_{29}N_3OS \times C_2H_2O_4 \times 1.25H_2O$ (calculated: C, 61.80; H, 6.21; N, 7.72; found: C, 61.71; H, 6.13; N, 7.67).

Example A9

Benzo[b]thiophene-2-carboxylic acid [4-(4,5,6,7-tetrahydro-benzothiazol-6-ylamino)-butyl]-amide (10)

STEP A: Preparation of benzothiophene-2-carboxylic acid (4-hydroxy-butyl)-amide (10A) is performed as described for 1D using benzothiophene-2-carboxylic acid chloride.

Yield: 86%; ESI-MS: 250 (M+H$^+$).

STEP B: Preparation of 10.

2C (230 mg, 1.5 mmol) was stirred with 10A (382 mg, 1.6 mmol), (cyanomethyl)trimethylphosphonium iodide (437 mg, 1.8 mmol) and DIPEA (243 mg, 1.9 mmol) in propionitrile (6 ml) at 90° C. for 3 hours. The mixture was allowed to cool to room temperature and water 15 ml and K$_2$CO$_3$ 2 g was added to the mixture. The mixture was then extracted three times with dichloromethane and dried with Na$_2$SO$_4$ and evaporated. The product was purified by flash chromatography using dichloromethane/methanol 100:4 as and eluent. Crystallisation was performed from methanol/diethylether as salt of oxalic acid.

Yield: 17%; ESI-MS: 386 (M+H$^+$); formula: $C_{20}H_{23}N_3OS_2 \times C_2H_2O_4$ (calculated: C, 55.56; H, 5.30; N, 8.84; found: C, 55.33; H, 5.34; N, 8.65).

Example A10

Benzo[b]thiophene-2-carboxylic acid {4-[methyl-(4,5,6,7-tetrahydro-benzothiazol-6-yl)-amino]-butyl}-amide (11)

STEP A: Preparation of benzo[b]thiophene-2-carboxylic acid (4-oxo-butyl)-amide (11A) is performed from 10A as described for 1E.

STEP B: Compound 11 is prepared as described for 1 from 1C and 11A. The salt of oxalic acid is crystallized from ethanol/diethylether.

Yield: 58%; ESI-MS: 400 (M+H$^+$); mp: 105° C.; formula: $C_{21}H_{25}N_3OS_2 \times C_2H_2O_4 \times 0.5H_2O$ (calculated: C, 55.40; H, 5.66; N, 8.43; found: C, 55.52; H, 5.52; N, 8.46).

Example A11

Benzo[b]thiophene-2-carboxylic acid {4-[ethyl-(4,5,6,7-tetrahydro-benzothiazol-6-yl)-amino]-butyl}-amide (12)

Compound 12 is prepared from 2C as described for 11.

Yield: 24%; ESI-MS: 414 (M+H$^+$); mp: 103° C.; formula: $C_{22}H_{27}N_3OS_2 \times C_2H_2O_4 \times 0.5H_2O$ (calculated: C, 56.23; H, 5.90; N, 8.20; found: C, 55.92; H, 5.94; N, 7.91).

Example A12

Benzo[b]thiophene-2-carboxylic acid {4-[propyl-(4,5,6,7-tetrahydro-benzothiazol-6-yl)-amino]-butyl}-amide (13)

Compound 13 is prepared from 10 as described for 5. Salt of oxalic acid is crystallized from ethanol/diethylether.

Yield: 67%; ESI-MS: 428 (M+H$^+$); formula: $C_{23}H_{29}N_3OS_2 \times C_2H_2O_4 \times H_2O \times 0.25CH_3CN$ (calculated: C, 56.10; H, 6.23; N, 8.34; found: C, 55.91; H, 6.35; N, 8.76).

Example A13

Benzothiazole-6-carboxylic acid {4-[ethyl-(4,5,6,7-tetrahydro-benzothiazol-6-yl)-amino]-butyl}-amide (14)

STEP A: Preparation of benzothiazole-6-carboxylic acid (4-hydroxy-butyl)-amide (14A).

2.69 g (15 mmol) of benzothiazole-6-carboxylic acid is dissolved in a mixture of 1.34 g (15 mmol) 4-amino-butan-1-ol and 70 mL dry tetrahydrofuran. 2.43 g (15 mmol) of CDI is added after stirring for 30 minutes and then stirred for another hour. The mixture is concentrated in vacuum. The resulting residue is suspended in dichloromethane, water is added, and the organic phase is separated. The aqueous phase is extracted with dichloromethane twice. The combined organic phases are dried over sodium sulfate and concentrated in vacuum.

Yield: 55%; ESI-MS: 251 (M+H$^+$).

STEP B: Preparation of benzothiazole-6-carboxylic acid (4-oxo-butyl)-amide (14B) is performed as described for 1E from 14A.

STEP C: Preparation of 14 is performed as described for 1 using 14B as educts.

Yield: 76%; ESI-MS: 415 (M+H$^+$); mp: 106.5° C.; formula: $C_{21}H_{26}N_4OS_2 \times C_2H_2O_4 \times 0.75H_2O$ (calculated: C, 53.32; H, 5.74; N, 10.81; found: C, 53.23; H, 5.50; N, 10.86).

Example A14

Benzothiazole-6-carboxylic acid {44propyl-(4,5,6,7-tetrahydro-benzothiazol-6-yl)-amino]-butyl}-amide (15)

Preparation of 15 is performed as described for 5 starting with 197 mg (1 mmol) 1C and 300 mg (1.2 mmol) 14B.

Yield: 60%; ESI-MS: 429 (M+H$^+$), formula: $C_{22}H_{28}N_4OS_2 \times C_2H_2O_4 \times 0.75H_2O$ (calculated: C, 54.17; H, 5.97; N, 10.53; found: C, 54.21; H, 6.15; N, 10.14).

Example A15

N-{4-[Propyl-(4,5,6,7-tetrahydro-benzothiazol-6-yl)-amino]-butyl}-cinnamoylamide (16)

STEP A: Preparation of N-(4-hydroxy-butyl)-cinnamoylamide (16A) is performed as described for 1D starting with cinnamoylchloride.

Yield: 82%; ESI-MS: 220 (M+H$^+$)

STEP B: Preparation of N-[4-(4,5,6,7-tetrahydro-benzothiazol-6-ylamino)-butyl]-cinnamoylamide (16B) is performed as described for 10 using 16A as educt. The resulting oil is not pure and is used in the further reaction step as it is.

STEP C: Preparation of 16 is performed as described for 5 using 16B and propionaldehyde as educts.

Yield: 19% (according to 16A) ESI-MS: 398 (M+H$^+$); formula: $C_{23}H_{31}N_3O_1S_1 \times C_4H_4O_4 \times H_2O \times 0.35CH_3CN$ (calculated: C, 58.98; H, 7.16; N, 8.32; found: C, 58.80; H, 6.86; N, 8.67).

Example A16

2,4-Dichloro-N-{4-[propyl-(4,5,6,7-tetrahydro-benzothiazol-6-yl)-amino]-butyl}-cinnamoylamide (17)

STEP A: Preparation of 2,4-dichloro-N-(4-hydroxy-butyl)-cinnamoylamide (17A).

2,4-Dichlorocinnamoylchloride is stirred in thionylchloride for 2 hours at 60° C. Thionylchloride is evaporated and the resulting residue is used for the procedure described for 1D.

Yield: 87%.

STEP B: Preparation of 2,4-dichloro-N-(4-oxo-butyl)-cinnamoylamide (17B).

A mixture of 1.0 g (3.6 mmol) 17A, 947 mg (2.5 mmol) pyridinium dichromate, 1.1 g (10.8 mmol) acetic anhydride, 6 mL N,N-dimethylformamide and 30 mL dichloromethane is stirred at room temperature for 3 hours. After filtration through silica gel dichloromethane is evaporated in vacuum. The resulting solution in N,N-dimethylformamide is used as it is in the following reaction step.

STEP C: Preparation of 17 is performed as described for 5 using 1C and 17B as starting materials. The salt of oxalic acid is crystallized from methanol/diethylether.

Yield: 21%; ESI-MS: 466 (M+H$^+$); formula: $C_{23}H_{29}Cl_2N_3OS \times C_2H_2O_4 \times 3H_2O$ (calculated: C, 49.18; H, 6.11; N, 6.88; found: C, 49.36; H, 5.80; N, 6.59).

Example A17

4-Fluoro-N-{4-[propyl-(4,5,6,7-tetrahydro-benzothiazol-6-yl)-amino]-butyl}-cinnamoylamide (18)

STEP A: Preparation of 4-fluoro-N-(4-hydroxy-butyl)-cinnamoylamide (18A) is performed as described for 17A using 4-fluorocinamic acid as educt.

Yield: 68%

STEP B: Preparation of 4-fluoro-N-(4-oxo-butyl)-cinnamoylamide (18B) is performed as described for 17B starting with 18A.

STEP C: Preparation of 18 is performed as described for 5 using 1C and 18B as starting material. The salt of oxalic acid is crystallized from methanol/diethylether.

Yield: 26%; ESI-MS: 416 (M+H$^+$); formula: $C_{23}H_{30}FN_3OS \times C_2H_2O_4 \times 1.5H_2O$ (C, 56.38; H, 6.62; N, 7.89; found: C, 56.39; H, 6.67; N, 7.63).

Example A18

2-(4-Chloro-phenyl)-thiazole-5-carboxylic acid {4-[propyl-(4,5,6,7-tetrahydro-benzothiazol-6-yl)-amino]-butyl}-amide (19)

STEP A: 2-(4-Chloro-phenyl)-thiazole-5-carboxylic acid (4-hydroxy-butyl)-amide (19A) is prepared as described for 17A starting with 2-(4-Chloro-phenyl)-thiazole-5-carboxylic acid.

Yield: 95%; ESI-MS: 311 (M+H$^+$).

STEP B: 2-(4-Chloro-phenyl)-thiazole-5-carboxylic acid [4-(4,5,6,7-tetrahydro-benzothiazol-6-ylamino)-butyl]-amide (19B) is prepared from 19A as described for 10.

Yield: 39%; ESI-MS: 447(M+H$^+$).

STEP C: Compound 19 is prepared as described for 10. Educts are 19B and propionaldehyde.

ESI-MS: 489 (M+H$^+$); formula: $C_{24}H_{29}ClN_4OS_2 \times C_4H_4O_4 \times H_2O \times 0.1CH_3CN$ (calculated: C, 54.00; H, 5.67; N, 9.15; found: C, 53.61; H, 5.94; N, 9.53).

Example A19

Cyclohexanecarboxylic acid {4-[propyl-(4,5,6,7-tetrahydro-benzothiazol-6-yl)-amino]-butyl}-amide (20)

STEP A: Preparation of cyclohexanecarboxylic acid (4,4-diethoxy-butyl)-amide (20A) is performed with cyclohexanecarbonyl chloride and 4,4-diethoxy-butylamine as described for 1D. The crude product is obtained in almost quantitative yield.

ESI-MS: 226 (100), 272 (M+H$^+$, 12).

STEP B: Preparation of cyclohexanecarboxylic acid (4-oxo-butyl)-amide (20B).

1.09 g (4 mmol) 20A, 5 mL acetic acid, 2.5 mL 1N aqueous hydrochloric acid and 20 mL ethanol are put together and stirred for 16 hours under argon atmosphere. Ethanol is evaporated. Then the resulting residue is dispersed in dichloromethane and extracted with saturated sodium bicarbonate solution. The organic phase is dried with sodium sulfate and the solvent evaporated in vacuum. The crude product is obtained in almost quantitative yield.

STEP C: Preparation of 20 is performed with 20B as described for 1.

Yield: 67%; ESI-MS: 378 (M+H$^+$); mp: 130° C.; formula: $C_{21}H_{35}N_3OS \times C_4H_4O_4$ (calculated: C, 60.82; H, 7.96; N, 8.51; found: C, 60.63; H, 7.98; N, 8.25).

Example A20

Piperidine-1-carboxylic acid {4-[propyl-(4,5,6,7-tetrahydro-benzothiazol-6-yl)-amino]-butyl}-amide (21)

STEP A: Preparation of piperidine-1-carboxylic acid (4,4-diethoxy-butyl)-amide (21A) is performed with piperidine-1-carbonyl chloride as described for 20A.

ESI-MS: 227 (100), 273 (M+H$^+$, 20).

STEP B: Preparation of piperidine-1-carboxylic acid (4-oxo-butyl)-amide (21B) is performed with 21A as described for 20B.

STEP C: Preparation of 21 is performed with 20B as described for 1.

Yield: 40%; ESI-MS: 379 (M+H$^+$); mp: 71° C.; formula: $C_{20}H_{34}N_4OS \times 1.3 C_4H_4O_4$ (calculated: C, 57.17; H, 7.46; N, 10.58; found: C, 57.19; H, 7.57; N, 10.38).

Example A21

1-Cyclohexyl-3-{4-[propyl-(4,5,6,7-tetrahydro-benzothiazol-6-yl)-amino]-butyl}-urea (22)

STEP A: Preparation of 1-cyclohexyl-3-(4-hydroxy-butyl)-urea (22A) is performed with cyclohexyl isocyanate as described for 1D.

Yield: 97%; ESI-MS: 213 (M+H$^+$).

STEP B: Preparation of 1-cyclohexyl-3-(4-oxo-butyl)-urea (22B) is performed with 22A as described for 1E.

Yield: 91%.

STEP C: Preparation of 22 is performed with 22B as described for 1.

Yield: 27%; ESI-MS: 393 (M+H$^+$); mp: 149° C.; formula: $C_{21}H_{36}N_4OS \times C_4H_4O_4 \times H_2O$ (calculated: C, 57.06; H, 7.97; N, 10.51; found: C, 57.01; H, 8.04; N, 10.64).

Example A22

1,2,3,4-Tetrahydro-naphthalene-2-carboxylic acid {4-[propyl-(4,5,6,7-tetrahydro-benzothiazol-6-yl)-amino]-butyl}-amide (23)

STEP A: Preparation of 1,2,3,4-tetrahydro-naphthalene-2-carbonyl chloride (23A).

6.5 mmol (1.15 g) 1,2,3,4-Tetrahydro-naphthalene-2-carboxylic acid is dissolved in 20 mL toluene, 20 mL of thionyl-chloride are added, the mixture is heated to 60° C. in an oil bath for 2 hours. Then the mixture is concentrated in vacuum. Toluene is added to the residue and evaporated again. The crude product is obtained in almost quantitative yield.

ESI-MS: 131 (100), 159 (82), 196 (M+H$^+$, 82).

STEP B: 1,2,3,4-Tetrahydro-naphthalene-2-carboxylic acid (4,4-diethoxy-butyl)-amide (23B) is prepared from 23A as described for 20A.

ESI-MS: 274 (100), 320 (M+H$^+$, 37).

STEP C: 1,2,3,4-Tetrahydro-naphthalene-2-carboxylic acid (4-oxo-butyl)-amide (23C) is prepared from 23B as described for 20B.

STEP D: 23 is prepared from 23B as described for 1.

Yield: 42%; ESI-MS: 426 (M+H$^+$); mp: 138° C.; formula: $C_{25}H_{35}N_3OS \times C_4H_4O_4$ (calculated: C, 64.30; H, 7.26; N, 7.76; found: C, 64.05; H, 7.20; N, 7.66).

Example A23

3,4-Dihydro-1H-isoquinoline-2-carboxylic acid {4-[propyl-(4,5,6,7-tetrahydro-benzothiazol-6-yl)-amino]-butyl}-amide (24)

STEP A: Preparation of 3,4-dihydro-1H-isoquinoline-2-carbonyl chloride (24A).

To 3.0 g (10 mmol) triphosgene in 30 mL dichloromethane at −80° C. is added 2.32 mL (28.8 mmol) pyridine. Then 3.83 g (28.8 mmol) 1,2,3,4-Tetrahydro-isoquinoline is added over a period of 10 minutes. The reaction mixture is allowed to warm to room temperature and stirred for another 2 hours. 20 mL 1N hydrochloric acid is added for hydrolization. The organic phase is separated, washed with saturated sodium bicarbonate solution and dried with sodium sulfate. After evaporation of the solvent the crude product is purified via column chromatography on silica gel using dichloromethane as eluent.

Yield: 75%; ESI-MS: 134 (100), 160 (8), 196 (M+H$^+$, 12).

STEP B: 3,4-Dihydro-1H-isoquinoline-2-carboxylic acid (4,4-diethoxy-butyl)-amide (24B) is prepared from 24A as described for 20A.

ESI-MS: 275 (100), 321 (M+H$^+$, 28).

STEP C: 3,4-Dihydro-1H-isoquinoline-2-carboxylic acid (4-oxo-butyl)-amide is prepared from 24B as described for 20B.

STEP D: 24 is prepared from 24B as described for 1.

Yield: 26%; ESI-MS: 327 (M+H$^+$); mp: 125° C.; formula: $C_{24}H_{34}N_4OS \times 1.3 C_4H_4O_4$ (calculated: C, 60.73; H, 6.84; N, 9.70; found: C, 60.58; H, 6.95; N, 9.62).

Example A24

6,7-Dimethoxy-3,4-dihydro-1H-isoquinoline-2-carboxylic acid {4-[propyl-(4,5,6,7-tetrahydro-benzothiazol-6-yl)-amino]-butyl}-amide (25)

STEP A: 6,7-Dimethoxy-3,4-dihydro-1H-isoquinoline-2-carbonyl chloride (25A) is prepared from 6,7-Dimethoxy-1,2,3,4-tetrahydro-isoquinoline as described for 24A.

Yield: 94%; ESI-MS: 220 (88), 256 (M+H$^+$, 100).

STEP B: 6,7-Dimethoxy-3,4-dihydro-1H-isoquinoline-2-carboxylic acid (4-hydroxy-butyl)-amide (25B) is prepared from 25A as described for 1D.

Yield: 67%; ESI-MS: 307 (M−H$^+$).

STEP C: 6,7-Dimethoxy-3,4-dihydro-1H-isoquinoline-2-carboxylic acid (4-oxo-butyl)-amide (25C) is prepared from 25B as described for 1E. The crude product is obtained in almost quantitative yield.

STEP D: Compound 25 is prepared from 25C as described for 1.

Yield: 75%; ESI-MS: 487 (M+H+); mp: 106° C.; formula: $C_{26}H_{38}N_4O_3S \times C_4H_4O_4 \times 0.5 H_2O$ (calculated: C, 58.50; H, 7.08; N, 9.16; found: C, 58.90; H, 7.23; N, 8.85).

Example A25

Indane-2-carboxylic acid-{4-[propyl-(4,5,6,7-tetrahydrobenzothiazol-6-yl)amino]butyl}amide (26)

STEP A: Indan-2-carbonyl chloride (26A) is prepared from indan-2-carboxylic acid as described for 23A.

STEP B: Indane-2-carboxylic acid-(4-hydroxybutyl)amide (26B) is prepared from 26A as described for 1D.

Yield: 62%; ESI-MS: 234 (M+H$^+$, 81), 256 (M+Na$^+$, 100).

STEP C: Indane-2-carboxylic acid-(4-oxobutyl)amide (26C) is prepared from 26B as described for 1E.

Yield: 99%.

STEP D: 26 is prepared from 26C as described for 1.

Yield: 36%; ESI-MS: 412 (M+H$^+$); mp: 119° C.; formula: $C_{24}H_{33}N_3OS \times C_4H_4O_4 \times H_2O$ (C, 61.63; H, 7.20; N, 7.70; found: C, 61.49; H, 7.11; N, 7.46).

Example A26

1,3-Dihydro-isoindole-2-carboxylic acid {4-[propyl-(4,5,6,7-tetrahydro-benzothiazol-6-yl)-amino]-butyl}-amide (27)

STEP A: 1,3-Dihydro-isoindole-2-carbonyl chloride (27A) is prepared from 2,3-dihydro-1H-isoindole as described for 24A.

Yield: 77%; ESI-MS: 182 (M+H$^+$).

STEP B: 1,3-Dihydro-isoindole-2-carboxylic acid-(4-hydroxybutyl)amide (27B) is prepared from 27A as described for 1D.

Yield: 97%; ESI-MS: 235 (M+H$^+$, 30), 257 (M+Na$^+$, 100).

STEP C: 1,3-Dihydro-isoindole-2-carboxylic acid (4-oxobutyl)-amide (27C) is prepared from 27B as described for 1E. The crude product is obtained in almost quantitative yield.

STEP D: 27 is prepared from 27C as described for 1.

Yield: 76%; ESI-MS: 413 (M+H$^+$); mp: 118° C.; formula: $C_{23}H_{32}N_4OS \times C_4H_4O_4 \times H_2O$ (C, 59.32; H, 7.01; N, 10.25; found: C, 58.95; H, 7.00; N, 10.10).

Example A27

Naphthalene-2-carboxylic acid {2-[ethyl-(4,5,6,7-tetrahydro-benzothiazol-6-yl)-amino]-ethyl}-amide (32)

STEP A: Preparation of naphthalene-2-carboxylic acid (2-hydroxy-ethyl)-amide (32A).

To a mixture of 3.15 g (30 mmol) 2,2-dimethoxy-ethylamine and 40 mL dioxane is added 1.91 g (10 mmol) naphthalene-2-carbonyl chloride. After stirring overnight the solution is pored into 200 mL of ice water. Filtration yields the product in almost quantitative yield as a white solid.

STEP B: Naphthalene-2-carboxylic acid (2-oxo-ethyl)-amide (32B) is prepared from 32A as described for 20B.

Yield: 39%

STEP C: Compound 32 is prepared from 32B and 1C as described for 1. The salt of oxalic acid is crystallized from ethanol/diethylether.

Yield: 34%; ESI-MS: 380 (M+H$^+$); mp: 110° C.; formula: $C_{22}H_{25}N_3OS \times C_2H_2O_4$ (calculated: C, 61.39; H, 5.80; N, 8.95; found: C, 61.17; H, 5.69; N, 8.73).

Example A28

1-Indan-2-yl-3-{4-[propyl-(4,5,6,7-tetrahydrobenzothiazol-6-yl)amino]butyl}urea (60)

STEP A: Preparation of 2-isocyanatoindan (60A).

A solution of 1.53 g (11.5 mmol) indan-2-ylamine and 1.39 mL (11.5 mmol) in 40 mL dry dioxane is stirred for 2 hours at 70° C. under argon atmosphere and then concentrated under vacuum.

Yield: 85%

STEP B: 1-(4-Hydroxybutyl)-3-indan-2-ylurea (60B) is prepared from 60A as described for 1D.

Yield: 61%; ESI-MS: 249 (M+H$^+$).

STEP C: 1-Indan-2-yl-3-(4-oxobutyl)urea (60C) is prepared from 60B as described for 1E.

The product is obtained in almost quantitative yield.

STEP D: Compound 60 is prepared from 1C and 60C as described for 1. The salt of maleic acid is crystallized from acetonitrile/diethylether.

Yield: 11%; ESI-MS: 427 (M+H$^+$); mp: 93° C.; formula: $C_{24}H_{34}N_4OS \times 1.5C_4H_4O_4 \times 0.5H_2O$ (calculated: C, 59.10; H, 6.78; N, 9.19; found: C, 58.76; H, 6.84; N, 8.86).

Example A29

4-Phenylpiperazine-1-carboxylic acid {4-[propyl-(4,5,6,7-tetrahydrobenzothiazol-6-yl)amino] butyl}amide (61)

STEP A: 4-Phenylpiperazine-1-carbonyl chloride (61A) is prepared from 1-phenylpiperazine as described for 24 A.

Yield: 83%; ESI-MS: 163 (100), 189 (m-Cl$^-$, 75), 225 (M+H$^+$, 44); mp: 79.5° C.

STEP B: 4-Phenylpiperazine-1-carboxylic acid (4,4-diethoxybutyl)amide (61B) is prepared from 61A as described for 20A. The product is obtained in almost quantitative yield.

STEP C: 4-Phenylpiperazine-1-carboxylic acid (4-oxobutyl)amide (61C) is prepared from 61B as described for 20B. The product is obtained in almost quantitative yield.

STEP D: Compound 61 is prepared from 1C and 61C as described for 1. The salt of maleic acid is crystallized from acetonitrile/diethylether.

Yield: 68%; ESI-MS: 456 (M+H$^+$); mp: 120° C.; formula: $C_{25}H_{37}N_5OS \times C_4H_4O_4 \times 1.5H_2O$ (calculated: C, 58.20; H, 7.30; N, 11.48; found: C, 58.17; H, 7.41; N, 11.70).

Example A30

4-Phenyl-3,6-dihydro-2H-pyridine-1-carboxylic acid {4-[propyl-(4,5,6,7-tetrahydrobenzothiazol-6-yl) amino]butyl}amide (62)

STEP A: 4-Phenyl-3,6-dihydro-2H-pyridine-1-carbonyl chloride (62A) is prepared from 4-phenyl-1,2,3,6-tetrahydropyridine as described for 24A.

Yield: 95%; ESI-MS: 160 (M-COCl+2H$^+$, 100), 222 (M+H$^+$, 83); mp: 63° C.

STEP B: 4-Phenyl-3,6-dihydro-2H-pyridine-1-carboxylic acid (4-hydroxybutyl)amide (62B) is prepared from 62A as described for 1D. The product is obtained in almost quantitative yield.

STEP C: 4-Phenyl-3,6-dihydro-2H-pyridine-1-carboxylic acid (4-oxobutyl)amide (62C) is prepared from 62B as described for 1E. The product is obtained in almost quantitative yield.

STEP D: Compound 62 is prepared from 62C and 1C as described for 1. The salt of maleic acid is crystallized from acetonitrile/diethylether.

Yield: 45%; ESI-MS: 456 (M+H$^+$); mp: 115° C.; formula: $C_{26}H_{36}N_4OS \times C_4H_4O_4 \times H_2O$ (calculated: C, 61.41; H, 7.22; N, 9.55; found: C, 61.36; H, 7.26; N, 9.27).

Example A31

N-(4-(4,5,6,7-Tetrahydrobenzo[d]thiazol-6-ylamino)butyl)benzo[d]thiazole-2-carboxamide (63)

STEP A: Preparation of (1,4-Dioxa-spiro[4.5]dec-8-yl)-amine

To a solution of 9.36 g (60 mmol) 1,4-cyclohexanedione monoethylene acetal in 60 mL of methanol which has been saturated with ammonia, 0.6 g of palladium on carbon (10%) is added. The mixture is stirred overnight under 4 bar hydrogen pressure. Filtration over Celite and concentration in vacuum provides the crude product in almost quantitative yield.

STEP B: Preparation of 4,5,6,7-tetrahydro-benzothiazole-2,6-diamine dihydrobromide A solution of 9.43 g (60 mmol) (1,4-dioxa-spiro[4.5]dec-8-yl)amine in 120 mL concentrated aqueous hydrobromic acid is stirred for 15 minutes at room temperature and then 3.12 mL (60 mmol) bromine are added. After further stirring for 15 minutes, 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

STEP C: Preparation of (4,5,6,7-tetrahydro-benzothiazol-6-yl)-amine

To a solution of 12.8 g (38.9 mmol) 4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with Chloroform/Ethanol 5:1 (3×250 mL). The solution is dried over anhydrous sodium sulfate and concentrated in vacuum. The product obtained is chromatographically purified over silica gel, eluting with dichloromethane/methanol

STEP D: Preparation of N-(4-hydroxybutyl)benzothiazole-2-carboxamide 1 g (5 mmol) benzothiazol-2-carbonyl chloride, 542 mg (6 mmol) 4-aminobutan-1-ol and 1.4 g (10 mmol) $K_2CO_3$ in acetonitrile is stirred for three days at room temperature. The solvent is evaporated and the product is dissolved in ethyl acetate and washed with 2N HCl and water. After evaporation of the solvent the yellow semisolid is crystallized from ethyl acetate.

STEP E: Preparation of N-(4-(4,5,6,7-tetrahydrobenzothiazol-6-ylamino)butyl)benzothiazole-2-carboxamide (63)

To a solution of 339 mg (1.4 mmol) N-(4-hydroxybutyl)benzothiazole-2-carboxamide, 198 mg (1.2 mmol) 4,5,6,7-tetrahydro-benzothiazol-6-yl-amine and 210 mg (1.6 mmol) DIPEA in 6 mL of propionitrile is added 0.39 g (1.6 mmol) cyanomethyltrimethylphosphonium iodide under argon. The mixture is heated for 2 hours at 90° C. After cooling down to room temperature 10 mL of saturated $NaHCO_3$ solution and 20 mL of $CH_2Cl_2$ are added. The organic phase is extracted with 10 mL of water three times. After drying and removing of the solvent in vacuum the brown oil received is purified via silica gel chromatography.

Yield: 29%

ESI-MS 387(M+H$^+$, 100); formula: $C_{18}H_{22}N_4OS_2$

Example A32

4-phenyl-N-(4-(propyl-(4,5,6,7-tetrahydrobenzo[d]thiazol-6-yl)amino)butyl)piperidine-1-carboxamide (64)

STEP A: Preparation of (1,4-Dioxa-spiro[4.5]dec-8-yl)-propyl-amine

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N6-propyl-4,5,6,7-tetrahydro-benzothiazole-2,6-diamine dihydrobromide A solution of 12.0 g (60 mmol) (1,4-dioxa-spiro[4.5]dec-8-yl)-propyl-amine in 120 mL concentrated aqueous hydrobromic acid is stirred for 15 minutes at room temperature and then 3.12 mL (60 mmol) bromine are added. After further stirring for 15 minutes 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 64%; ESI-MS: 153 (57), 212 (M+H$^+$, 100).

STEP C: Preparation of propyl-(4,5,6,7-tetrahydro-benzothiazol-6-yl)-amine

To a solution of 14.5 g (38.9 mmol) N6-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with Chloroform/Ethanol 5:1 (3×250 mL). The solution is dried over anhydrous sodium sulfate and concentrated in vacuum. The brown oil obtained is chromatographed over silica gel, eluting with dichloromethane/methanol 97:3 under ammonia atmosphere.

Yield: 66%; ESI-MS: 197 (M+H$^+$).

STEP D: Preparation of
4-phenylpiperidine-1-carbonylchloride

To 0.68 g (2.26 mmol) triphosgene in 6,8 mL dichloromethane at −80° C. is added 0.52 mL (6.5 mmol) pyridine. Then 1.05 g 4-phenylpiperidine (6.5 mmol) is added over a period of 10 minutes. The reaction mixture is allowed to warm to room temperature and stirred for another 2 hours. 4.5 mL 1N hydrochloric acid is added for hydrolization. The organic phase is separated, washed with saturated sodium bicarbonate solution and dried with sodium sulfate. After evaporation of the solvent the crude product is purified via column chromatography on silica gel using dichloromethane as eluent Yield: 96%; ESI-MS: 163 (100), 189 (M-Cl$^-$, 75), 225 (M+H$^+$, 44).

STEP E: Preparation of N-(4,4-diethoxybutyl)-4-phenylpiperidine-1-carboxamide

A solution of 895 mg (4 mmol) of 4-phenylpiperidine-1-carbonylchloride in 4 mL dichloromethane is added to 0.69 mL (4 mmol) 4,4-diethoxybutylamine and 1.68 mL (12 mmol) of triethylamine dissolved in 20 mL of dichloromethane. The mixture is stirred overnight. 20 mL of saturated sodium carbonate solution is added. The organic phase is separated, dried with sodium sulfate and the solvent evaporated.

Yield: 100%; ESI-MS: 303 (100), 371 (M+Na$^+$, 83).

STEP F: Preparation of
N-(4-oxobutyl)-4-phenylpiperidine-1-carboxamide 1.39 g (4 mmol) N-(4,4-diethoxybutyl)-4-phenylpiperidine-1-carboxamide, 5 mL acetic acid, 2.5 mL 1N aqueous hydrochloric acid and 20 mL ethanol are put together and stirred for 16 hours under argon atmosphere. Ethanol is evaporated. Then the resulting residue is dispersed in dichloromethane and extracted with saturated sodium bicarbonate solution. The organic phase is dried with sodium sulfate and the solvent evaporated in vacuum. The crude product is obtained in almost quantitative yield.

STEP G: Preparation of 4-phenyl-N-(4-(propyl-(4,5,6,7-tetrahydrobenzothiazol-6-yl)amino)piperidine-1-carboxamide A solution of 713 mg (2.6 mmol) N-(4-oxobutyl)-4-phenylpiperidine-1-carboxamide and 395 mg (2 mmol) propyl-(4,5,6,7-tetrahydro-benzothiazol-6-yl)-amine in 1,2-dichloroethane (20 mL) is stirred for about 30 minutes. Then 0.75 g (3 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel.

Yield: 34%; ESI-MS: 455 (M+H$^+$, 100); mp: 56° C.; formula:
$C_{26}H_{38}N_4OS \times C_4H_4O_4 \times C_4H^4O_4 \times 0.75H_2O$ (calculated: C, 61,67; H, 7,50; N, 9,59; found C, 61,44; H, 7,37; N, 9,43).

Example A33

N-(4-Propyl-(4,5,6,7-tetrahydrobenzothiazol-6-yl) butyl-adamantyl-1-carboxamide (65)

STEP A: Preparation of
(1,4-dioxa-spiro[4.5]dec-8-yl)-propyl-amine

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N$^6$-propyl-4,5,6,7-tetrahydro-benzothiazole-2,6-diamine dihydrobromide A solution of 12.0 g (60 mmol) (1,4-dioxa-spiro[4.5]dec-8-yl)-propyl-amine in 120 mL concentrated aqueous hydrobromic acid is stirred for 15 minutes at room temperature and then 3.12 mL (60 mmol) bromine are added. After further stirring for 15 minutes, 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 64%; ESI-MS: 153 (57), 212 (M+H$^+$, 100).

STEP C: Preparation of propyl-(4,5,6,7-tetrahydro-benzothiazol-6-yl)-amine

To a solution of 14.5 g (38.9 mmol) N6-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with chloroform/ethanol 5:1 (3×250 mL). The solution is dried over anhydrous sodium sulfate and concentrated in vacuum. The brown oil obtained is chromatographed over silica gel, eluting with dichloromethane/methanol 97:3 under ammonia atmosphere.

Yield: 66%; ESI-MS: 197 (M+H$^+$).

STEP D: Preparation of
N-(4,4-diethoxybutyl)adamantylcarboxamide

A solution of 1.19 g (6 mmol) adamantyl-1-carboxylicacid chloride in 6 mL of dichloromethane is added to 1.04 mL (6 mmol) 4,4-diethoxybutyl-1-amine and 2.52 mL (18 mmol) of triethylamine dissolved in 30 mL of dichloromethane. The mixture is stirred overnight. 30 mL of saturated sodium carbonate solution is added. The organic phase is separated, dried with sodium sulfate and the solvent evaporated.

Yield: 100%

STEP E: Preparation of N-(4-oxobutyl-)adamantylcarboxamide 1.94 g (6 mmol) N-(4,4-diethoxybutyl)adamantylcarboxamide, 7.5 mL of acetic acid, 3.75 mL of 1N aqueous hydrochloric acid and 30 mL ethanol are put together and stirred for 16 hours under argon atmosphere. Ethanol is evaporated. Then the resulting residue is dispersed in dichloromethane and extracted with saturated sodium bicarbonate solution. The organic phase is dried with sodium sulfate and the solvent evaporated in vacuum.

Yield: 92% ESI-MS: 250 (M+H$^+$, 100).

STEP F: Preparation of 5-(Propyl-(4,5,6,7-tetrahydrobenzothiazol-6-yl)amino)pentanecarboxylicacidadamantane-1-ylamide A solution of 395 mg (2 mmol) propyl-(4,5,6,7-tetrahydrobenzothiazol-6-yl)-amine and 748 mg (3 mmol) N-(4-oxobutyl-)adamantylcarboxamide in 1,2-dichloroethane (20 mL) is stirred for about 30 minutes. Then 0.75 g (3.5 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel.

Yield: 53%; ESI-MS: 430 (M+H$^+$, 100); mp: 114° C.; formula: C25H39N3OS×C2H2O4×H2O (calculated: C, 60.31; H, 8.06; N, 7.81; found:: C, 59.96; H, 7.82; N, 7.46).

Example B

The inventors synthesized 7 further compounds according to the present invention by employing the methods set out below in Examples B1 to B7 with reference, where appropriate, to methods described in the Synthetic Methods section which follows.

Example B1

5-[Propyl-(4,5,6,7-tetrahydro-benzothiazol-6-yl)-amino]-pentanoic acid naphthalen-2-ylamide (9)

STEP A: 5-Bromo-pentanoic acid naphthalen-2-ylamide (9A) may be prepared from naphthoylchloride and 5-bromopentanoyl chloride as described for 1D. The crude product is obtained in almost quantitative yield.

STEP B: 9 is prepared from 1C and 9A using the same method as for 6 with acetone as solvent and triethylamine as base. Reaction temperature is 50° C. After evaporation of the solvent the residue is suspended in water, alkalized with sodium hydroxide solution and extracted three times with dichloromethane. After evaporation of the combined organic phases the product is crystallized as salt of maleic acid from acetonitrile/diethylether.

Yield: 11%; ESI-MS: 422 (M+H$^+$); mp: 85° C.; formula: C25H31N3OS×C4H4O4 (calculated: C, 64.78; H, 6.56; N, 7.82; found: C, 64.56; H, 6.75; N, 7.56).

Example B2

N-Propyl-4-{[propyl-(4,5,6,7-tetrahydrobenzothiazol-6-yl)amino]methyl}-N-(4,5,6,7-tetrahydrobenzothiazol-6-yl)benzamide (42)

STEP A: Preparation of 4-{[Propyl-(4,5,6,7-tetrahydrobenzothiazol-6-yl)amino]methyl}benzoic acid methyl-ester (42A). 42A is prepared from 4-formyl-benzoic acid methyl ester and 1C as described for 1.

Yield: 74%; ESI-MS: 345 (M+H$^+$).

STEP B: Preparation of 4-{[propyl-(4,5,6,7-tetrahydrobenzothiazol-6-yl)-amino]-methyl}-benzoic acid (42B).

A mixture of 1.93 g (5.6 mmol) 42A, 840 mg (21 mmol) sodium hydroxide and 25 mL water is stirred for 4 hours at 80° C. The mixture is allowed to cool to room temperature and then neutralized with acetic acid and extracted three times with dichloromethane. The combined organic fractions are dried with sodium sulfate, and the solvent is evaporated in vacuum.

Yield: 97%

STEP C: 4-{[Propyl-(4,5,6,7-tetrahydro-benzothiazol-6-yl)-amino]-methyl}-benzoyl chloride (42C) is prepared from 42B as described for 23A. The crude product is obtained in almost quantitative yield.

STEP D: Compound 42 is prepared from 42C and IC-CORRECT? as described for 1D.

Yield: 74%; ESI-MS: 509 (M+H$^+$); mp: 85° C.; formula: C28H36N4OS2 (calculated: C, 66.10; H, 7.13; N, 11.01; found: C, 65.95; H, 7.14; N, 10.88).

Example B3

(4-Phenylpiperazin-1-yl)-(4-{[propyl-(4,5,6,7-tetrahydrobenzothiazol-6-yl)amino]methyl}phenyl)methanone (43)

Compound 43 is prepared from 42C and 1-phenyl-piperazine as described for 1D.

Yield: 59%; ESI-MS: 475 (M+H$^+$); mp: 70° C.; formula: C28H34N4OS×0.5H2O (calculated: C, 69.53; H, 7.29; N, 11.58; found: C, 69.50; H, 7.10; N, 11.69).

Example B4

N-Indan-2-yl-4-{[propyl-(4,5,6,7-tetrahydrobenzothiazol-6-yl)amino]methyl}benzamide (44)

Compound 44 is prepared from 42C and indan-2-ylamine hydrochloride as described for 1D.

Yield: 58%; ESI-MS: 446 (M+H$^+$); mp: 65° C.; formula: C27H31N3OS (calculated: C, 72.77; H, 7.01; N, 9.43; found: C, 72.60; H, 7.00; N, 9.28).

Example B5

1-(4-Phenylpiperazin-1-yl)-5-(propyl-(4,5,6,7-tetrahydrobenzothiazol-6-yl)amino)pentan-1-one (66)

STEP A: Preparation of (1,4-dioxa-spiro[4.5]dec-8-yl)-propyl-amine

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N$^6$-propyl-4,5,6,7-tetrahydro-benzothiazole-2,6-diamine dihydrobromide A solution of 12.0 g (60 mmol) (1,4-dioxa-spiro[4.5]dec-8-yl)-propyl-amine in 120 mL of concentrated aqueous hydrobromic acid is stirred for 15 minutes at room temperature and then 3.12 mL (60 mmol) bromine are added. After further stirring for 15 minutes, 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 64%; ESI-MS: 153 (57), 212 (M+H$^+$, 100).

STEP C: Preparation of propyl-(4,5,6,7-tetrahydro-benzothiazol-6-yl)-amine

To a solution of 14.5 g (38.9 mmol) N6-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with chloroform/ethanol 5:1 (3×250 mL). The solution is dried over anhydrous sodium sulfate and concentrated in vacuum. The brown oil obtained is chromatographically purified over silica gel, eluting with dichloromethane/methanol 97:3 under ammonia atmosphere.

Yield: 66%; ESI-MS: 197 (M+H$^+$).

STEP D: Preparation of 5-hydroxy-1-(4-phenylpiperazin-1-yl)pentan-1-one

A solution of 5.4 mL (37.5 mmol) Et$_3$N in 10 ml, 2-dichloroethane was added drop by drop under ice cooling to a suspension of 3.70 g (27.5 mmol) AlCl$_3$ in 20mL dichloroethane. At room temperature a solution of 4.21 ml (27.5 mmol) 1-phenylpiperazine and 2.32 mL (25 mmol) delta-valerolactone in 15 mL 1,2-dichloroethane was added to the mixture. After one hour of stirring at room temperature the mixture was quenched with ice water and stirred for another 30 minutes. The suspension was filtered by Celite. After adding of dichloromethane, separating of the organic layer, washing it with water, drying it with Na$_2$SO$_4$ and evaporating of the solvent, followed.

Yield: 93%; ESI-MS: 263 (M+H$^+$, 100).

STEP E: Preparation of 5-oxo-5-(4-phenylpiperazin-1-yl)pentanal

A solution of 1.11 mL (12.8 mmol) oxalyl chloride in 35 mL of dichloromethane is cooled to −80° C. under argon atmosphere. 2.33 mL (32.7 mmol) of dimethylsulfoxide in 9.33 mL of dichloromethane is introduced dropwise over 10 minutes. After 5 minutes a solution of 1.84 (7 mmol) 5-hydroxy-1-(4-phenylpiperazin-1-yl)pentan-1-one in 8 mL dichloromethane and 2 mL dimethylsulfoxide is added over the course of 10 minutes. The reaction mixture is stirred for another hour at −80° C. before 5 mL of triethylamine is added and the mixture is allowed to warm up to room temperature. 50 mL of saturated brine solution is added for hydrolysis. The organic phase is separated, extracted three times with a saturated solution of sodium chloride, dried over sodium sulfate and the solvent is evaporated. The crude product is obtained in almost quantitative yield.

STEP F: Preparation of 1-(4-phenylpiperazin-1-yl)-5-(propyl-(4,5,6,7-tetrahydrobenzothiazol-6-yl)amino)pentan-1-one A solution of 395 mg (2 mmol) propyl-(4,5,6,7-tetrahydrobenzothiazol-6-yl)-amine and 781 mg (3 mmol) 5-oxo-5-(4-phenylpiperazin-1-yl)pentanal in 1,2-dichloroethane (20 mL) is stirred for about 30 minutes. Then 0.75 g (3 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel.

Yield: 67%; ESI-MS: 441 (M+H$^+$, 100); mp: 75° C.; formula: C25H36N4OS×1.25C4H4O4×0.5H2O (calculated: C, 60.59; H, 7.12; N, 9.42; found: C, 60.37; H, 7.24; N, 9.28).

Example B6

N-(2,3-dihydro-1H-inden-2-yl)-5-(propyl-(4,5,6,7-tetrahydrobenzothiazol-6-yl)amino)pentanamide (67)

STEP A: Preparation of (1,4-dioxa-spiro[4.5]dec-8-yl)-propyl-amine

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N$^6$-propyl-4,5,6,7-tetrahydro-benzothiazole-2,6-diamine dihydrobromide A solution of 12.0 g (60 mmol) (1,4-dioxa-spiro[4.5]dec-8-yl)-propyl-amine in 120 mL concentrated aqueous hydrobromic acid is stirred for 15 minutes at room temperature and then 3.12 mL (60 mmol) bromine are added. After further stirring for 15 minutes, 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 64%; ESI-MS: 153 (57), 212 (M+H$^+$, 100).

STEP C: Preparation of propyl-(4,5,6,7-tetrahydro-benzothiazol-6-yl)-amine

To a solution of 14.5 g (38.9 mmol) N6-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with Chloroform/Ethanol 5:1 (3×250 mL). The solution is dried over anhydrous sodium sulfate and concentrated in vacuum. The brown oil obtained is chromatographed over silica gel, eluting with dichloromethane/methanol 97:3 under ammonia atmosphere.

Yield: 66%; ESI-MS: 197 (M+H$^+$).

STEP D: Preparation of N-(indan-2-yl)-5-hydroxypentanamide

A solution of 2.7 mL (18.75 mmol) of Et$_3$N in 5 mL of 1,2-dichloroethane was added drop by drop under ice cooling to a suspension of 1.85 g (13.75 mmol) AlCl$_3$ in 10 mL of dichloroethane. At room temperature a solution of 2.33 g (13.75 mmol) 2-aminoindane HCl (and Et$_3$N for the solvation of the hydrochloride) and 1.16 mL (12.5 mmol) delta-valerolactone in 7.5 mL 1,2-dichloroethane was added to the mixture. After one hour of stirring at room temperature the mixture was quenched with ice water and stirred for another 30 minutes. The suspension was filtered by Celite. After adding of dichloromethane, separating of the organic layer, washing it with water, drying it with $Na_2SO_4$ and evaporating of the solvent, followed.

Yield: 100%; ESI-MS: 234 (M+H$^+$, 100).

STEP E: Preparation of N-(indan-2-yl)-5-oxopentanamide

A solution of 1.11 mL (12.8 mmol) oxalyl chloride in 35 mL of dichloromethane is cooled to −80° C. under argon atmosphere. 2.33 mL (32.7 mmol) of dimethylsulfoxide in 9.33 mL of dichloromethane is introduced dropwise over 10 minutes. After 5 minutes a solution of 1.63 g (7 mmol) N-(2,3-dihydro-1H-inden-2-yl)-5-hydroxypentanamide in 8 mL dichloromethane and 2 mL dimethylsulfoxide is added over the course of 10 minutes. The reaction mixture is stirred for another hour at −80° C. before 5 mL of triethylamine is added and the mixture is allowed to warm up to room temperature. 50 mL of saturated brine solution is added for hydrolysis. The organic phase is separated, extracted three times with a saturated solution of sodium chloride, dried over sodium sulfate and the solvent is evaporated.

Yield: 99%

STEP F: Preparation of N-(indan-2-yl)-5-(propyl-(4,5,6,7-tetrahydrobenzothiazol-6-yl)amino)pentanamide A solution of 395 mg (2 mmol) propyl-(4,5,6,7-tetrahydro-benzothiazol-6-yl)-amine and 694 mg (3 mmol) N-(2,3-dihydro-1H-inden-2-yl)-5-oxopentanamide in 1,2-dichloroethane (20 mL) is stirred for about 30 minutes. Then 0.75 g (3 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel.

Yield: 66%; ESI-MS: 412 (M+H$^+$, 100); mp: 60° C.; formula: C24H33N3OS×1.25C4H4O4×0.75H2O (calculated: C, 61.09; H, 6.98; N, 7.37; found: C, 61.15; H, 7.11; N, 7.06).

Example B7

N-Adamantanyl-5-(propyl-(4,5,6,7-tetrahydrobenzothiazol-6-yl)amino)pentanamide (68)

STEP A: Preparation of (1,4-dioxa-spiro[4.5]dec-8-yl)-propyl-amine

To a solution of 9.36 g (60 mmol) 1,4-cyclohexanedione monoethylene acetal in 60 mL of methanol and 9.84 mL (120 mmol) of propylamine is added 0.6 g of palladium on carbon (10%). The mixture is stirred overnight under 4 bar hydrogen pressure. Filtration over Celite and concentration in vacuum provides the crude product in almost quantitative yield.

ESI-MS: 141 (12), 200 (M+H$^+$, 100).

STEP B: Preparation of N$^6$-propyl-4,5,6,7-tetrahydro-benzothiazole-2,6-diamine dihydrobromide A solution of 12.0 g (60 mmol) (1,4-dioxa-spiro[4.5]dec-8-yl)-propyl-amine in 120 mL concentrated aqueous hydrobromic acid is stirred for 15 minutes at room temperature and then 3.12 mL (60 mmol) bromine are added. After further stirring for 15 minutes 4.56 g (60 mmol) of thiourea is added. The resulting solution is stirred for another at room temperature until a white precipitation can be observed. Afterwards the mixture is heated for 2 hours at 90° C. The clear reaction mixture is then concentrated under vacuum. The solid residue is suspended in ethanol, heated to reflux and filtrated after cooling to room temperature. The resulting residue is dried under high vacuum.

Yield: 64%; ESI-MS: 153 (57), 212 (M+H$^+$, 100).

STEP C: Preparation of propyl-(4,5,6,7-tetrahydro-benzothiazol-6-yl)-amine

To a solution of 14.5 g (38.9 mmol) N$^6$-propyl-4,5,6,7-tetrahydro-benzothiazole-2,6-diamine dihydrobromide in 220 mL concentrated aqueous hydrochloric acid at −30° C. is drop wise added 66.3 mL of an aqueous 1N solution nitrite over the course of 30 minutes. After further stirring for 1 hour at the same temperature 5.44 ml (52.5 mmol) of a 50% aqueous solution hypophosphoric acid is added. The reaction mixture is stored at 4° C. overnight. After having cooled down the solution again to −30° C. the mixture is slowly basified with 40% aqueous sodium hydroxide solution while temperature is kept at −30° C. The resulting mixture is warmed up to room temperature and extracted with chloroform/ethanol 5:1 (3×250 mL). The solution is dried over anhydrous sodium sulfate and concentrated in vacuum. The brown oil obtained is chromatographically purified over silica gel, eluting with dichloromethane/methanol 97:3 under ammonia atmosphere.

Yield: 66%; ESI-MS: 197 (M+H$^+$).

STEP D: Preparation of N-adamantyl-5-hydroxypentanamide

A solution of 3.6 mL (25 mmol) of Et$_3$N in 6.7 mL of 1,2-dichloroethane was added drop by drop under ice cooling to a suspension of 2.47 g (18.3 mmol) AlCl$_3$ in 13.3 mL of dichloroethane. At room temperature a solution of 2.77 g (18.3 mmol) adamantane and 1.55 mL (16.7 mmol) delta-valerolactone in 10 mL of 1,2-dichloroethane was added to the mixture. After one hour of stirring at room temperature the mixture was quenched with ice water and stirred for another 30 minutes. The suspension was filtered by Celite. After addition of dichloromethane, separation of the organic layer, washing it with water, drying it with $Na_2SO_4$ and the solvent was evaporated. The product can be taken for further reactions.

Yield: 72%; ESI-MS: 252 (M+H$^+$).

STEP E: Preparation of N-adamantyl-5-oxopentanamide

A solution of 1.11 mL (12.8 mmol) oxalyl chloride in 35 mL of dichloromethane is cooled to −80° C. under argon atmosphere. 2.33 mL (32.7 mmol) of dimethylsulfoxide in 9.33 mL of dichloromethane is introduced dropwise over 10 minutes. After 5 minutes a solution of 1.76 g (7 mmol) N-adamantyl-5-hydroxypentanamide in 8 mL dichloromethane and 2 mL dimethylsulfoxide is added over the course of 10 minutes. The reaction mixture is stirred for another hour at −80° C. before 5 mL of triethylamine is added and the mixture is allowed to warm up to room temperature. 50 mL of saturated brine solution is added for hydrolysis. The organic phase is separated, extracted three times with a saturated solution of sodium chloride, dried over sodium sulfate and the solvent is evaporated.

Yield: 99%

STEP F: Preparation of N-adamantanyl-5-(propyl(4,5,6,7-tetrahydrobenzothiazol-6-yl)amino)pentanamide A solution of 395 mg (2 mmol) propyl-(4,5,6,7-tetrahydro-benzothiazol-6-yl)-amine and 748 mg (3 mmol) N-adamantyl-5-oxopentanamide in 1,2-dichloroethane (20 mL) is stirred for about 30 minutes. Then 0.75 g (3 mmol) of sodium triacetoxyborohydride is added and the mixture is stirred overnight. After hydrolysation with 30 mL of 1N aqueous NaOH solution the organic phase is separated, dried over sodium sulfate and concentrated in vacuum. The crude product obtained is purified via column chromatography on silica gel.

Yield: 60%; ESI-MS: 430 (M+H$^+$, 100); mp: 145° C.; formula: C25H39N3OS×1.25C4H4O4×0.75H2O (calculated: C, 61.25; H, 7.80; N, 7.14; found: C, 61.41; H, 7.91; N, 7.05).

Example C

The inventors synthesized 11 further compounds according to the present invention by employing the methods set out below in Examples C1 to C11 with reference, where appropriate, to methods described in the Synthetic Methods section which follows.

Example C1

Ethyl-{2-[4-(2-methoxy-phenyl)-piperazin-1-yl]-ethyl -(4,5,6,7-tetrahydro-benzothiazol-6-yl)-amine (28)

STEP A: Preparation of 2-[4-(2-methoxy-phenyl)-piperazin-1-yl]ethanol (28A).

A mixture of 2.29 g (10 mmol) 1-(2-methoxy-phenyl)-piperazine hydrochloride, 7.1 mL (100 mmol) 2-bromo-ethanol, 5.52 g (40 mmol) potassium carbonate and 100 mL acetonitrile is stirred at 60° C. overnight. Filtration and concentration in vacuum yields the crude product which is purified via column chromatography over silica gel eluting with dichloromethane/ammonia-saturated methanol 98:2.

Yield: 95%; ESI-MS: 237 (M+H$^+$).

STEP B: [4-(2-Methoxy-phenyl)-piperazin-1-yl]-acetaldehyde (28B) is prepared from 28A as described for 1E.

STEP C: Compound 28 is prepared from 28B and 4C as described for 1.

The salt of maleic acid is crystallized from ethanol/diethylether.

Yield: 50%; ESI-MS: 401 (M+H$^+$); mp: 108° C.; formula: C22H32N4OS×2C4H4O4 (calculated: C, 56.95; H, 6.37; N, 8.85; found: C, 56.66; H, 6.45; N, 8.60).

Example C2

Ethyl-{3-[4-(2-methoxy-phenyl)-piperazin-1-yl]-propyl}-(4,5,6,7-tetrahydro-benzothiazol-6-yl)-amine (29)

STEP A: 3-[4-(2-Methoxy-phenyl)-piperazin-1-yl]-propan-1-ol (29A) is prepared as described for 28A from 3-chloro-propan-1-ol with acetone as solvent and under addition of 1.66 g (10 mmol) potassium iodide. The mixture is heated to reflux.

Yield: 46%, ESI-MS: 251 (M+H$^+$).

STEP B: 3-[4-(2-Methoxy-phenyl)-piperazin-1-yl]-propionaldehyde (29B) is prepared from 29A as described for 1E.

STEP C: Compound 29 is prepared from 29B and 1C as described for 1. The salt of maleic acid is crystallized from ethanol/diethylether.

Yield: 10%; ESI-MS: 415 (M+H$^+$); mp: 64° C.; formula: C23H34N4OS×2C4H4O4 (calculated: C, 57.57; H, 6.55; N, 8.66; found: C, 57.33; H, 6.80; N, 8.42).

Example C3

Ethyl-{4-[4-(2-methoxy-phenyl)-piperazin-1-yl]-butyl}-(4,5,6,7-tetrahydro-benzothiazol-6-yl)-amine (30)

STEP A: 4-[4-(2-Methoxy-phenyl)-piperazin-1-yl]-butan-1-ol (30A) is prepared from 4-chloro-butan-1-ol as described for 29A.

Yield: 33%; ESI-MS: 265 (M+H$^+$).

STEP B: 4-[4-(2-Methoxy-phenyl)-piperazin-1-yl]-butyraldehyde (30B) is prepared from 30A as described for 1E.

STEP C: Compound 30 is prepared from 30A and 1C as described for 1. The salt of oxalic acid is crystallized from ethanol/diethylether.

Yield: 25%; ESI-MS: 429.2 (M+H$^+$, 100), 247.0 (C15H23N2O$^+$, 92); mp: 164° C.; formula: C24H36N4OS×2C2H2O4 (calculated: C, 55.25; H, 6.62; N, 9.20; found: C, 55.25; H, 6.53; N, 8.97).

Example C4

[2-(3,4-Dihydro-1H-isoquinolin-2-yl)-ethyl]-ethyl-(4,5,6,7-tetrahydro-benzothiazol-6-yl)-amine (31)

STEP A: 2-(3,4-Dihydro-1H-isoquinolin-2-yl)-ethanol (31A) is prepared from 1,2,3,4-tetrahydro-isoquinoline as described for 28A.

Yield: 60%; ESI-MS: 178 (M+H$^+$).

STEP B: (3,4-Dihydro-1H-isoquinolin-2-yl)-acetaldehyde (31B) is prepared from 31A as described for 1E.

STEP C: Compound 31 is prepared from 31B as described for 1. The salt of oxalic acid is crystallized from acetonitrile.

Yield: 53%; ESI-MS: 160 (18); 209 (10); 342 (M+H$^+$, 100); mp: 193° C.; formula: C20H27N3S×2C2H2O4 (calculated: C, 55.27; H, 5.99; N, 8.06; found: C, 55.24; H, 5.94; N, 7.91).

Example C5

N,N'-Diethyl-N,N'-bis-(4,5,6,7-tetrahydro-benzothiazol-6-yl)-ethane-1,2-diamine (33)

STEP A: N,N'-Diethyl-N,N-bis-(4,5,6,7tetrahydro-benzothiazol-6-yl)-oxalamide (33A) is prepared from 1C (2 equivalents) and oxalylchloride (1 equivalent) as described for 1D.

Yield: 81%

STEP B: Preparation of 33.

To a solution of 1.67 g (4 mmol) 33A in 60 mL tetrahydrofuran are 18 mL of a 1M solution borane tetrahydrofuran complex in THF under an argon atmosphere. After refluxing for 2 hours the mixture is hydrolyzed with water and concentrated in vacuum. The resulting residue is dissolved again in tetrahydrofuran/methanol. After addition of 1.6 mL (16 mmol) 2-(dimethylamino)ethanol the mixture is stirred for 2 hours at 80° C. The solvents are evaporated again and the crude product obtained is purified via column chromatography over silica gel eluting with dichloromethane/ammonia-saturated methanol 98:2. The salt of oxalic acid is crystallized from 2-propanol.

Yield: 23%; ESI-MS: 391 (M+H$^+$); mp: 83° C.; formula: C20H30N4S2×2C2H2O4 (calculated: C, 50.51; H, 6.01; N, 9.82; found: C, 50.31; H, 6.03; N, 9.56).

Example C6

{2-[4-(2-Methoxy-phenyl)-piperazin-1-yl]-ethyl}-propyl-(4,5,6,7-tetrahydro-benzothiazol-6-yl)-amine (34)

Compound 34 is prepared from 1D and 28B as described for 1. The salt of oxalic acid is crystallized from acetonitrile/diethylether.

Yield: 84%; ESI-MS: 415 (M+H$^+$, 100), 218.7 (11); mp: 135.6° C.; formula: C$_{23}$H$_{34}$N$_4$OS×2C$_2$H$_2$O$_4$ (calculated: C, 54.53; H, 6.44; N, 9.42; found: C, 54.30; H, 6.47; N, 9.64).

Example C7

{2-[4-(2,3-Dichloro-phenyl)-piperazin-1-yl]-ethyl}-propyl-(4,5,6,7-tetrahydro-benzothiazol-6-yl)-amine (35)

STEP A: 2-[4-(2,3-Dichloro-phenyl)-piperazin-1-yl]ethanol (35A) is prepared from 1-(2,3-dichloro-phenyl)-piperazine hydrochloride as described for 28A.

Yield: 97%; 275 (M+H$^+$, 100), 277 (M+H$^+$, 62).

STEP B: [4-(2,3-Dichloro-phenyl)-piperazin-1-yl]-acetaldehyde (35B) is prepared from 35A as described for 1E.

STEP C: Compound 35 is prepared from 35B as described for 1. The base of 35 crystallizes from acetonitrile.

Yield: 57%; ESI-MS: 223 (30), 257 (42), 259 (27), 453 (M+H$^+$, 100), 455 (M+H$^+$, 74); mp: 103.5° C.; formula: C$_{22}$H$_{30}$Cl$_2$N$_4$S (calculated: C, 58.27; H, 6.67; N, 12.36; found: C, 58.12; H, 6.67; N, 12.62).

Example C8

{3-[4-(2,3-Dichloro-phenyl)-piperazin-1-yl]-propyl}-propyl-(4,5,6,7-tetrahydro-benzothiazol-6-yl)-amine (36)

STEP A: 3-[4-(2,3-Dichloro-phenyl)-piperazin-1-yl]propan-1-ol (36A) is prepared from 1-(2,3-dichloro-phenyl)-piperazine hydrochloride as described for 29A.

Yield: 82%; ESI-MS: 289 (M+H$^+$, 100), 291 (M+H$^+$, 67).

STEP B: 3-[4-(2,3-Dichloro-phenyl)-piperazin-1-yl]-propionaldehyde (36B) is prepared from 36A as described for 1E.

STEP C: Compound 36 is prepared from 36B as described for 1. The salt of maleic acid is crystallized from ethanol/diethylether.

Yield: 19%; ESI-MS: 467 (M+H$^+$, 100), 469 (M+H$^+$, 69); mp: 110° C.; formula: C$_{23}$H$_{32}$Cl$_2$N$_4$S×2C$_4$H$_4$O$_4$×0.75H$_2$O (calculated: C, 52.21; H, 5.87; N, 7.86; found: C, 51.92; H, 5.97; N, 7.47).

Example C9

{4-[4-(2,3-Dichloro-phenyl)-piperazin-1-yl]-butyl}-propyl-(4,5,6,7-tetrahydro-benzothiazol-6-yl)-amine (37)

STEP A: 4-[4-(2,3-Dichloro-phenyl)-piperazin-1-yl]-butan-1-ol (37A) is prepared from 1-(2,3-dichloro-phenyl)-piperazine hydrochloride as described for 30A.

Yield: 81%; ESI-MS: 303 (M+H$^+$, 100), 305 (M+H$^+$, 66).

STEP B: 4-[4-(2,3-Dichloro-phenyl)-piperazin-1-yl]-butyraldehyde (37B) is prepared from 37A as described for 1E.

STEP C: Compound 37 is prepared from 37B as described for 1. The salt of oxalic acid is crystallized from ethanol/diethylether.

Yield: 37%; ESI-MS: 481 (M+H$^+$, 100), 483 (M+H$^+$, 71); mp: 150° C.; formula: C$_{24}$H$_{34}$Cl$_2$N$_4$S×2C$_2$H$_2$O$_4$ (calculated: C, 50.83; H, 5.79; N, 8.47; found: C, 50.55; H, 6.02; N, 8.20).

Example C10

[2-(4-Benzoyl-piperazin-1-yl)-ethyl]-propyl-(4,5,6,7-tetrahydro-benzothiazol-6-yl)-amine (38)

STEP A: 2-(4-Benzoyl-piperazin-1-yl)-ethanol (38A) is prepared from 1-benzoyl-piperazine as described for 28A.

Yield: 90%; 235 (M+H$^+$).

STEP B: (4-Benzoyl-piperazin-1-yl)-acetaldehyde (38B) is prepared from 38A as described for 1E.

STEP C: Compound 38 is prepared from 38B as described for 1. The salt of oxalic acid is crystallized from acetonitrile.

Yield: 62%; ESI-MS: 217 (84), 223 (31), 413 (M+H$^+$, 100); mp: 186° C.; formula: C$_{23}$H$_{32}$N$_4$OS×2C$_2$H$_2$O$_4$×0.75H$_2$O (calculated: C, 53.50; H, 6.24; N, 9.24; found: C, 53.44; H, 6.19; N, 9.28).

Example C11

[2-(4-Naphthoyl-piperazin-1-yl)-ethyl]-propyl-(4,5,6,7-tetrahydro-benzothiazol-6-yl)-amine (39)

STEP A: Preparation of 1-naphthoyl-piperazine hydrochloride (39A).

To a solution of 30 g (0.35 mol) piperazine in 300 mL dichloromethane is added a solution of 10 g (52 mmol) naphthalene-2-carbonyl chloride in 100 mL dichloromethane. After stirring for 2 hours the mixture is extracted 5 times with brine solution and dried over sodium sulfate. The salt of hydrochloric acid is crystallized from dichloromethane.

Yield: 40%.

STEP B: 2-(4-Naphthoyl-piperazin-1-yl)-ethanol (39B) is prepared from 39A as described for 28A.

Yield: 30%; ESI-MS: 285 (M+H$^+$).

STEP C: (4-Naphthoyl-piperazin-1-yl)-acetaldehyde (39C) is prepared from 39B as described for 1E.

STEP D: Compound 39 is prepared from 39C as described for 1. The salt of maleic acid is crystallized from ethanol/diethylether.

Yield: 64%; ESI-MS: 463 (M+H$^+$); mp: 85° C.; formula: C$_{27}$H$_{34}$N$_4$OS×2C$_4$H$_4$O$_4$×0.75H$_2$O (calculated: C, 59.35; H, 6.19; N, 7.91; found: C, 59.16; H, 6.23; N, 7.60).

Example D

The inventors synthesized 1 further compound according to the present invention by employing the methods set out below in Example D1 with reference, where appropriate, to methods described in the Synthetic Methods section which follows.

Example D1

N-(2-Phenoxyethyl)-N-propyl-4,5,6,7-tetrahydrobenzothiazol-6-amine (69)

STEP A: Preparation of 2-phenoxyacetaldehyde diethyl acetal (69A)

0.94 g (10 mmol) of phenol, 1.52 g (10 mmol) of chloroacetaldehyde diethyl acetal, 2.77 g (20 mmol) of potassium carbonate, 500 mg of potassium iodide and 5 ml of dimethylformamide were heated for 1 hour at 175° C. under microwave conditions. The mixture was then diluted with 2M aqueous sodium hydroxide solution and extracted with dichloromethane. The organic layer was dried with sodium sulfate and the solvent evaporated in vacuum. The crude product was obtained in almost quantitative yield.

ESI-MS: 211 (M+H$^+$).

STEP B: Preparation of 2-phenoxyacetaldehyde (69B)

0.84 g (4 mmol) of 69A, 5 mL of acetic acid, 2.5 mL of 1N aqueous hydrochloric acid and 20 mL of ethanol were mixed and heated under reflux under an argon atmosphere for 3 hours. Ethanol was evaporated. Then the resulting residue was dispersed in dichloromethane and extracted with saturated sodium bicarbonate solution. The organic phase was dried with sodium sulfate and the solvent evaporated in vacuum. The crude product was obtained in almost quantitative yield.

ESI-MS: 137 (M+H$^+$).

STEP C: Preparation of N-(2-phenoxyethyl)-N-propyl-4,5,6,7-tetrahydrobenzothiazol-6-amine (69)

A solution of 395 mg (2 mmol) propyl-(4,5,6,7-tetrahydrobenzothiazol-6-yl)-amine (1C) and 340 mg (2.5 mmol) 2-phenoxyacetaldehyde (69B) in 1,2-dichloroethane (20 mL) was stirred for about 30 minutes. Then 0.75 g (3 mmol) of sodium triacetoxyborohydride was added and the mixture was stirred overnight. After hydrolysation with 30 mL of 1N aqueous NaOH solution the organic phase was separated, dried over sodium sulfate and concentrated in vacuum. The crude product obtained was purified twice via column chromatography on silica gel eluting with dichloromethane/methanol (98:2). The methanol used was saturated with NH$_3$-gas. Evaporation of the solvent yields 1.23 mmol (387 mg) of a colourless oil. The salt of oxalic acid is crystallized from acetonitrile.

Yield: 26% (oil); ESI-MS: 317 (M+H$^+$); mp: 136° C.; formula: $C_{22}H_{24}N_2OS \times 2C_2H_2O_4 \times H_2O$ (calculated: C, 51.35; H, 5.88; N, 5.44; found: C, 51.55; H, 5.88; N, 5.12).

Example E

Receptor Binding Assays

Compounds synthesized in Examples A, B, C and D were assayed to test their affinity for dopamine D3 and D2 receptors.

METHODS: Dopamine $D_{2S}$ and $D_3$ Receptor Binding Assays

Cell Culture

CHO-$D_{2S}$ cells, expressing the recombinant human $D_2$(short) dopamine receptor gene, (Hayes, G. et al., *J. Mol. Endocrinol.* 1992, 6, 920-926) were grown in Dulbecco's modified Eagle's medium/nutrient mixture F12 1:1 mixture supplemented with 2 mM glutamine, 10% fetal bovine serum, and 10 µl·ml$^{-1}$ penicillin/streptomycin in an atmosphere of 5% $CO_2$ at 37° C. (Gibco™, Karlsruhe, Germany).

Human $D_3$ receptors stably expressed in CHO cells were used as described by Sokoloff et al. (Sokoloff, P. et al., *Eur. J. Pharmacol.* 1992, 225, 331-337). The cell line was cultured in Dulbecco's modified Eagle's medium supplemented with 2 mM glutamine, and 10% dialyzed fetal bovine serum, and were grown in an atmosphere of 5% $CO_2$ at 37° C. (Gibco™).

Membrane Preparation

Human $D_{2S}$- and $D_3$ receptors expressing cell lines were grown to confluence. The medium was removed, and the cells were washed with 10 ml PBS buffer (140 mM NaCl, 3 mM KCl, 1.5 mM KH$_2$PO$_4$, 8 mM Na$_2$HPO$_4$, pH 7.4) at 4° C. After removing the wash buffer, the cells were scraped from the flasks into 15 ml of ice-cold media, and centrifuged at 3,000 rpm for 10 minutes at 4° C. After centrifugation the medium was removed and the supernatant resuspended in ice-cold Tris-HCl buffer containing 5 mM MgCl$_2$, pH 7.4 and disrupted with a Polytron and centrifuged at 20,000 rpm, for 30 minutes at 4° C. The pellet was resuspended by sonication in ice-cold Tris-HCl buffer (containing 5 mM MgCl$_2$, pH 7.4), membrane aliquots were stored at −70° C. Determination of membrane protein was carried out by the method of Bradford (Bradford, M. M. *Anal Biochem* 1976, 72, 248-54).

Membrane Binding Assays

Cell membranes containing human $D_{2S}$ and $D_3$ receptors from CHO cells were thawed, rehomogenized with sonication at 4° C. in Tris-HCl, pH 7.4 containing 120 mM NaCl, 5 mM KCl, 2 mM CaCl$_2$ and 1 mM MgCl$_2$ (incubation buffer), and incubated with 0.2 nM [$^3$H]spiperone (106 Ci·mmol$^{-1}$, Amersham Biosciences, Freiburg, Germany), and drug diluted in incubation buffer. Non-specific binding was determined in the presence of 10 µM BP 897 ((Wermuth, C. G. et al. in *Chem. Abstr.* (Eur. Pat. 0779284, 1997)). Incubations were run at 25° C. for 120 min, and terminated by rapid filtration through PerkinElmer GF/B glass fibre filters (PerkinElmer Life Sciences, Rodgau, Germany) coated in 0.3% polyethylenimine (Sigma-Aldrich, Taufkirchen, Germany) using an Inotech cell harvester (Inotech AG, Dottikon, Switzerland). Unbound radioligand was removed with four washes of 1 ml of ice-cold 50 mM Tris-HCl buffer, pH 7.4, containing 120 mM NaCl. The filters were soaked in 9 ml Beta plate scint scintillator and counted using a PerkinElmer MicroBeta®Trilux scintillation counter (PerkinElmer Life Sciences). Competition binding data were analyzed by the software GraphPad Prism™ (2000, version 3.02, San Diego, Calif., USA), using non-linear least squares fit. For detailed screening the compounds have been tested at seven concentrations in triplicate carrying out three to five separate binding experiments for human dopamine $D_{2S}$ and for human dopamine $D_3$ receptors and expressed as mean±standard error of the mean (SEM). $K_i$ values were calculated from the IC$_{50}$ values according to Cheng-Prusoff equation (Cheng, Y. C., Prusoff, W. H. *Biochem. Pharmacol.* 1973, 22, 3099-3108.).

Results:

Table A below provides the results of the binding assays described above conducted in respect of the compounds synthesized in Example A.

TABLE A results of the binding assay described above conducted in respect of the compounds synthesized in Example A.

| Compound No. | Synthesized according to Example No. | Affinity $K_i(D_3)$ [nM] | Affinity $K_i(D2)$ [nM] | Selectivity $K_i(D_2)/K_i(D_3)$ |
|---|---|---|---|---|
| 1 | A1 | 2.26 ± 0.79 | 1683 ± 382 | 746 |
| 15 | A14 | 0.65 ± 0.09 | 347 ± 133 | 531 |
| 12 | A11 | 2.92 ± 0.48 | 2496 ± 463 | 856 |
| 4 | A4 | 2.70 ± 0.94 | 1567 ± 303 | 581 |
| 24 | A23 | 3.95 ± 1.17 | 1558 ± 464 | 394 |
| 26 | A25 | 1.52 ± 0.55 | 1812 ± 376 | 1189 |
| 3 | A3 | 25.41 ± 9.6 | 3824 ± 1104 | 151 |
| 11 | A10 | 52.63 ± 5.1 | 3388 ± 388 | 65 |
| 16 | A15 | 8.11 ± 1.23 | 4015 ± 383 | 495 |
| 17 | A16 | 2.41 ± 1 | 445 ± 55 | 184 |
| 18 | A17 | 0.57 ± 0.04 | 842 ± 35 | 1479 |
| 19 | A18 | 83 ± 2 | 2522 ± 144 | 30 |
| 23 | A22 | 1.72 ± 0.22 | 2165 ± 566 | 1262 |
| 63 | A31 | 1898 ± 510 | 24480 ± 7580 | 13 |
| 2 | A2 | 147 ± 30 | 20997 ± 2552 | 143 |
| 5 | A5 | 1.16 ± 0.17 | 873 ± 388 | 751 |
| 6 | A6 | 0.95 ± 0.20 | 459 ± 83 | 486 |
| 7 | A7 | 7.76 ± 1.37 | 9078 ± 684 | 1170 |
| 8 | A8 | 108 ± 40 | 8366 ± 3815 | 77 |
| 10 | A9 | 292 ± 41 | 23420 ± 1217 | 80 |
| 13 | A12 | 16 ± 6 | 2278 ± 105 | 141 |
| 14 | A13 | 5.61 ± 0.30 | 2101 ± 327 | 375 |
| 20 | A19 | 2.62 ± 0.16 | 1526 ± 297 | 582 |
| 65 | A33 | 0.95 0.19 | 2739 ± 1083 | 2879 |
| 32 | A27 | 67.8 ± 21.4 | 2549 ± 302 | 38 |
| 21 | A20 | 6.46 ± 3.25 | 7440 ± 2287 | 1152 |
| 25 | A24 | 2.67 ± 1.32 | 7610 ± 1814 | 2850 |
| 27 | A26 | 2.25 ± 1.24 | 3194 ± 1473 | 1422 |
| 22 | A21 | 2.97 ± 1.23 | 4872 ± 1050 | 1642 |
| 61 | A29 | 2.09 ± 0.57 | 3428 ± 1286 | 1640 |
| 62 | A30 | 7.31 ± 2.86 | 4878 ± 1894 | 667 |
| 64 | A32 | 6.29 ± 1.80 | 2733 ± 611 | 435 |
| 60 | A28 | 3.36 ± 1.21 | 2182 ± 1638 | 649 |

TABLE B results of the binding assay described above conducted in respect of the compounds synthesized in Example B.

| Compound No. | Synthesized according to Example No. | Affinity $K_i(D_3)$ [nM] | Affinity $K_i(D2)$ [nM] | Selectivity $K_i(D_2)/K_i(D_3)$ |
|---|---|---|---|---|
| 68 | B7 | 1.54 ± 0.46 | 457 ± 228 | 297 |
| 66 | B5 | 7.23 ± 1.00 | 4135 ± 1556 | 572 |
| 67 | B6 | 0.90 ± 0.05 | 1388 ± 304 | 1550 |
| 9 | B1 | 0.55 ± 0.19 | 299 ± 38 | 542 |
| 42 | B2 | 631 ± 388 | 16653 ± 3382 | 26 |
| 43 | B3 | 29.4 ± 7.5 | 1444 ± 273 | 49 |
| 44 | B4 | 836 ± 211 | 16132 ± 8853 | 19 |

TABLE C results of the binding assay described above conducted in respect of the compounds synthesized in Example C.

| Compound No. | Synthesized according to Example No. | Affinity $K_i(D_3)$ [nM] | Affinity $K_i(D2)$ [nM] | Selectivity $K_i(D_2)/K_i(D_3)$ |
|---|---|---|---|---|
| 28 | C1 | 13.5 ± 1.1 | 148 ± 23 | 11 |
| 33 | C5 | 22.7 ± 13.5 | 468 ± 13.5 | 19 |
| 38 | C10 | 27.4 ± 14.8 | 5270 ± 1849 | 192 |
| 39 | C11 | 12.9 ± 3.8 | 3181 ± 1730 | 247 |
| 30 | C3 | 55.3 ± 16.1 | 480 ± 51 | 8.7 |
| 35 | C7 | 21.7 ± 10.6 | 61.3 ± 19.1 | 2 |
| 36 | C8 | 35 ± 22 | 129 ± 36 | 4 |
| 37 | C9 | 7.6 ± 1.6 | 79.4 ± 49.7 | 7 |
| 29 | C2 | 89 ± 1.7 | 140 ± 122 | 2 |
| 31 | C4 | 26.5 ± 4.4 | 929 ± 103 | 35 |
| 34 | C6 | 4.5 ± 0.7 | 132 ± 40 | 29 |

TABLE D results of the binding assay described above conducted in respect of the compounds synthesized in Example D.

| Compound No. | Synthesized according to Example No. | Affinity $K_i(D_3)$ [nM] | Affinity $K_i(D2)$ [nM] | Selectivity $K_i(D_2)/K_i(D_3)$ |
|---|---|---|---|---|
| 69 | D1 | 51 ± 10 | 4672 ± 1320 | 91 |

These data demonstrate that compounds according to the invention have affinity for dopamine receptors.

It will be appreciated that each of the compounds had an affinity for both D2 and D3 receptors but had best affinity for the D3 receptor.

Example F

In Vivo Testing

In vivo tests were conducted to examine the efficacy of compounds according to the invention in a functional assay of dopaminergic receptor activation.
Methods
Preparation of 6-OHDA-Lesioned Rat Model of Parkinson's Disease Male Sprague-Dawley rats weighing 290-350 g were used. The rats were housed in a temperature-controlled room under a 12 hour light/dark cycle with free access to food and water. Thirty minutes prior to surgery, the animals were given the monoamine oxidase-B inhibitor pargyline (5 mg/kg i.p.;) and the noradrenaline uptake inhibitor desipramine (25 mg/kg i.p.). The rats were then placed under general anaesthesia (Flourothane) and immobilised in stereotaxic frame. Following reflection of cranial skin and periostium, a small bur-hole was made in the skull on the right side and a small puncture was made in the dura mater. Each animal then received a unilateral injection of 2.5 µl of the neurotoxin 6-hydroxydopamine hydrobromide (6-OHDA HBr; 5 mg/ml in sterile water with 0.1% ascorbic acid; i.e. 12.5 µg 6-OHDA per rat) into the right medial forebrain bundle at stereotaxic co-ordinates −2.8 mm from bregma, 2 mm lateral to the midline, and 9 mm below the skull. The 6-OHDA injection was made over a 5 minute period using a 5 µl Hamilton syringe. The rats were allowed to recover for 3 weeks following the lesion. Animals then received 0.05 mg/kg s.c. apomorphine to assess the extent of lesion. Animals displaying clear rotational behaviour directed contralateral to the lesioned side were selected for further studies.
Study Design Only lesioned animals were used in the study (as determined by apomorphine rotation).

Animals were administered a dose of the test compound at 1 mg/kg or 3 mg/kg (i.p.) and rotational behaviour was assessed for up to 4 hours following drug administration using automated rotometers. Alternatively, animals were administered a dose of the test compound at 10 mg/kg (p.o.) and rotational behaviour was assessed for up to 8 hours following drug administration using automated rotometers.

Each compound was administered to at least 5 rats.
Analysis of Parametric Data

Total net rotational activity. This parameter is calculated as the total number of 180° rotations (net contralateral) over the duration of the experiment.

Data were analysed independently for each novel compound with appropriate parametric statistics. All tests were carried out in Graphpad Prism Version 3.
Results Compounds according to the invention, which were acting as dopamine receptor agonists, were able to induce rotational activity in animals and thereby reverse the parkinsonism induced by the lesions. The effect of the compounds was significant when compared to control animals (data not shown).

A skilled person will appreciate that this in vivo model is considered to be one of the "gold standards" animal models for testing the efficacy of candidate drugs for treating movement disorders and particularly Parkinson's disease. Accordingly the inventors have demonstrated that compounds according to the invention may be used to treat medical conditions characterized by an imbalance in dopamine receptor activity and particularly parkinsonism.

The results of the study (i.p. administration) for compounds 1, 15, 12, 20, 24, 26, 21, 25, 27 and 65 prepared in Example A are presented below in FIGS. 1 to 10 respectively.

The results of the study (i.p. administration) for compounds 9, 68, 66 and 67 prepared in Example B are presented below in FIGS. 11 to 14 respectively.

The results of the study (i.p. administration) for compounds 28, 34, 33, 38 and 39 prepared in Example C are presented below in FIGS. 15 to 19 respectively.

The results of the study (p.o. administration) for compounds 28, 33 and 34 prepared in Example C are presented below in FIGS. 20 to 22 respectively.

The vertical axis on FIGS. 1 to 22 (rotations) indicates the level of rotational activity which is a function of dopamine receptor activity and is particularly illustrative of an antiparkinson effect of the compounds. The magnitude of the antiparkinson effects demonstrated with the novel compounds (administration by i.p. and p.o.) are at least equivalent to what would be observed with current therapies, such as L-DOPA.

It is well known that increasing the level of L-DOPA therapy is associated with hyperactivity and the occurrence of side-effects, such as dyskinesias and hallucinations. Surprisingly, for the novel compounds described herein, increasing the dose administered does not lead to a corresponding increase in activity (e.g. FIGS. 10, 11, 12, 16). This indicates that the compounds will not have the unwanted side-effects associated with known agents such as L-DOPA which cause much higher rotational activity as their dose increases. Additionally, this means that the compounds according to the invention are less "dose-critical" than known agents such as L-DOPA.

It is also well known that the duration of action of antiparkinson agents is related to the appearance of unwanted side-effects. The shorter the duration of action, the greater the occurrence of side effects and vice versa. Preferred compounds according to the invention show a long duration of action, which is highly desirable in such agents (see FIGS. 1 and 2). This suggests that they would be less likely to induce side-effects, such as dyskinesias.

Some of the novel compounds demonstrate both a rapid onset of action and a short duration of action (e.g. see FIGS. 5, 8, 14 and 19). Such compounds are particularly useful as acute rescue therapies in Parkinson's disease and also have utility for the treatment of sexual dysfunction (where a short duration of action is desirable).

Some of the novel compounds, especially when administered orally, show a long duration of action (for example of up to 8 hours). This may be advantageous to provide action for example over a period of time such as the period of a working day. Some of the novel compounds when administered orally also show a surprisingly fast onset of action. Thus, the compounds of the present invention may desirably be administered orally.

The invention claimed is:

1. A compound of formula (I):

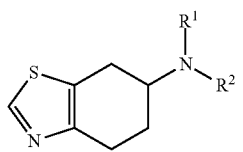

(I)

wherein

R$^1$ is selected from the group consisting of substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, and substituted or unsubstituted heterocyclic ring; and R$^2$ comprises a polar moiety, P, and at least one linking group, Z, linking the polar moiety, P, to the nitrogen of the NR$^1$ group; and wherein said at least one linking group, Z, is selected from one or more of the group consisting of substituted or unsubstituted $C_2$-$C_6$ alkylene, substituted or unsubstituted $C_2$-$C_6$ alkenylene, substituted or unsubstituted $C_2$-$C_6$ alkynylene, substituted or unsubstituted carbocyclic ring, and substituted or unsubstituted heterocyclic ring;

and wherein said polar moiety, P, comprises a heteroatom selected from the group consisting of oxygen, sulfur, and nitrogen.

2. A compound according to claim 1, wherein R$^1$ is a substituted or unsubstituted alkyl, alkenyl, alkynyl or alkoxy group, wherein said substituted or unsubstituted alkyl, alkenyl, alkynyl or alkoxy group is optionally a $C_1$-$C_4$ substituted or unsubstituted alkyl, alkenyl, alkynyl or alkoxy group, wherein said substituted or unsubstituted alkyl, alkenyl, alkynyl or alkoxy group is optionally substituted with a first substituent selected from the group consisting of:

(i) a carboxy group, a thiocarboxy group, a carboxamido group, a sulfo group, a sulfino group, a sulfeno group, an ester group, a carbamoyl group, an imido group, a nitro group, a formyl group, an oxo group, a hydroxy group, an oxy group, and derivatives thereof, (ii) a thiocarboxy group, a sulfo group, a sulfino group, a sulfeno group, a sulfonyl group, a sulfo group, a sulfinyl group, a thioformyl group, a sulfanyl group, a thio group, a disulfanyl group and derivatives thereof, (iii) a carbamoyl group, an imido group, an amidino group, a cyano group, an amino group, an imino group, an azido group, a nitro group, a hydrazino group, and derivatives thereof, or (iv) a substituted or unsubstituted carbocyclic group and a substituted or unsubstituted heterocyclic group.

3. A compound according to claim 1, wherein R$^1$ is a substituted or unsubstituted alkyl, alkenyl, alkynyl or alkoxy group and wherein said substituted or unsubstituted alkyl, alkenyl, alkynyl or alkoxy group is optionally substituted with a first substituent selected from the group consisting of a substituted or unsubstituted carbocyclic group and a substituted or unsubstituted heterocyclic group, wherein:

(A) said heterocyclic group is a saturated, unsaturated or aromatic heterocyclic group, wherein said substituted or unsubstituted heterocyclic group contains a ring heteroatom optionally selected from the group consisting of:

(i) oxygen, sulfur, selenium, nitrogen, or phosphorous, (ii) a furanyl group, an oxazolyl group, an isoxazolyl group, a pyranyl group, an oxazinyl group, or a dioxanyl group, (iii) an aziridine group, a pyrrolyl group, a pyrazolyl group, an imidazolyl group, a triazolyl group, a tetrazolyl group, an oxazolyl group, a thiazolyl group, an isothiazolyl group, a pyridinyl group, a pyridazinyl group, a pyrimidinyl group, a pyrazinyl group, a piperazinyl group, an oxoazinyl group, or a thiazinyl group, and (iv) a thiophenyl group, a hydrothiophenyl group, a thiazolyl group, an isothiazolyl group, a dithiolanyl group, a thianyl group, a thiinyl group, a thiazine group, or a dithianyl group; or (B) said carbocyclic group is a saturated, unsaturated, or aromatic carbocyclic group.

4. A compound according to claim 1, wherein said polar moiety, P, is selected from the group consisting of:

(i) a carboxy group, a thiocarboxy group, a carboxamido group, a sulfo group, a sulfino group, a sulfeno group, an ester group, a carbamoyl group, an imido group, a nitro group, a formyl group, an oxo group, a hydroxy group, an oxy group, or a derivatives thereof, (ii) a thiocarboxy group, a sulfo group, a sulfino group, a sulfeno group, a sulfonyl group, a sulfo group, a sulfinyl group, a thioformyl group, a sulfanyl group, a thio group, a disulfanyl group or a derivative thereof, (iii) a carbamoyl group, an imido group, an amidino group, a cyano group, an amino group, an imino group, an azido group, a nitro group, a hydrazino group, or a derivative thereof, (iv) a substituted or unsubstituted heterocyclic group, wherein said heterocyclic group is optionally a saturated, unsaturated or aromatic heterocyclic group, and (v) an amido group, an inverse amido group, an ether group, a thioether group, a carbamate group, a urea group, a thio urea group, or an amino group.

5. A compound according to claim 1, wherein said polar moiety, P, is selected from the group consisting of a substituted or unsubstituted heterocyclic group, and wherein said substituted or unsubstituted heterocyclic group contains a ring heteroatom selected from the group consisting of:
(i) oxygen, sulfur, or nitrogen,
(ii) a furanyl group, an oxazolyl group, an isoxazolyl group, a pyranyl group, an oxazinyl group, or a dioxanyl group,
(iii) an aziridine group, a pyrrolyl group, a pyrazolyl group, an imidazolyl group, a triazolyl group, a tetrazolyl group, an oxazolyl group, a thiazolyl group, an isothiazolyl group, a pyridinyl group, a pyridazinyl group, a pyrimidinyl group, a pyrazinyl group, a piperazinyl group, an oxoazinyl group, or a thiazinyl group, and
(iv) a thiophenyl group, a hydrothiophenyl group, a thiazolyl group, an isothiazoly group, a dithiolanyl group, a thianyl group, a thiinyl group, a thiazine group, and a dithianyl group.

6. A compound according to claim 1, wherein:
(i) said compound has the formula (Ia):

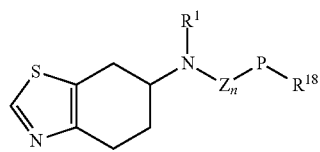

(Ia)

wherein:
$R^{18}$ is selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, and substituted or unsubstituted heterocyclic ring; and
n is any integer of 1 or more,
(ii) said compound has the formula (Id):

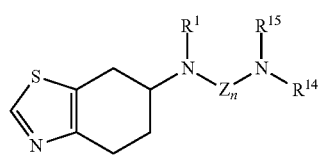

(Id)

wherein:
each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^{16}$R$^{17}$, or
$R^{14}$ and $R^{15}$ are linked such that —$R^{14}$—N—$R^{15}$— forms part of a substituted or unsubstituted heterocyclic ring;

each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{16}$ and $R^{17}$ are linked such that —$R^{16}$—N—$R^{17}$— forms part of a substituted or unsubstituted heterocyclic ring;
and n is any integer of 1 or more; or,
wherein said compound has the formula:

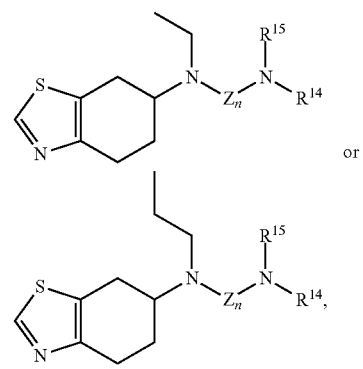

or (iii) said compound has the formula:

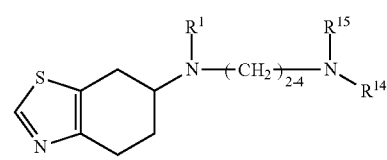

wherein each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^{16}$R$^{17}$, or
$R^{14}$ and $R^{15}$ are linked such that —$R^{14}$—N—$R^{15}$— forms part of a substituted or unsubstituted heterocyclic ring;
each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{16}$ and $R^{17}$ are linked such that —$R^{16}$—N—$R^{17}$— forms part of a substituted or unsubstituted heterocyclic ring, or
(iv) said compound has the formula:

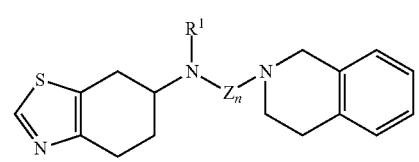

7. A compound according to claim 1, wherein said compound has the formula (Id):

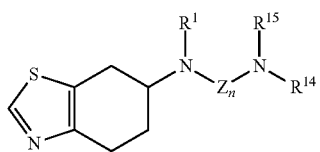

wherein each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{16}R^{17}$, or $R^{14}$ and $R^{15}$ are linked such that —$R^{14}$—N—$R^{15}$— forms part of a substituted or unsubstituted heterocyclic ring;

each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{16}$ and $R^{17}$ are linked such that —$R^{16}$—N—$R^{17}$— forms part of a substituted or unsubstituted heterocyclic ring;

and n is any integer of 1 or more, or, wherein the compound has the formula:

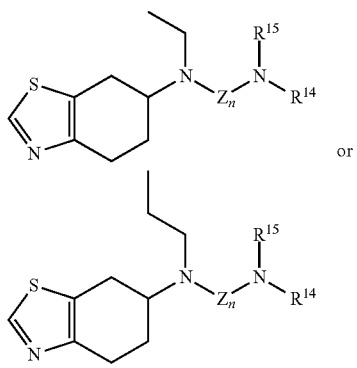

or wherein said compound has the formula:

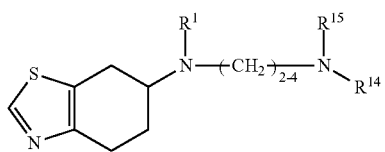

wherein, each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{16}R^{17}$, or $R^{14}$ and $R^{15}$ are linked such that —$R^{14}$—N—$R^{15}$— forms part of a substituted or unsubstituted heterocyclic ring;

each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{16}$ and $R^{17}$ are linked such that —$R^{16}$—N—$R^{17}$— forms part of a substituted or unsubstituted heterocyclic ring;

wherein one of $R^{14}$ and $R^{15}$ is :

a $C_1$-$C_4$ substituted or unsubstituted alkyl group, (ii) an ethyl group, (iii) selected from the group consisting of a substituted or unsubstituted monocyclic heterocyclic ring, a substituted or unsubstituted bicyclic heterocyclic ring and a substituted or unsubstituted tricyclic heterocyclic ring, (iv) wherein $R^{14}$ and $R^{15}$ are linked to form part of a substituted or unsubstituted piperidine ring, and optionally, wherein said piperidine ring is connected to an aromatic group, or (v) wherein $R^{14}$ and $R^{15}$ are linked to form part of a substituted or unsubstituted piperazine ring.

8. A compound according to claim 1 wherein said compound has the formula (Id)

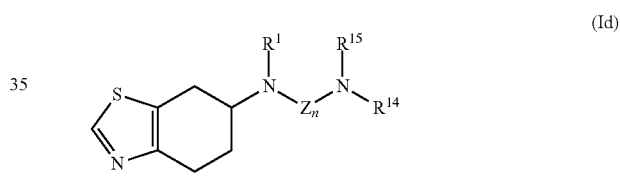

wherein, each of $R^{14}$ and $R^{15}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{16}R^{17}$, or $R^{14}$ and $R^{15}$ are linked such that —$R^{14}$—N—$R^{15}$— forms part of a substituted or unsubstituted heterocyclic ring;

each of $R^{16}$ and $R^{17}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{16}$ and $R^{17}$ are linked such that —$R^{16}$—N—$R^{17}$— forms part of a substituted or unsubstituted heterocyclic ring;

Z is a linking group; and n is any integer of 1 or more, wherein:

(i) $R^1$ and $R^{15}$ are linked to form part of the same heterocyclic aromatic or non-aromatic ring, or (ii) $R^1$ and $R^{15}$ are linked to form part of a substituted or unsubstituted piperazine ring, wherein $R^{14}$ is a substituted or unsubstituted $C_1$-$C_4$ alkyl group.

9. A compound according to claim 1 having the formula:

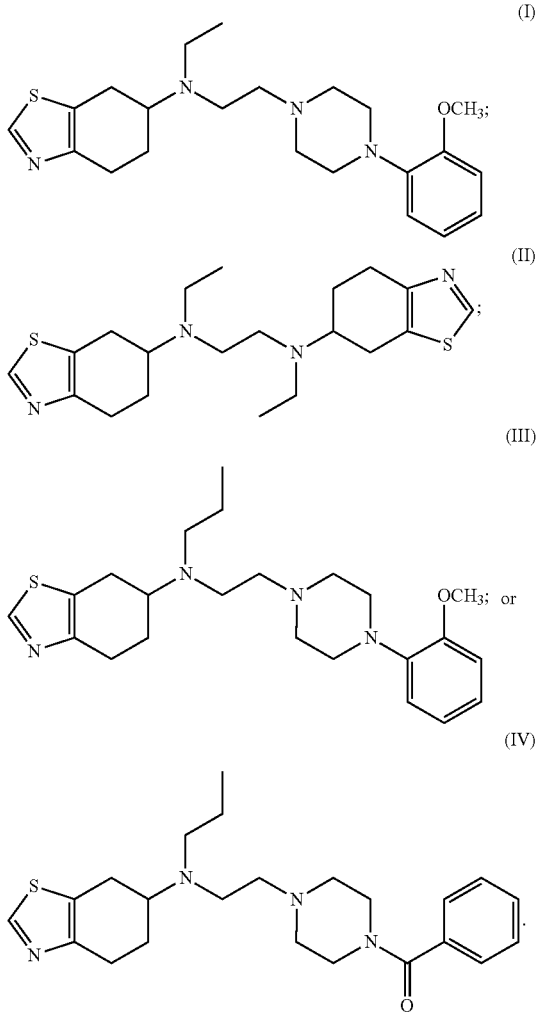

10. A compound according to claim 1, wherein:
(i) said compound has the formula (Ib):

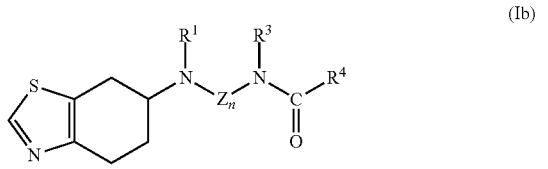

wherein
each of $R^3$ and $R^4$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^5$R$^6$, or $R^3$ and $R^4$ are linked such that —R$^3$—N—C(O)—R$^4$— forms part of a substituted or unsubstituted heterocyclic ring;

each of $R^5$ and $R^6$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^5$ and $R^6$ are linked such that —R$^5$—N—R$^6$— forms part of a substituted or unsubstituted heterocyclic ring;

Z is a linking group; and n is any integer of 1 or more;

wherein Z is a substituted or unsubstituted alkylene group; wherein said alkylene group is (a) a $C_2$-$C_6$ substituted or unsubstituted alkylene group, or (b) selected from the group consisting of ethylene, propylene, iso-propylene, butylene, iso-butylene and tert-butylene; or (ii) said compound has the formula:

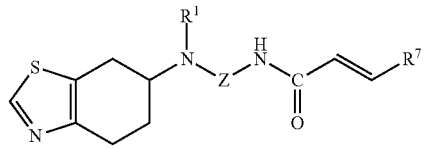

wherein $R^7$ is (aa) a substituted or unsubstituted phenyl group, or (bb) a phenyl group substituted with one or more halogen atoms.

11. A compound according to claim 1, wherein said compound has the formula (lb):

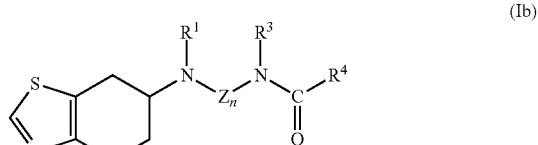

wherein, each of $R^3$ and $R^4$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^5$R$^6$, or $R^3$ and $R^4$ are linked such that —R$^3$—N—C(O)—R$^4$— forms part of a substituted or unsubstituted heterocyclic ring;

each of $R^5$ and $R^6$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^5$ and $R^6$ are linked such that —R$^5$—N—R$^6$— forms part of a substituted or unsubstituted heterocyclic ring;

Z is a linking group; and n is any integer of 1 or more, wherein:

(i) $R^4$ is a $C_6$-$C_{10}$ substituted or unsubstituted aromatic carbocyclic ring;

(ii) $R^4$ is a $C_2$-$C_4$ substituted or unsubstituted alkenyl group;

(iii) $R^4$ is a substituted or unsubstituted phenyl ring or a substituted or unsubstituted naphthyl ring;

(iv) R⁴ is a $C_4$-$C_{10}$ substituted or unsubstituted carbocyclic non-aromatic ring;
(v) R⁴ is a substituted or unsubstituted cyclopentyl ring or a substituted or unsubstituted cyclohexyl ring;
(vi) R4 has the formula:

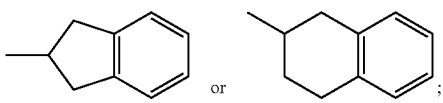

(vii) R⁴ is a substituted or unsubstituted adamantyl group;
(viii) R⁴ is a substituted or unsubstituted heterocyclic aromatic or non-aromatic ring;
(ix) R⁴ is a substituted or unsubstituted benzothiazolyl group;
(x) R⁴ has the formula:

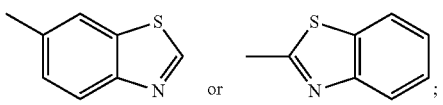

(xi) R⁴ is selected from the group consisting of substituted or unsubstituted pyrrole, substituted or unsubstituted thiophene and substituted or unsubstituted furan;
(xii) R⁴ is substituted or unsubstituted benzothiophene;
(xiii) R⁴ is a substituted or unsubstituted thiazole;
(xiv) R⁴ has the formula:

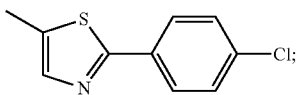

(xv) R⁴ is —NR⁸R⁹ and one of R⁸ and R⁹ is H;
(xvi) R⁴ is —NR⁸R⁹ and one of R⁸ and R⁹ is a substituted or unsubstituted carbocyclic non-aromatic ring;
(xvii) R⁴ has the formula:

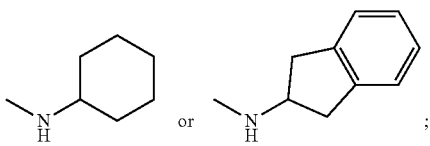

(xviii) R⁴ is —NR⁸R⁹ and R⁸ and R⁹ are linked such that —R⁸—N—R⁹— forms part of a substituted or unsubstituted 5- to 7- membered ring;
(xix) R⁴ is —NR⁸R⁹ and R⁸ and R⁹ are linked such that —R⁸—N—R⁹— forms part of a substituted or unsubstituted piperidine ring;

(xx) R⁴ has the formula:

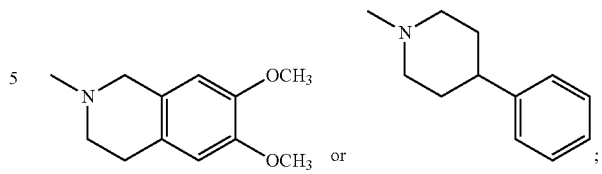

(xxi) R⁴ is —NR⁸R⁹ and R⁸ and R⁹ are linked such that —R⁸—N—R⁹— forms part of a substituted or unsubstituted pyrrolidine ring;
(xxii) R⁴ has the formula:

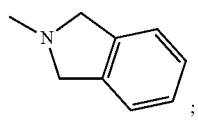

(xxiii) R⁴ is —NR⁸R⁹ and R⁸ and R⁹ are linked such that —R⁸—N—R⁹— forms part of a substituted or unsubstituted piperazine ring;
(xxiv) R⁴ has the formula:

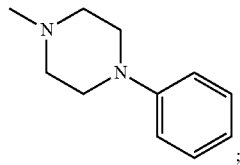

(xxv) R⁴ has the formula:

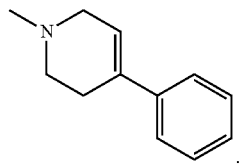

12. A compound having the formula:

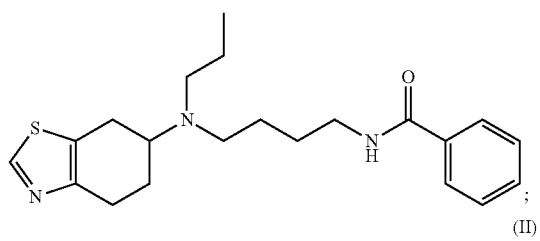

(I)

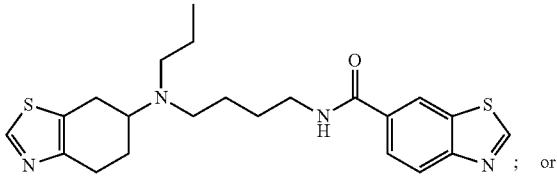

(II)

; or

-continued

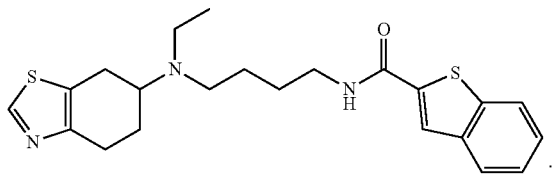
(III)

13. A compound according to claim 1, wherein said compound has the formula (Ic):

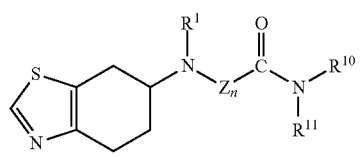
(Ic)

wherein each of $R^{10}$ and $R^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{12}R^{13}$, or $R^{10}$ and $R^{11}$ are linked such that —$R^{10}$—N—$R^{11}$— forms part of a substituted or unsubstituted heterocyclic ring;

each of $R^{12}$ and $R^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{12}$ and $R^{13}$ are linked such that —$R^{12}$—N—$R^{13}$— forms part of a substituted or unsubstituted heterocyclic ring;

Z is a linking group; and n is any integer of 1 or more; or, wherein the compound has the formula:

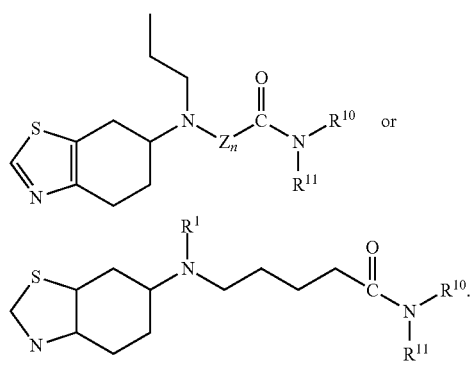

14. A compound according to claim 1, wherein said compound has the formula (Ic):

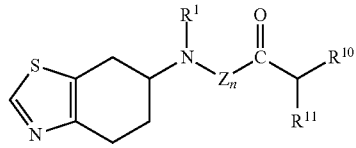
(Ic)

wherein, each of $R^{10}$ and $R^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{12}R^{13}$, or $R^{10}$ and $R^{11}$ are linked such that —$R^{10}$—N—$R^{11}$— forms part of a substituted or unsubstituted heterocyclic ring;

each of $R^{12}$ and $R^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{12}$ and $R^{13}$ are linked such that -$R^{12}$-N-$R^{13}$- forms part of a substituted or unsubstituted heterocyclic ring;

Z is a linking group; and n is any integer of 1 or more;

wherein:

(i) Z is a substituted or unsubstituted alkylene group, and wherein said alkylene group is a $C_2$-$C_6$ substituted or unsubstituted alkylene group, or said alkylene group is selected from the group consisting of ethylene, propylene, iso-propylene, butylene, iso-butylene and tertbutylene; or (ii) Z is a substituted or unsubstituted arylene group, wherein said arylene group is a $C_6$-$C_{10}$ substituted or unsubstituted arylene group, or said arylene group is selected from the group consisting of phenylene, benzylene, tolylene, and xylylene.

15. A compound according to claim 1, wherein said compound has the formula:

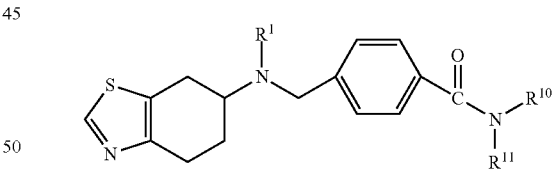

wherein each of $R^{10}$ and $R^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —$NR^{12}R^{13}$, or $R^{10}$ and $R^{11}$ are linked such that —$R^{10}$—N—$R^{11}$— forms part of a substituted or unsubstituted heterocyclic ring;

each of $R^{12}$ and $R^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or $R^{12}$ and $R^{13}$ are linked such that —R$^{12}$—N—R$^{13}$— forms part of a substituted or unsubstituted heterocyclic ring.

16. A compound according to claim 1, wherein said compound has the formula (Ic):

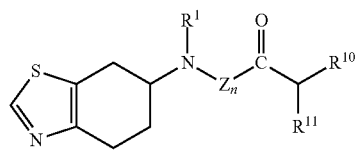

(Ic)

wherein,
each of R$^{10}$ and R$^{11}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring, substituted or unsubstituted heterocyclic ring, and —NR$^{12}$R$^{13}$, or
R$^{10}$ and R$^{11}$ are linked such that —R$^{10}$—N—R$^{11}$— forms part of a substituted or unsubstituted heterocyclic ring;
each of R$^{12}$ and R$^{13}$ is separately selected from the group consisting of H, substituted or unsubstituted alkyl, substituted or unsubstituted alkenyl, substituted or unsubstituted alkynyl, substituted or unsubstituted alkoxy, substituted or unsubstituted amino, substituted or unsubstituted carbocyclic ring, substituted or unsubstituted heterocyclic ring, or R$^{12}$ and R$^{13}$ are linked such that —R$^{12}$—N—R$^{13}$— forms part of a substituted or unsubstituted heterocyclic ring;
and n is any integer of 1 or more; or,
wherein the compound has the formula:

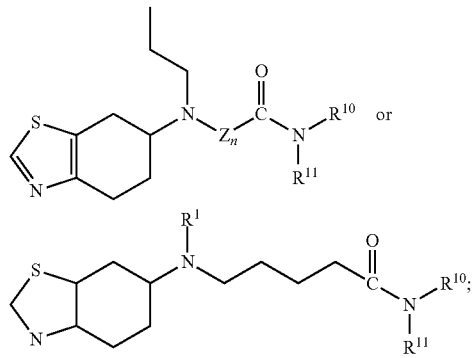

or wherein said compound has the formula:

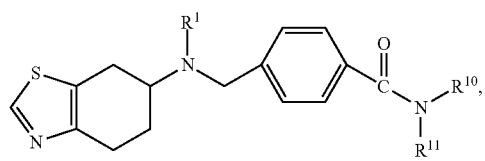

wherein:
(A) one of R$^{10}$ and R$^{11}$ is H; or
(B) R$^{10}$ and R$^{11}$ are linked to form part of a substituted or unsubstituted piperazine ring.

17. A compound according to claim 1 having the formula:

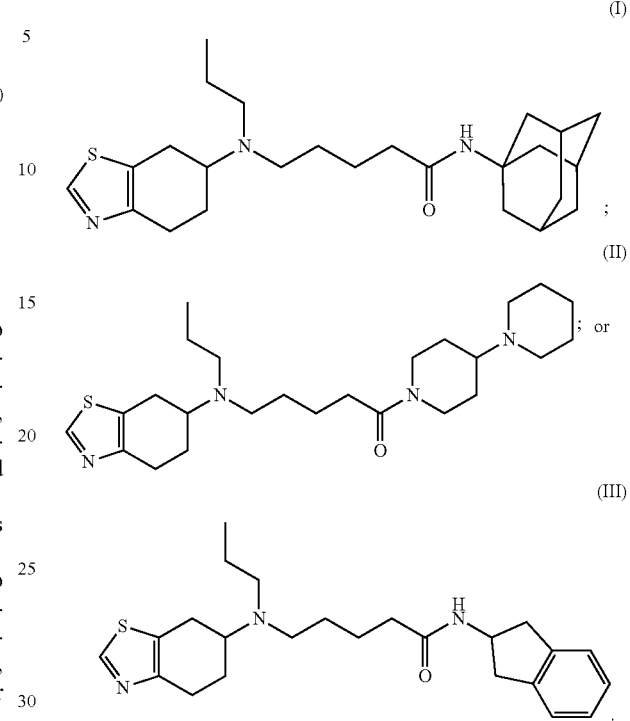

18. A compound according to claim 1, wherein said compound has the formula (Ie):

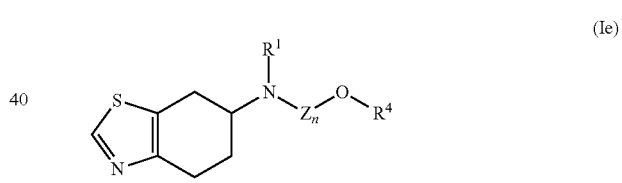

(Ie)

wherein
R$^{4}$ is selected from the group consisting of H, substituted or unsubstituted alkyl, substituted or unsubstituted alkenyl, substituted or unsubstituted alkynyl, substituted or unsubstituted alkoxy, substituted or unsubstituted carbocyclic ring and substituted or unsubstituted heterocyclic ring.

19. A compound according to claim 1 having the formula:

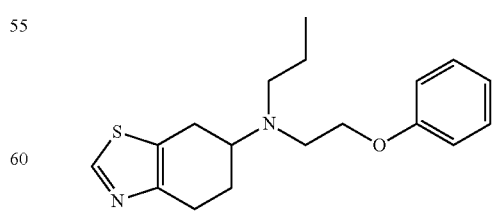

20. A pharmaceutical composition comprising a compound according to claim 1.

21. A method of treating medical conditions selected from the group consisting of parkinsonism, dyskinesia, schizophrenia, addiction, sexual dysfunction, bipolar disorder, attention deficit hyperactivity disorder, depression, anxiety, cognitive impairment, dementia, amnesia, eating disorders, sleep disorders, movement disorders, circadian rhythm disorders, gastric motility disorders, amyotrophic lateral sclerosis, anhedonia, and restless leg syndrome comprising administering to a subject in need thereof a therapeutically effective amount of a compound according to claim 1.

* * * * *